United States Patent
Hayter et al.

(10) Patent No.: US 12,290,354 B2
(45) Date of Patent: May 6, 2025

(54) TEMPERATURE-COMPENSATED ANALYTE MONITORING DEVICES, SYSTEMS, AND METHODS THEREOF

(71) Applicant: Abbott Diabetes Care Inc., Alameda, CA (US)

(72) Inventors: Gary A. Hayter, Oakland, CA (US); Daniel M. Bernstein, El Granada, CA (US); Martin J. Fennell, Concord, CA (US); Michael R. Love, Pleasanton, CA (US); Kenneth J. Doniger, Menlo Park, CA (US); Songbiao Zhang, Fremont, CA (US); Mark K. Sloan, Hayward, CA (US); Hyun Cho, Berkeley, CA (US); Theodore J. Kunich, Pleasanton, CA (US); Jean-Pierre Cole, Tracy, CA (US); Christopher A. Thomas, San Leandro, CA (US); Erwin S. Budiman, Fremont, CA (US); David L. Li, Fullerton, CA (US); Royce Cheng, San Francisco, CA (US); Udo Hoss, Castro Valley, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 18/152,619

(22) Filed: Jan. 10, 2023

(65) Prior Publication Data

US 2023/0143496 A1  May 11, 2023

Related U.S. Application Data

(60) Continuation of application No. 16/525,915, filed on Jul. 30, 2019, now Pat. No. 11,571,147, which is a
(Continued)

(51) Int. Cl.
  *A61B 5/145* (2006.01)
  *A61B 5/00* (2006.01)
  (Continued)

(52) U.S. Cl.
  CPC ............ *A61B 5/14532* (2013.01); *A61B 5/01* (2013.01); *A61B 5/14503* (2013.01);
  (Continued)

(58) Field of Classification Search
  CPC ... A61B 5/14532; A61B 5/01; A61B 5/14503; A61B 5/7225; A61B 5/1473; A61B 2560/0252; A61B 2562/0271
  See application file for complete search history.

(56) References Cited

U.S. PATENT DOCUMENTS 3,581,062 A  5/1971 Aston
3,729,343 A  4/1973 Thomas
(Continued)

FOREIGN PATENT DOCUMENTS

CA  2143172 C  7/2005
CA  2396613 C  3/2008
(Continued)

OTHER PUBLICATIONS

Extended European Search Report in counterpart European application No. EP 19155366.8 dated Aug. 30, 2019 (8 pages).
(Continued)

*Primary Examiner* — Eric J Messersmith
(74) *Attorney, Agent, or Firm* — ONE LLP

(57) ABSTRACT

Methods of compensating for ambient temperature using temperature sensors, the method comprising: sampling at a first sampling rate, with a processor, first temperature measurements from a first temperature sensor on an on-body sensor. Then determining, with a processor, first ambient-compensated temperatures from the first temperature mea-
(Continued)

surements; and determining, with a processor, final ambient-compensated temperatures by applying a correction gain or factor to the first ambient-compensated temperatures. Wherein the correction gain or factor changes value at a slower rate than the sampling rate.

12 Claims, 12 Drawing Sheets

Related U.S. Application Data continuation of application No. 15/873,464, filed on Jan. 17, 2018, now Pat. No. 10,398,363, which is a division of application No. 13/526,394, filed on Jun. 18, 2012, now Pat. No. 9,974,472.

(60) Provisional application No. 61/497,821, filed on Jun. 16, 2011.

(51) Int. Cl.
  *A61B 5/01* (2006.01)
  *A61B 5/1473* (2006.01)
(52) U.S. Cl.
  CPC .......... *A61B 5/7225* (2013.01); *A61B 5/1473* (2013.01); *A61B 2560/0252* (2013.01); *A61B 2562/0271* (2013.01)

(56) References Cited

U.S. PATENT DOCUMENTS

| | | | |
|---|---|---|---|
| 3,926,760 A | 12/1975 | Allen et al. | |
| 3,949,388 A | 4/1976 | Fuller | |
| 3,960,497 A | 6/1976 | Acord | |
| 4,036,749 A | 7/1977 | Anderson | |
| 4,055,175 A | 10/1977 | Clemens et al. | |
| 4,129,128 A | 12/1978 | McFarlane | |
| 4,245,634 A | 1/1981 | Albisser et al. | |
| 4,327,725 A | 5/1982 | Cortese et al. | |
| 4,344,438 A | 8/1982 | Schultz | |
| 4,349,728 A | 9/1982 | Phillips et al. | |
| 4,373,527 A | 2/1983 | Fischell | |
| 4,392,849 A | 7/1983 | Petre et al. | |
| 4,425,920 A | 1/1984 | Bourland et al. | |
| 4,431,004 A * | 2/1984 | Bessman ............... | C12Q 1/006 600/347 |
| 4,441,968 A | 4/1984 | Emmer et al. | |
| 4,464,170 A | 8/1984 | Clemens et al. | |
| 4,478,976 A | 10/1984 | Goertz et al. | |
| 4,494,950 A | 1/1985 | Fischell | |
| 4,509,531 A | 4/1985 | Ward | |
| 4,527,240 A | 7/1985 | Kvitash | |
| 4,538,616 A | 9/1985 | Rogoff | |
| 4,545,382 A | 10/1985 | Higgins et al. | |
| 4,619,793 A | 10/1986 | Lee | |
| 4,671,288 A | 6/1987 | Gough | |
| 4,703,756 A | 11/1987 | Gough et al. | |
| 4,711,245 A | 12/1987 | Higgins et al. | |
| 4,731,726 A | 3/1988 | Allen, III | |
| 4,749,985 A | 6/1988 | Corsberg | |
| 4,757,022 A | 7/1988 | Shults et al. | |
| 4,777,953 A | 10/1988 | Ash et al. | |
| 4,779,618 A | 10/1988 | Mund et al. | |
| 4,847,785 A | 7/1989 | Stephens | |
| 4,854,322 A | 8/1989 | Ash et al. | |
| 4,871,351 A | 10/1989 | Feingold | |
| 4,890,620 A | 1/1990 | Gough | |
| 4,925,268 A | 5/1990 | Iyer et al. | |
| 4,953,552 A | 9/1990 | DeMarzo | |
| 4,986,271 A | 1/1991 | Wilkins | |
| 4,995,402 A | 2/1991 | Smith et al. | |
| 5,000,180 A | 3/1991 | Kuypers et al. | |
| 5,002,054 A | 3/1991 | Ash et al. | |
| 5,019,974 A | 5/1991 | Beckers | |
| 5,050,612 A | 9/1991 | Matsumura | |
| 5,051,688 A | 9/1991 | Murase et al. | |
| 5,055,171 A | 10/1991 | Peck | |
| 5,068,536 A | 11/1991 | Rosenthal | |
| 5,082,550 A | 1/1992 | Rishpon et al. | |
| 5,106,365 A | 4/1992 | Hernandez | |
| 5,122,925 A | 6/1992 | Inpyn | |
| 5,135,004 A | 8/1992 | Adams et al. | |
| 5,165,407 A | 11/1992 | Wilson et al. | |
| 5,202,261 A | 4/1993 | Musho et al. | |
| 5,204,264 A | 4/1993 | Kaminer | |
| 5,210,778 A | 5/1993 | Massart | |
| 5,228,449 A | 7/1993 | Christ et al. | |
| 5,231,988 A | 8/1993 | Wernicke et al. | |
| 5,246,867 A | 9/1993 | Lakowicz et al. | |
| 5,251,126 A | 10/1993 | Kahn et al. | |
| 5,262,035 A | 11/1993 | Gregg et al. | |
| 5,262,305 A | 11/1993 | Heller et al. | |
| 5,264,014 A | 11/1993 | Lannefors et al. | |
| 5,264,104 A | 11/1993 | Gregg et al. | |
| 5,264,105 A | 11/1993 | Gregg et al. | |
| 5,279,294 A | 1/1994 | Anderson et al. | |
| 5,285,792 A | 2/1994 | Sjoquist et al. | |
| 5,293,877 A | 3/1994 | O'Hara et al. | |
| 5,299,571 A | 4/1994 | Mastrototaro | |
| 5,320,715 A | 6/1994 | Berg | |
| 5,320,725 A | 6/1994 | Gregg et al. | |
| 5,322,063 A | 6/1994 | Allen et al. | |
| 5,327,029 A | 7/1994 | Ericson et al. | |
| 5,330,634 A | 7/1994 | Wong et al. | |
| 5,340,722 A | 8/1994 | Wolfbeis et al. | |
| 5,342,789 A | 8/1994 | Chick et al. | |
| 5,356,786 A | 10/1994 | Heller et al. | |
| 5,360,404 A | 11/1994 | Novacek et al. | |
| 5,372,427 A | 12/1994 | Padovani et al. | |
| 5,379,238 A | 1/1995 | Stark | |
| 5,384,547 A | 1/1995 | Lynk, Jr. et al. | |
| 5,390,671 A | 2/1995 | Lord et al. | |
| 5,391,250 A | 2/1995 | Cheney, II et al. | |
| 5,408,999 A | 4/1995 | Singh et al. | |
| 5,410,326 A | 4/1995 | Goldstein | |
| 5,411,647 A | 5/1995 | Johnson et al. | |
| 5,425,868 A | 6/1995 | Pedersen | |
| 5,429,602 A | 7/1995 | Hauser | |
| 5,431,160 A | 7/1995 | Wilkins | |
| 5,431,921 A | 7/1995 | Thombre | |
| 5,438,983 A | 8/1995 | Falcone | |
| 5,462,645 A | 10/1995 | Albery et al. | |
| 5,472,317 A | 12/1995 | Field et al. | |
| 5,489,414 A | 2/1996 | Schreiber et al. | |
| 5,497,772 A | 3/1996 | Schulman et al. | |
| 5,505,828 A | 4/1996 | Wong et al. | |
| 5,507,288 A | 4/1996 | Bocker et al. | |
| 5,509,410 A | 4/1996 | Hill et al. | |
| 5,514,718 A | 5/1996 | Lewis et al. | |
| 5,531,878 A | 7/1996 | Vadgama et al. | |
| 5,532,686 A | 7/1996 | Urbas et al. | |
| 5,552,997 A | 9/1996 | Massart | |
| 5,568,400 A | 10/1996 | Stark et al. | |
| 5,568,806 A | 10/1996 | Cheney, II et al. | |
| 5,569,186 A | 10/1996 | Lord et al. | |
| 5,582,184 A | 12/1996 | Erickson et al. | |
| 5,586,553 A | 12/1996 | Halili et al. | |
| 5,593,852 A | 1/1997 | Heller et al. | |
| 5,601,435 A | 2/1997 | Quy | |
| 5,609,575 A | 3/1997 | Larson et al. | |
| 5,628,310 A | 5/1997 | Rao et al. | |
| 5,628,890 A | 5/1997 | Carter et al. | |
| 5,634,468 A | 6/1997 | Platt et al. | |
| 5,653,239 A | 8/1997 | Pompei et al. | |
| 5,660,163 A | 8/1997 | Schulman et al. | |
| 5,665,222 A | 9/1997 | Heller et al. | |
| 5,707,502 A | 1/1998 | McCaffrey et al. | |
| 5,711,001 A | 1/1998 | Bussan et al. | |
| 5,711,861 A | 1/1998 | Ward et al. | |
| 5,724,030 A | 3/1998 | Urbas et al. | |
| 5,726,646 A | 3/1998 | Bane et al. | |
| 5,733,259 A | 3/1998 | Valcke et al. | |

(56) References Cited

U.S. PATENT DOCUMENTS

| | | |
|---|---|---|
| 5,735,285 A | 4/1998 | Albert et al. |
| 5,748,103 A | 5/1998 | Flach et al. |
| 5,749,907 A | 5/1998 | Mann |
| 5,772,586 A | 6/1998 | Heinonen et al. |
| 5,791,344 A | 8/1998 | Schulman et al. |
| 5,804,047 A | 9/1998 | Karube et al. |
| 5,820,551 A | 10/1998 | Hill et al. |
| 5,822,715 A | 10/1998 | Worthington et al. |
| 5,833,603 A | 11/1998 | Kovacs et al. |
| 5,842,189 A | 11/1998 | Keeler et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,918,603 A | 7/1999 | Brown |
| 5,919,141 A | 7/1999 | Money et al. |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,980,708 A | 11/1999 | Champagne et al. |
| 5,995,860 A | 11/1999 | Sun et al. |
| 6,001,067 A | 12/1999 | Shults et al. |
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,066,243 A | 5/2000 | Anderson et al. |
| 6,071,391 A | 6/2000 | Gotoh et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,130,623 A | 10/2000 | MacLellan et al. |
| 6,134,461 A | 10/2000 | Say et al. |
| 6,143,164 A | 11/2000 | Heller et al. |
| 6,144,837 A | 11/2000 | Quy |
| 6,144,871 A | 11/2000 | Saito et al. |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,248,067 B1 | 6/2001 | Causey, III et al. |
| 6,254,586 B1 | 7/2001 | Mann et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,299,347 B1 | 10/2001 | Pompei |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,314,317 B1 | 11/2001 | Willis |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,377,828 B1 | 4/2002 | Chaiken et al. |
| 6,377,894 B1 | 4/2002 | Deweese et al. |
| 6,379,301 B1 | 4/2002 | Worthington et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,478,736 B1 | 11/2002 | Mault |
| 6,484,046 B1 | 11/2002 | Say et al. |
| 6,493,069 B1 | 12/2002 | Nagashimada et al. |
| 6,496,729 B2 | 12/2002 | Thompson |
| 6,497,655 B1 | 12/2002 | Linberg et al. |
| 6,498,043 B1 | 12/2002 | Schulman et al. |
| 6,503,381 B1 | 1/2003 | Gotoh et al. |
| 6,510,344 B1 | 1/2003 | Halpern |
| 6,514,460 B1 | 2/2003 | Fendrock |
| 6,514,718 B2 | 2/2003 | Heller et al. |
| 6,520,326 B2 | 2/2003 | McIvor et al. |
| 6,540,891 B1 | 4/2003 | Stewart et al. |
| 6,544,212 B2 | 4/2003 | Galley et al. |
| 6,546,268 B1 | 4/2003 | Ishikawa et al. |
| 6,549,796 B2 | 4/2003 | Sohrab |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 * | 5/2003 | Heller .................. A61B 5/076 600/347 |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,545 B2 | 6/2003 | Knobbe et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulsen et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciurczak et al. |

(56) References Cited

U.S. PATENT DOCUMENTS

| | | | |
|---|---|---|---|
| 6,676,816 | B2 | 1/2004 | Mao et al. |
| 6,687,546 | B2 | 2/2004 | Lebel et al. |
| 6,689,056 | B1 | 2/2004 | Kilcoyne et al. |
| 6,694,191 | B2 | 2/2004 | Starkweather et al. |
| 6,695,860 | B1 | 2/2004 | Ward et al. |
| 6,698,269 | B2 | 3/2004 | Baber et al. |
| 6,702,857 | B2 | 3/2004 | Brauker et al. |
| 6,730,025 | B1 | 5/2004 | Platt |
| 6,730,200 | B1 | 5/2004 | Stewart et al. |
| 6,731,976 | B2 | 5/2004 | Penn et al. |
| 6,733,446 | B2 | 5/2004 | Lebel et al. |
| 6,735,183 | B2 | 5/2004 | O'Toole et al. |
| 6,736,957 | B1 | 5/2004 | Forrow et al. |
| 6,740,075 | B2 | 5/2004 | Lebel et al. |
| 6,740,518 | B1 | 5/2004 | Duong et al. |
| 6,741,877 | B1 | 5/2004 | Shults et al. |
| 6,746,582 | B2 | 6/2004 | Heller et al. |
| 6,749,740 | B2 | 6/2004 | Liamos et al. |
| 6,758,810 | B2 | 7/2004 | Lebel et al. |
| 6,764,581 | B1 | 7/2004 | Forrow et al. |
| 6,770,030 | B1 | 8/2004 | Schaupp et al. |
| 6,773,671 | B1 | 8/2004 | Lewis et al. |
| 6,789,195 | B1 | 9/2004 | Prihoda et al. |
| 6,790,178 | B1 | 9/2004 | Mault et al. |
| 6,804,558 | B2 | 10/2004 | Haller et al. |
| 6,809,653 | B1 | 10/2004 | Mann et al. |
| 6,810,290 | B2 | 10/2004 | Lebel et al. |
| 6,811,533 | B2 | 11/2004 | Lebel et al. |
| 6,811,534 | B2 | 11/2004 | Bowman, IV et al. |
| 6,813,519 | B2 | 11/2004 | Lebel et al. |
| 6,850,790 | B2 | 2/2005 | Berner et al. |
| 6,862,465 | B2 | 3/2005 | Shults et al. |
| 6,865,407 | B2 | 3/2005 | Kimball et al. |
| 6,873,268 | B2 | 3/2005 | Lebel et al. |
| 6,878,112 | B2 | 4/2005 | Linberg et al. |
| 6,881,551 | B2 | 4/2005 | Heller et al. |
| 6,882,940 | B2 | 4/2005 | Potts et al. |
| 6,892,085 | B2 | 5/2005 | McIvor et al. |
| 6,893,545 | B2 | 5/2005 | Gotoh et al. |
| 6,895,263 | B2 | 5/2005 | Shin et al. |
| 6,895,265 | B2 | 5/2005 | Silver |
| 6,923,763 | B1 | 8/2005 | Kovatchev et al. |
| 6,923,764 | B2 | 8/2005 | Aceti et al. |
| 6,931,327 | B2 | 8/2005 | Goode, Jr. et al. |
| 6,932,894 | B2 | 8/2005 | Mao et al. |
| 6,936,006 | B2 | 8/2005 | Sabra |
| 6,940,403 | B2 | 9/2005 | Kail, IV |
| 6,941,163 | B2 | 9/2005 | Ford et al. |
| 6,942,518 | B2 | 9/2005 | Liamos et al. |
| 6,950,708 | B2 | 9/2005 | Bowman, IV et al. |
| 6,958,705 | B2 | 10/2005 | Lebel et al. |
| 6,968,294 | B2 | 11/2005 | Gutta et al. |
| 6,971,274 | B2 | 12/2005 | Olin |
| 6,974,437 | B2 | 12/2005 | Lebel et al. |
| 6,983,176 | B2 | 1/2006 | Gardner et al. |
| 6,990,366 | B2 | 1/2006 | Say et al. |
| 6,997,907 | B2 | 2/2006 | Safabash et al. |
| 6,998,247 | B2 | 2/2006 | Monfre et al. |
| 6,999,854 | B2 | 2/2006 | Roth |
| 7,003,336 | B2 | 2/2006 | Holker et al. |
| 7,003,340 | B2 | 2/2006 | Say et al. |
| 7,003,341 | B2 | 2/2006 | Say et al. |
| 7,009,511 | B2 | 3/2006 | Mazar et al. |
| 7,015,817 | B2 | 3/2006 | Copley et al. |
| 7,016,713 | B2 | 3/2006 | Gardner et al. |
| 7,020,508 | B2 | 3/2006 | Stivoric et al. |
| 7,022,072 | B2 | 4/2006 | Fox et al. |
| 7,022,219 | B2 | 4/2006 | Mansouri et al. |
| 7,024,236 | B2 | 4/2006 | Ford et al. |
| 7,024,245 | B2 | 4/2006 | Lebel et al. |
| 7,025,425 | B2 | 4/2006 | Kovatchev et al. |
| 7,027,848 | B2 | 4/2006 | Robinson et al. |
| 7,027,931 | B1 | 4/2006 | Jones et al. |
| 7,029,444 | B2 | 4/2006 | Shin et al. |
| 7,041,068 | B2 | 5/2006 | Freeman et al. |
| 7,041,468 | B2 | 5/2006 | Drucker et al. |
| 7,043,305 | B2 | 5/2006 | Kenknight et al. |
| 7,046,153 | B2 | 5/2006 | Oja et al. |
| 7,052,483 | B2 | 5/2006 | Wojcik |
| 7,056,302 | B2 | 6/2006 | Douglas |
| 7,058,453 | B2 | 6/2006 | Nelson et al. |
| 7,060,031 | B2 | 6/2006 | Webb et al. |
| 7,074,307 | B2 | 7/2006 | Simpson et al. |
| 7,081,195 | B2 | 7/2006 | Simpson et al. |
| 7,082,334 | B2 | 7/2006 | Boute et al. |
| 7,092,891 | B2 | 8/2006 | Maus et al. |
| 7,098,803 | B2 | 8/2006 | Mann et al. |
| 7,108,778 | B2 | 9/2006 | Simpson et al. |
| 7,110,803 | B2 | 9/2006 | Shults et al. |
| 7,113,821 | B1 | 9/2006 | Sun et al. |
| 7,118,667 | B2 | 10/2006 | Lee |
| 7,123,950 | B2 | 10/2006 | Mannheimer |
| 7,125,382 | B2 | 10/2006 | Zhou et al. |
| 7,134,999 | B2 | 11/2006 | Brauker et al. |
| 7,136,689 | B2 | 11/2006 | Shults et al. |
| 7,153,265 | B2 | 12/2006 | Vachon |
| 7,155,290 | B2 | 12/2006 | Von Arx et al. |
| 7,167,818 | B2 | 1/2007 | Brown |
| 7,171,274 | B2 | 1/2007 | Starkweather et al. |
| 7,179,226 | B2 | 2/2007 | Crothall et al. |
| 7,190,988 | B2 | 3/2007 | Say et al. |
| 7,192,450 | B2 | 3/2007 | Brauker et al. |
| 7,198,606 | B2 | 4/2007 | Boecker et al. |
| 7,203,549 | B2 | 4/2007 | Schommer et al. |
| 7,207,974 | B2 | 4/2007 | Safabash et al. |
| 7,225,535 | B2 | 6/2007 | Feldman et al. |
| 7,226,442 | B2 | 6/2007 | Sheppard, Jr. et al. |
| 7,226,978 | B2 | 6/2007 | Tapsak et al. |
| 7,228,182 | B2 | 6/2007 | Healy et al. |
| 7,237,712 | B2 | 7/2007 | DeRocco et al. |
| 7,258,673 | B2 | 8/2007 | Racchini et al. |
| 7,267,665 | B2 | 9/2007 | Steil et al. |
| 7,276,029 | B2 | 10/2007 | Goode, Jr. et al. |
| 7,278,983 | B2 | 10/2007 | Ireland et al. |
| 7,286,894 | B1 | 10/2007 | Grant et al. |
| 7,295,867 | B2 | 11/2007 | Berner et al. |
| 7,299,082 | B2 | 11/2007 | Feldman et al. |
| 7,301,463 | B1 | 11/2007 | Paterno |
| 7,310,544 | B2 | 12/2007 | Brister et al. |
| 7,317,938 | B2 | 1/2008 | Lorenz et al. |
| 7,318,816 | B2 | 1/2008 | Bobroff et al. |
| 7,324,850 | B2 | 1/2008 | Persen et al. |
| 7,329,239 | B2 | 2/2008 | Safabash et al. |
| 7,335,294 | B2 | 2/2008 | Heller et al. |
| 7,347,819 | B2 | 3/2008 | Lebel et al. |
| 7,354,420 | B2 | 4/2008 | Steil et al. |
| 7,364,592 | B2 | 4/2008 | Carr-Brendel et al. |
| 7,366,556 | B2 | 4/2008 | Brister et al. |
| 7,379,765 | B2 | 5/2008 | Petisce et al. |
| 7,384,397 | B2 | 6/2008 | Zhang et al. |
| 7,387,010 | B2 | 6/2008 | Sunshine |
| 7,399,277 | B2 | 7/2008 | Saidara et al. |
| 7,402,153 | B2 | 7/2008 | Steil et al. |
| 7,404,796 | B2 | 7/2008 | Ginsberg |
| 7,419,573 | B2 | 9/2008 | Gundel |
| 7,424,318 | B2 | 9/2008 | Brister et al. |
| 7,460,898 | B2 | 12/2008 | Brister et al. |
| 7,467,003 | B2 | 12/2008 | Brister et al. |
| 7,468,125 | B2 | 12/2008 | Kraft et al. |
| 7,471,972 | B2 | 12/2008 | Rhodes et al. |
| 7,474,992 | B2 | 1/2009 | Ariyur |
| 7,492,254 | B2 | 2/2009 | Bandy et al. |
| 7,494,465 | B2 | 2/2009 | Brister et al. |
| 7,497,827 | B2 | 3/2009 | Brister et al. |
| 7,519,408 | B2 | 4/2009 | Rasdal et al. |
| 7,547,281 | B2 | 6/2009 | Hayes et al. |
| 7,565,197 | B2 | 7/2009 | Haubrich et al. |
| 7,569,030 | B2 | 8/2009 | Lebel et al. |
| 7,574,266 | B2 | 8/2009 | Dudding et al. |
| 7,583,990 | B2 | 9/2009 | Goode, Jr. et al. |
| 7,591,801 | B2 | 9/2009 | Brauker et al. |
| 7,599,726 | B2 | 10/2009 | Goode, Jr. et al. |
| 7,602,310 | B2 | 10/2009 | Mann et al. |
| 7,604,178 | B2 | 10/2009 | Stewart |

(56) References Cited

U.S. PATENT DOCUMENTS

| | | |
|---|---|---|
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,643,798 B2 | 1/2010 | Ljung |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,668,596 B2 | 2/2010 | Von Arx et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,736,310 B2 | 6/2010 | Taub |
| 7,741,734 B2 | 6/2010 | Joannopoulos et al. |
| 7,766,829 B2 | 8/2010 | Sloan et al. |
| 7,768,386 B2 * | 8/2010 | Hayter .................. G16Z 99/00 340/517 |
| 7,768,387 B2 | 8/2010 | Fennell |
| 7,771,352 B2 | 8/2010 | Shults et al. |
| 7,774,145 B2 | 8/2010 | Brauker et al. |
| 7,778,680 B2 | 8/2010 | Goode, Jr. et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,811,231 B2 | 10/2010 | Jin et al. |
| 7,813,809 B2 | 10/2010 | Strother et al. |
| 7,826,382 B2 | 11/2010 | Sicurello et al. |
| 7,826,981 B2 | 11/2010 | Goode, Jr. et al. |
| 7,831,310 B2 | 11/2010 | Lebel et al. |
| 7,835,925 B2 | 11/2010 | Roe et al. |
| 7,860,574 B2 | 12/2010 | Von Arx et al. |
| 7,882,611 B2 | 2/2011 | Shah et al. |
| 7,889,069 B2 | 2/2011 | Fifolt et al. |
| 7,899,511 B2 | 3/2011 | Shults et al. |
| 7,899,545 B2 | 3/2011 | John |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,920,906 B2 | 4/2011 | Goode, Jr. et al. |
| 7,920,907 B2 | 4/2011 | McGarraugh et al. |
| 7,928,850 B2 | 4/2011 | Hayter et al. |
| 7,938,797 B2 | 5/2011 | Estes |
| 7,941,200 B2 | 5/2011 | Weinert et al. |
| 7,946,985 B2 | 5/2011 | Mastrototaro et al. |
| 7,955,258 B2 | 6/2011 | Goscha et al. |
| 7,970,448 B2 | 6/2011 | Shults et al. |
| 7,972,296 B2 | 7/2011 | Braig et al. |
| 7,974,672 B2 | 7/2011 | Shults et al. |
| 7,976,466 B2 | 7/2011 | Ward et al. |
| 7,978,063 B2 | 7/2011 | Baldus et al. |
| 7,999,674 B2 | 8/2011 | Kamen |
| 8,010,174 B2 | 8/2011 | Goode, Jr. et al. |
| 8,010,256 B2 | 8/2011 | Oowada |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B1 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,551 B1 | 3/2012 | Cosatto et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,150,321 B2 | 4/2012 | Winter et al. |
| 8,150,516 B2 | 4/2012 | Levine et al. |
| 8,179,266 B2 | 5/2012 | Hermle |
| 8,192,394 B2 | 6/2012 | Estes et al. |
| 8,216,138 B1 | 7/2012 | McGarraugh |
| 8,255,026 B1 | 8/2012 | Al-Ali |
| 8,282,549 B2 | 10/2012 | Brauker et al. |
| 8,374,668 B1 | 2/2013 | Hayter et al. |
| 8,461,985 B2 | 6/2013 | Fennell et al. |
| 8,597,570 B2 | 12/2013 | Terashima et al. |
| 8,710,993 B2 | 4/2014 | Hayter et al. |
| 8,845,536 B2 | 9/2014 | Brauker et al. |
| 9,974,472 B2 | 5/2018 | Hayter et al. |
| 10,111,608 B2 | 10/2018 | Hayter |
| 10,398,363 B2 | 9/2019 | Hayter et al. |
| 11,039,767 B2 | 6/2021 | Hayter |
| 2001/0037366 A1 | 11/2001 | Webb et al. |
| 2002/0019022 A1 | 2/2002 | Dunn et al. |
| 2002/0019612 A1 | 2/2002 | Watanabe et al. |
| 2002/0042090 A1 | 4/2002 | Heller et al. |
| 2002/0054320 A1 | 5/2002 | Ogino |
| 2002/0068860 A1 | 6/2002 | Clark |
| 2002/0072784 A1 | 6/2002 | Sheppard et al. |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0120186 A1 | 8/2002 | Keimel |
| 2002/0128594 A1 | 9/2002 | Das et al. |
| 2002/0147135 A1 | 10/2002 | Schnell |
| 2002/0161288 A1 | 10/2002 | Shin et al. |
| 2002/0169439 A1 | 11/2002 | Flaherty |
| 2002/0169635 A1 | 11/2002 | Shillingburg |
| 2003/0004403 A1 | 1/2003 | Drinan et al. |
| 2003/0010089 A1 | 1/2003 | Holmes |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0028184 A1 | 2/2003 | Lebel et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0055380 A1 | 3/2003 | Flaherty |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0076082 A1 | 4/2003 | Morgan et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0147515 A1 | 8/2003 | Kai et al. |
| 2003/0159945 A1 | 8/2003 | Miyazaki et al. |

(56) References Cited

U.S. PATENT DOCUMENTS

| | | |
|---|---|---|
| 2003/0167035 A1 | 9/2003 | Flaherty et al. |
| 2003/0168338 A1 | 9/2003 | Gao et al. |
| 2003/0169800 A1 | 9/2003 | Pompei |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0211617 A1 | 11/2003 | Jones |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2003/0225361 A1 | 12/2003 | Sabra |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0015131 A1 | 1/2004 | Flaherty et al. |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0063435 A1 | 4/2004 | Sakamoto et al. |
| 2004/0064068 A1 | 4/2004 | DeNUZZIO et al. |
| 2004/0064088 A1 | 4/2004 | Gorman et al. |
| 2004/0064096 A1 | 4/2004 | Flaherty et al. |
| 2004/0099529 A1 | 5/2004 | Mao et al. |
| 2004/0106858 A1 | 6/2004 | Say et al. |
| 2004/0117204 A1 | 6/2004 | Mazar et al. |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0135684 A1 | 7/2004 | Steinthal et al. |
| 2004/0138588 A1 | 7/2004 | Saikley et al. |
| 2004/0142483 A1 | 7/2004 | Genshaw |
| 2004/0146909 A1 | 7/2004 | Duong et al. |
| 2004/0147872 A1 | 7/2004 | Thompson |
| 2004/0152622 A1 | 8/2004 | Keith et al. |
| 2004/0153032 A1 | 8/2004 | Garribotto et al. |
| 2004/0158167 A1 | 8/2004 | Smith et al. |
| 2004/0167464 A1 | 8/2004 | Ireland et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0219664 A1 | 11/2004 | Heller et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0017864 A1 | 1/2005 | Tsoukalis |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027182 A1 | 2/2005 | Siddiqui et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode et al. |
| 2005/0049179 A1 | 3/2005 | Davidson et al. |
| 2005/0070774 A1 | 3/2005 | Addison et al. |
| 2005/0070777 A1 | 3/2005 | Cho et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0112169 A1 | 5/2005 | Brauker et al. |
| 2005/0113648 A1 | 5/2005 | Yang et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0137530 A1 | 6/2005 | Campbell et al. |
| 2005/0143635 A1 | 6/2005 | Kamath et al. |
| 2005/0148003 A1 | 7/2005 | Keith et al. |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187442 A1 | 8/2005 | Cho et al. |
| 2005/0187720 A1 | 8/2005 | Goode et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0244811 A1 | 11/2005 | Soundarrajan et al. |
| 2005/0245795 A1 | 11/2005 | Goode et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0272985 A1 | 12/2005 | Kotulla et al. |
| 2005/0277164 A1 | 12/2005 | Drucker et al. |
| 2005/0277912 A1 | 12/2005 | John |
| 2005/0283208 A1 | 12/2005 | Von Arx et al. |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0025663 A1 | 2/2006 | Talbot et al. |
| 2006/0029177 A1 | 2/2006 | Cranford et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0056487 A1 | 3/2006 | Kuroda et al. |

(56) References Cited

U.S. PATENT DOCUMENTS

| | | |
|---|---|---|
| 2006/0058588 A1 | 3/2006 | Zdeblick |
| 2006/0079740 A1 | 4/2006 | Silver et al. |
| 2006/0091006 A1 | 5/2006 | Wang et al. |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0156796 A1 | 7/2006 | Burke et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189863 A1 | 8/2006 | Peyser et al. |
| 2006/0193375 A1 | 8/2006 | Lee |
| 2006/0202805 A1 | 9/2006 | Schulman et al. |
| 2006/0211072 A1 | 9/2006 | Ryan et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0229512 A1 | 10/2006 | Petisce et al. |
| 2006/0247508 A1 | 11/2006 | Fennell |
| 2006/0247710 A1 | 11/2006 | Goetz et al. |
| 2006/0247985 A1 | 11/2006 | Liamos et al. |
| 2006/0253296 A1 | 11/2006 | Liisberg et al. |
| 2006/0258929 A1 | 11/2006 | Goode et al. |
| 2006/0272652 A1 | 12/2006 | Stocker et al. |
| 2006/0276771 A1 | 12/2006 | Galley et al. |
| 2006/0281985 A1 | 12/2006 | Ward et al. |
| 2006/0287691 A1 | 12/2006 | Drew |
| 2006/0290496 A1 | 12/2006 | Peeters |
| 2006/0293607 A1 | 12/2006 | Alt et al. |
| 2007/0000163 A1 | 1/2007 | Buckner |
| 2007/0000273 A1 | 1/2007 | Sanders |
| 2007/0002443 A1 | 1/2007 | Toyama |
| 2007/0010950 A1 | 1/2007 | Abensour et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0032706 A1 | 2/2007 | Kamath et al. |
| 2007/0032717 A1 | 2/2007 | Brister et al. |
| 2007/0033074 A1 | 2/2007 | Nitzan et al. |
| 2007/0038044 A1 | 2/2007 | Dobbles et al. |
| 2007/0055799 A1 | 3/2007 | Koehler et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0078818 A1 | 4/2007 | Zivitz et al. |
| 2007/0093786 A1 | 4/2007 | Goldsmith et al. |
| 2007/0094216 A1 | 4/2007 | Mathias et al. |
| 2007/0095661 A1 | 5/2007 | Wang et al. |
| 2007/0100222 A1 | 5/2007 | Mastrototaro et al. |
| 2007/0106135 A1 | 5/2007 | Sloan et al. |
| 2007/0108048 A1 | 5/2007 | Wang et al. |
| 2007/0118405 A1 | 5/2007 | Campbell et al. |
| 2007/0124002 A1 | 5/2007 | Estes et al. |
| 2007/0149875 A1 | 6/2007 | Ouyang et al. |
| 2007/0151869 A1 | 7/2007 | Heller et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0191702 A1 | 8/2007 | Yodfat et al. |
| 2007/0199818 A1 | 8/2007 | Petyt et al. |
| 2007/0203407 A1 | 8/2007 | Hoss et al. |
| 2007/0203966 A1 | 8/2007 | Brauker et al. |
| 2007/0208244 A1 | 9/2007 | Brauker et al. |
| 2007/0208246 A1 | 9/2007 | Brauker et al. |
| 2007/0213657 A1 | 9/2007 | Jennewine et al. |
| 2007/0228071 A1 | 10/2007 | Kamen et al. |
| 2007/0232878 A1 | 10/2007 | Kovatchev et al. |
| 2007/0232880 A1 | 10/2007 | Siddiqui et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255116 A1 | 11/2007 | Mehta et al. |
| 2007/0255321 A1 | 11/2007 | Gerber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0270672 A1 | 11/2007 | Hayter |
| 2007/0271285 A1 | 11/2007 | Eichorn et al. |
| 2007/0282299 A1 | 12/2007 | Hellwig |
| 2007/0285238 A1 | 12/2007 | Batra |
| 2007/0299617 A1 | 12/2007 | Willis |
| 2008/0004515 A1 | 1/2008 | Jennewine |
| 2008/0004601 A1 | 1/2008 | Jennewine et al. |
| 2008/0009692 A1 | 1/2008 | Stafford |
| 2008/0017522 A1 | 1/2008 | Heller et al. |
| 2008/0018433 A1 | 1/2008 | Pitt-Pladdy |
| 2008/0021436 A1 | 1/2008 | Wolpert et al. |
| 2008/0021666 A1 | 1/2008 | Goode et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0064943 A1 | 3/2008 | Talbot et al. |
| 2008/0066305 A1 | 3/2008 | Wang et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0097289 A1 | 4/2008 | Steil et al. |
| 2008/0102441 A1 | 5/2008 | Chen et al. |
| 2008/0103447 A1 | 5/2008 | Reggiardo et al. |
| 2008/0108942 A1 | 5/2008 | Brister et al. |
| 2008/0114228 A1 | 5/2008 | McCluskey et al. |
| 2008/0119705 A1 | 5/2008 | Patel et al. |
| 2008/0119710 A1 | 5/2008 | Reggiardo et al. |
| 2008/0139910 A1 | 6/2008 | Mastrototaro et al. |
| 2008/0148873 A1 | 6/2008 | Wang |
| 2008/0154513 A1 | 6/2008 | Kovatchev et al. |
| 2008/0161666 A1 | 7/2008 | Feldman et al. |
| 2008/0161707 A1 | 7/2008 | Farringdon et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0182537 A1 | 7/2008 | Manku et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |

(56) References Cited

U.S. PATENT DOCUMENTS

| | | |
|---|---|---|
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0208113 A1 | 8/2008 | Damiano et al. |
| 2008/0214900 A1 | 9/2008 | Fennell et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234663 A1 | 9/2008 | Yodfat et al. |
| 2008/0234943 A1 | 9/2008 | Ray et al. |
| 2008/0234992 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262304 A1 | 10/2008 | Nisani et al. |
| 2008/0262469 A1 | 10/2008 | Brister et al. |
| 2008/0267823 A1 | 10/2008 | Wang et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0281179 A1 | 11/2008 | Fennell et al. |
| 2008/0287761 A1 | 11/2008 | Hayter et al. |
| 2008/0287762 A1 | 11/2008 | Hayter et al. |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter et al. |
| 2008/0288204 A1 | 11/2008 | Hayter et al. |
| 2008/0294024 A1 | 11/2008 | Cosentino et al. |
| 2008/0296155 A1 | 12/2008 | Shults et al. |
| 2008/0300572 A1 | 12/2008 | Rankers et al. |
| 2008/0300919 A1 | 12/2008 | Charlton et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter et al. |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319085 A1 | 12/2008 | Wright et al. |
| 2008/0319279 A1 | 12/2008 | Ramsay et al. |
| 2009/0001923 A1 | 1/2009 | Gallegos-Lopez et al. |
| 2009/0005665 A1 | 1/2009 | Hayter et al. |
| 2009/0005666 A1 | 1/2009 | Shin et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0023222 A1 | 1/2009 | Wu et al. |
| 2009/0027040 A1 | 1/2009 | Kermani et al. |
| 2009/0030293 A1 | 1/2009 | Cooper et al. |
| 2009/0030294 A1 | 1/2009 | Petisce et al. |
| 2009/0030641 A1* | 1/2009 | Fjield .................... G01D 3/036 702/104 |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054737 A1 | 2/2009 | Magar et al. |
| 2009/0054745 A1 | 2/2009 | Jennewine |
| 2009/0054747 A1 | 2/2009 | Fennell |
| 2009/0054748 A1 | 2/2009 | Feldman |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | Van Antwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0088614 A1 | 4/2009 | Taub |
| 2009/0093687 A1 | 4/2009 | Telfort et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0112478 A1 | 4/2009 | Mueller, Jr. et al. |
| 2009/0118604 A1 | 5/2009 | Phan et al. |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0209904 A1 | 8/2009 | Peeters |

(56) References Cited

U.S. PATENT DOCUMENTS

| | | |
|---|---|---|
| 2009/0216100 A1 | 8/2009 | Ebner et al. |
| 2009/0216103 A1 | 8/2009 | Brister et al. |
| 2009/0227855 A1 | 9/2009 | Hill et al. |
| 2009/0234200 A1 | 9/2009 | Husheer |
| 2009/0236237 A1 | 9/2009 | Shinno et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0240440 A1 | 9/2009 | Shurabura et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0253973 A1 | 10/2009 | Bashan et al. |
| 2009/0259118 A1 | 10/2009 | Feldman et al. |
| 2009/0267765 A1 | 10/2009 | Greene et al. |
| 2009/0275815 A1* | 11/2009 | Bickoff .............. A61B 5/14865 600/345 |
| 2009/0276017 A1 | 11/2009 | Achenbach et al. |
| 2009/0287073 A1 | 11/2009 | Boock et al. |
| 2009/0287074 A1 | 11/2009 | Shults et al. |
| 2009/0289796 A1 | 11/2009 | Blumberg, Jr. |
| 2009/0291634 A1 | 11/2009 | Saarisalo |
| 2009/0292188 A1 | 11/2009 | Hoss et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2009/0318792 A1 | 12/2009 | Fennell et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049016 A1 | 2/2010 | Aronowitz et al. |
| 2010/0049024 A1 | 2/2010 | Saint et al. |
| 2010/0056992 A1 | 3/2010 | Hayter |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063373 A1 | 3/2010 | Kamath et al. |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121169 A1 | 5/2010 | Petisce et al. |
| 2010/0128754 A1 | 5/2010 | Jetter et al. |
| 2010/0141656 A1 | 6/2010 | Krieftewirth |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0185175 A1 | 7/2010 | Kamen et al. |
| 2010/0190435 A1 | 7/2010 | Cook et al. |
| 2010/0191082 A1 | 7/2010 | Brister et al. |
| 2010/0191085 A1 | 7/2010 | Budiman |
| 2010/0191472 A1 | 7/2010 | Doniger et al. |
| 2010/0198034 A1 | 8/2010 | Thomas et al. |
| 2010/0198142 A1 | 8/2010 | Sloan et al. |
| 2010/0198314 A1 | 8/2010 | Wei |
| 2010/0204557 A1 | 8/2010 | Kiaie et al. |
| 2010/0213080 A1 | 8/2010 | Celentano et al. |
| 2010/0234710 A1 | 9/2010 | Budiman et al. |
| 2010/0240975 A1 | 9/2010 | Goode, Jr. et al. |
| 2010/0253361 A1 | 10/2010 | Nakamura et al. |
| 2010/0268475 A1 | 10/2010 | Kusumoto |
| 2010/0274111 A1 | 10/2010 | Say et al. |
| 2010/0274515 A1 | 10/2010 | Hoss et al. |
| 2010/0277342 A1 | 11/2010 | Sicurello et al. |
| 2010/0312176 A1 | 12/2010 | Lauer et al. |
| 2010/0313105 A1 | 12/2010 | Nekoomaram et al. |
| 2010/0317958 A1 | 12/2010 | Beck et al. |
| 2010/0324392 A1 | 12/2010 | Yee et al. |
| 2010/0325868 A1 | 12/2010 | Wang et al. |
| 2010/0326842 A1 | 12/2010 | Mazza et al. |
| 2011/0004276 A1 | 1/2011 | Blair et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0058485 A1 | 3/2011 | Sloan |
| 2011/0077490 A1 | 3/2011 | Simpson et al. |
| 2011/0077494 A1 | 3/2011 | Doniger et al. |
| 2011/0081726 A1 | 4/2011 | Berman |
| 2011/0105873 A1* | 5/2011 | Feldman ............ A61B 5/14546 600/365 |
| 2011/0112696 A1 | 5/2011 | Yodfat et al. |
| 2011/0148905 A1 | 6/2011 | Simmons et al. |
| 2011/0152637 A1 | 6/2011 | Kateraas et al. |
| 2011/0152658 A1* | 6/2011 | Peyser .................. A61B 5/01 600/365 |
| 2011/0174638 A1 | 7/2011 | Katsuki |
| 2011/0184265 A1 | 7/2011 | Hayter |
| 2011/0193704 A1 | 8/2011 | Harper et al. |
| 2011/0208027 A1 | 8/2011 | Wagner et al. |
| 2011/0210830 A1 | 9/2011 | Talty et al. |
| 2011/0213225 A1 | 9/2011 | Bernstein et al. |
| 2011/0257495 A1 | 10/2011 | Hoss et al. |
| 2011/0257895 A1 | 10/2011 | Brauker et al. |
| 2011/0287528 A1 | 11/2011 | Fern et al. |
| 2011/0289497 A1 | 11/2011 | Kiaie et al. |
| 2011/0320130 A1 | 12/2011 | Valdes et al. |
| 2011/0320167 A1 | 12/2011 | Budiman |
| 2012/0028283 A1 | 2/2012 | Hoss et al. |
| 2012/0078071 A1 | 3/2012 | Bohm et al. |
| 2012/0084053 A1 | 4/2012 | Yuen et al. |
| 2012/0108934 A1 | 5/2012 | Valdes et al. |
| 2012/0150005 A1 | 6/2012 | Hoss et al. |
| 2012/0157801 A1 | 6/2012 | Hoss et al. |
| 2012/0161793 A1 | 6/2012 | Satake et al. |
| 2012/0161959 A1 | 6/2012 | Palmer et al. |
| 2012/0165626 A1 | 6/2012 | Irina et al. |
| 2012/0165635 A1* | 6/2012 | Radhakrishnan .. A61B 5/14532 600/347 |
| 2012/0165640 A1 | 6/2012 | Galley et al. |
| 2012/0173200 A1 | 7/2012 | Breton et al. |
| 2012/0233679 A1 | 9/2012 | Shedrinsky |
| 2012/0238851 A1 | 9/2012 | Kamen et al. |
| 2012/0250610 A1 | 10/2012 | Budampati et al. |
| 2012/0255875 A1 | 10/2012 | Vicente et al. |
| 2012/0309302 A1 | 12/2012 | Buhot |
| 2012/0313785 A1 | 12/2012 | Hanson et al. |

(56) References Cited

U.S. PATENT DOCUMENTS

| | | |
|---|---|---|
| 2013/0035575 A1 | 2/2013 | Mayou et al. |
| 2013/0235166 A1 | 9/2013 | Jones et al. |
| 2020/0029871 A1 | 1/2020 | Hayter et al. |

FOREIGN PATENT DOCUMENTS

| | | |
|---|---|---|
| CA | 2413148 C | 8/2010 |
| CA | 2766339 A1 | 1/2011 |
| DE | 4401400 A1 | 7/1995 |
| EP | 0098592 A2 | 1/1984 |
| EP | 0127958 A2 | 12/1984 |
| EP | 0320109 A1 | 6/1989 |
| EP | 0353328 A1 | 2/1990 |
| EP | 0390390 A1 | 10/1990 |
| EP | 0396788 A1 | 11/1990 |
| EP | 0355328 B1 | 6/1994 |
| EP | 0286118 B1 | 1/1995 |
| EP | 0678308 A1 | 10/1995 |
| EP | 0724859 A1 | 8/1996 |
| EP | 0678308 B1 | 5/2000 |
| EP | 1048264 A1 | 11/2000 |
| EP | 1077634 A1 | 2/2001 |
| EP | 1292218 A1 | 3/2003 |
| EP | 1077634 B1 | 7/2003 |
| EP | 1448489 A1 | 8/2004 |
| EP | 1568309 A1 | 8/2005 |
| EP | 1666091 A2 | 6/2006 |
| EP | 1681992 A2 | 7/2006 |
| EP | 1703697 A1 | 9/2006 |
| EP | 1704893 A1 | 9/2006 |
| EP | 1897487 A1 | 3/2008 |
| EP | 1897488 A1 | 3/2008 |
| EP | 1897492 A2 | 3/2008 |
| EP | 1971396 A1 | 9/2008 |
| EP | 1897487 B1 | 11/2009 |
| EP | 1897492 B1 | 11/2009 |
| EP | 2113864 A2 | 11/2009 |
| EP | 1897488 B1 | 12/2009 |
| EP | 2153382 A1 | 2/2010 |
| EP | 1681992 B1 | 4/2010 |
| EP | 2201969 A1 | 6/2010 |
| EP | 1448489 B1 | 8/2010 |
| EP | 1971396 B1 | 8/2010 |
| EP | 2284773 A2 | 2/2011 |
| EP | 2201969 B1 | 3/2011 |
| EP | 2153382 B1 | 2/2012 |
| EP | 2284773 B1 | 2/2012 |
| EP | 2450699 A1 | 5/2012 |
| EP | 2498196 A2 | 9/2012 |
| EP | 2939158 B1 | 3/2022 |
| GB | 2409951 A | 7/2005 |
| JP | 5353991 B2 | 11/2013 |
| WO | WO-9306237 A1 | 4/1993 |
| WO | WO-9625089 A1 | 8/1996 |
| WO | WO-9635370 A1 | 11/1996 |
| WO | WO 97/18639 A1 | 5/1997 |
| WO | WO-9733513 A1 | 9/1997 |
| WO | WO-9835053 A2 | 8/1998 |
| WO | WO-9956613 A1 | 11/1999 |
| WO | WO-0019887 A1 | 4/2000 |
| WO | WO-0049940 A2 | 8/2000 |
| WO | WO-0059370 A1 | 10/2000 |
| WO | WO-0074753 A1 | 12/2000 |
| WO | WO-0078992 A2 | 12/2000 |
| WO | WO-0152935 A1 | 7/2001 |
| WO | WO-0154753 A2 | 8/2001 |
| WO | WO-0216905 A2 | 2/2002 |
| WO | WO-02058537 A2 | 8/2002 |
| WO | WO-03076893 A2 | 9/2003 |
| WO | WO-03082091 A2 | 10/2003 |
| WO | WO-03085372 A2 | 10/2003 |
| WO | WO-2004047445 A1 | 6/2004 |
| WO | WO-2004061420 A2 | 7/2004 |
| WO | WO-2005010756 A2 | 2/2005 |
| WO | WO-2005040404 A1 | 5/2005 |
| WO | WO-2005041766 A1 | 5/2005 |
| WO | WO-2005045744 A1 | 5/2005 |
| WO | WO-2005065538 A2 | 7/2005 |
| WO | WO-2005089103 A2 | 9/2005 |
| WO | WO-2005119238 A1 | 12/2005 |
| WO | WO-2005121785 A2 | 12/2005 |
| WO | WO-2006024671 A1 | 3/2006 |
| WO | WO-2006032653 A2 | 3/2006 |
| WO | WO-2006051466 A1 | 5/2006 |
| WO | WO-2006064397 A2 | 6/2006 |
| WO | WO-2006079114 A2 | 7/2006 |
| WO | WO-2006079867 A1 | 8/2006 |
| WO | WO-2006118947 A2 | 11/2006 |
| WO | WO-2006124099 A2 | 11/2006 |
| WO | WO-2007007459 A1 | 1/2007 |
| WO | WO-2007016399 A2 | 2/2007 |
| WO | WO-2007027788 A2 | 3/2007 |
| WO | WO-2007041069 A2 | 4/2007 |
| WO | WO-2007041070 A2 | 4/2007 |
| WO | WO-2007041248 A2 | 4/2007 |
| WO | WO-2007053832 A2 | 5/2007 |
| WO | WO-2007056638 A2 | 5/2007 |
| WO | WO-2007097754 A1 | 8/2007 |
| WO | WO-2007101223 A2 | 9/2007 |
| WO | WO-2007120363 A2 | 10/2007 |
| WO | WO-2007126444 A2 | 11/2007 |
| WO | WO-2007143225 A2 | 12/2007 |
| WO | WO-2008005124 A2 | 1/2008 |
| WO | WO-2008021913 A2 | 2/2008 |
| WO | WO-2008042760 A2 | 4/2008 |
| WO | WO 2008/051924 A1 | 5/2008 |
| WO | WO-2008076574 A2 | 6/2008 |
| WO | WO-2008086541 A2 | 7/2008 |
| WO | WO-2008128210 A1 | 10/2008 |
| WO | WO-2008130896 A1 | 10/2008 |
| WO | WO-2008130897 A2 | 10/2008 |
| WO | WO-2008130898 A1 | 10/2008 |
| WO | WO 2008/143943 A1 | 11/2008 |
| WO | WO-2008151452 A1 | 12/2008 |
| WO | WO-2009018058 A1 | 2/2009 |
| WO | WO-2009049252 A1 | 4/2009 |
| WO | WO-2009086216 A1 | 7/2009 |
| WO | WO-2009097597 A2 | 8/2009 |
| WO | 2010040090 A2 | 4/2010 |
| WO | WO-2010077329 A1 | 7/2010 |
| WO | WO-2011022418 A2 | 2/2011 |
| WO | WO 2013/019225 A1 | 2/2013 |
| WO | WO-2014070456 A1 | 5/2014 |

OTHER PUBLICATIONS

Decision to Grant in counterpart European application No. EP 19155366.8 dated Aug. 4, 2022 (2 pages).
Extended European Search Report in counterpart European application No. EP 12800721.8 dated Dec. 4, 2014 (8 pages).
Decision to Grant in counterpart European application No. EP 12800721.8 dated Jan. 10, 2019 (2 pages).
Extended European Search Report in counterpart European application No. EP 22179316.9 dated Dec. 22, 2022 (10 pages).
International Search Report and Written Opinion of the International Searching Authority directed to related International Patent Application No. PCT/US2012/43012, dated Nov. 30, 2012; 13 pages.
Klonoff, David C., M.D., F.A.C.P., "Continuous Glucose Monitoring, Roadmap for 21st Century Diabetes Therapy," Diabetes Care, vol. 28, No. 5, May 2005; pp. 1231-1239.
Klonoff, David, M.D., F.A.C.P., "A Review of Continuous Glucose Monitoring Technology," Diabetes Tech. & Therapeutics, vol. 7, No. 5, 2005; 6 pages.
Townsend, Kevin, "Getting Started with Bluetooth Low Energy," Book description for preview version, May 2014; 3 pages; available at: https://www.oreilly.com.
Wikipedia, "Blood Glucose Monitoring," Sep. 8, 2004; 6 pages; available at: https://https://en.wikipedia.org/wiki/Blood_glucose_monitoring.
Document D4a to the Evidence List presented in the Notice of Opposition to EP3556285, *Abbott Diabetes Care, Inc.* v. *Dexcom,*

(56) References Cited

OTHER PUBLICATIONS

*Inc.*, filed May 6, 2023, Lecture notes from the ENSC 388 Engineering Thermodynamics and Heat Transfer course at Simon Fraser University, Canada given by Dr Majid Bahrami, retrieved from https://www.sfu.ca/~mbahrami/ensc388.html.
Document D4b to the Evidence List presented in the Notice of Opposition to EP3556285, *Abbott Diabetes Care, Inc. v. Dexcom, Inc.*, filed May 6, 2023, Screenshot of the Adobe Acrobat Reader metadata for D4a showing that the date D4a was last modified was Nov. 5, 2009.
Document D5 to the Evidence List presented in the Notice of Opposition to EP3556285, *Abbott Diabetes Care, Inc. v. Dexcom, Inc.*, filed May 6, 2023, Pennes H. H. "Analysis of tissue and arterial blood temperatures in the resting human forearm". J Appl Physiol. Aug. 1948; vol. 1, No. 2: pp. 93-122.
Document D6 to the Evidence List presented in the Notice of Opposition to EP3556285, *Abbott Diabetes Care, Inc. v. Dexcom, Inc.*, filed May 6, 2023, Saxena V. P. and Singh R., "Unsteady state radial heat flow in the outer layers of spherical regions of human or animal body", J nanabha, vol. 34, 2004, pp. 47-54.
Document D7 to the Evidence List presented in the Notice of Opposition to EP3556285, *Abbott Diabetes Care, Inc. v. Dexcom, Inc.*, filed May 6, 2023, Gurung, D. "Thermoregulation Through Skin at Low Atmospheric Temperatures". Kathmandu University Journal of Science, Engineering and Technology, vol. 5, No. 1, Jan. 2009, pp. 14-22.
Document D8 to the Evidence List presented in the Notice of Opposition to EP3556285, *Abbott Diabetes Care, Inc. v. Dexcom, Inc.*, filed May 6, 2023, Saxena VP and Arya D. "Steady-state Heat Distribution in Epidermis, Dermis and Subdermal Tissues". J Theor Biol. Apr. 7, 1981; 89(3): 423-32.
Document D9 to the Evidence List presented in the Notice of Opposition to EP3556285, *Abbott Diabetes Care, Inc. v. Dexcom, Inc.*, filed May 6, 2023, Saxena V. P. "Effect of blood flow on temperature distribution in human skin and sub dermal tissues", 9th National Conference, Fluid Mechanics and Fluid Power, Dec. 1979, vol. 2, pp. 156-161.
Document D10 to the Evidence List presented in the Notice of Opposition to EP3556285, *Abbott Diabetes Care, Inc. v. Dexcom, Inc.*, filed May 6, 2023, Khanday, M.A., Saxena, V.P. "Mathematical estimation of physiological disturbances in human dermal parts at extreme conditions: One dimensional steady state case". Analysis in Theory and Applications. Vol. 25, No. 4, 2009, pp. 325-332.
Document D11 to the Evidence List presented in the Notice of Opposition to EP3556285, *Abbott Diabetes Care, Inc. v. Dexcom, Inc.*, filed May 6, 2023, Lenhardt R, Sessler DI, "Estimation of mean body temperature from mean skin and core temperature". Anesthesiology. Dec. 2006; 105(6):1117-21.
Document D12 to the Evidence List presented in the Notice of Opposition to EP3556285, *Abbott Diabetes Care, Inc. v. Dexcom, Inc.*, filed May 6, 2023, Burton AC., "Human Calorimetry: The average temperature of the tissues of the body". Journal of Nutrition. Mar. 1935, vol. 9, No. 3, pp. 261-280.
Document D13 to the Evidence List presented in the Notice of Opposition to EP3556285, *Abbott Diabetes Care, Inc. v. Dexcom, Inc.*, filed May 6, 2023, Yildirim E.D. "A mathematical model of the human thermal system", Master's thesis, Graduate School of Engineering and Sciences of Izmir Institute of Technology, 2005.
Document D14 to the Evidence List presented in the Notice of Opposition to EP3556285, *Abbott Diabetes Care, Inc. v. Dexcom, Inc.*, filed May 6, 2023, V.P. Saxena, K.R. Pardasani and p. M. Saxena, "Exact solution to temperature distribution problems in spherical tissue layers", Ganita Sandesh, 1991, vol. 5, No. 2, pp. 72-78.
Document D15 to the Evidence List presented in the Notice of Opposition to EP3556285, *Abbott Diabetes Care, Inc. v. Dexcom, Inc.*, filed May 6, 2023, V.P Saxena and D. Arya, "Variational finite element approach to heat distribution problems in human skin and subdermal tissues". Proceedings of the First International Conference on Numerical Methods in Thermal Problems (ed.K. Morgan (UK: Pineridge Press), 1981, pp. 1067-1076.
Document D16 to the Evidence List presented in the Notice of Opposition to EP3556285, *Abbott Diabetes Care, Inc. v. Dexcom, Inc.*, filed May 6, 2023, A, John Anderson, "Foundations of Computer Technology", 1994, ISBN: 0-412-59810-8, pp. 55-57.
Document D17 to the Evidence List presented in the Notice of Opposition to EP3556285, *Abbott Diabetes Care, Inc. v. Dexcom, Inc.*, filed May 6, 2023, Santinram Kal, "Basic Electronics", 2006, ISBN: 81-203-1952-4, p. 412.
Document D18 to the Evidence List presented in the Notice of Opposition to EP3556285, *Abbott Diabetes Care, Inc. v. Dexcom, Inc.*, filed May 6, 2023, David D. Cunningham and Julie A. Stenken, "In Vivo Glucose Sensing", 2010, ISBN: 978-0-470-11296-0, Chapters 1 and 5.
Document D19 to the Evidence List presented in the Notice of Opposition to EP3556285, *Abbott Diabetes Care, Inc. v. Dexcom, Inc.*, filed May 6, 2023, Frank P. Incropera et al. "Fundamentals of Heat and Mass Transfer", 2007, ISBN: 978-0-471-45728-2, pp. 162-163.
Document D20 to the Evidence List presented in the Notice of Opposition to EP3556285, *Abbott Diabetes Care, Inc. v. Dexcom, Inc.*, filed May 6, 2023, Susan S. Ricci and Terri Kyle, "Maternity and Pediatric Nursing", 2009, ISBN: 978-0-7817-8055-1, p. 949.
Document D21 to the Evidence List presented in the Notice of Opposition to EP3556285, *Abbott Diabetes Care, Inc. v. Dexcom, Inc.*, filed May 6, 2023, Paul G. Barash et al., "Clinical Anesthesia", 2009, ISBN: 978-0-7817-8763-5, p. 711.
Document D22 to the Evidence List presented in the Notice of Opposition to EP3556285, *Abbott Diabetes Care, Inc. v. Dexcom, Inc.*, filed May 6, 2023, El-Radhi AS, Barry W. "Thermometry in paediatric practice". Arch Dis Child. Apr. 2006; 91(4): 351-6.
Document D23 to the Evidence List presented in the Notice of Opposition to EP3556285, *Abbott Diabetes Care, Inc. v. Dexcom, Inc.*, filed May 6, 2023, Nelson, D., Nunneley, S. "Brain temperature and limits on transcranial cooling in humans: quantitative modeling results", Eur J Appl Physiol, 1998, 78: 353-359.
Document D24 to the Evidence List presented in the Notice of Opposition to EP3556285, *Abbott Diabetes Care, Inc. v. Dexcom, Inc.*, filed May 6, 2023, Wikipedia entry for "Human Body Temperature" from Feb. 2011.
Document D25 to the Evidence List presented in the Notice of Opposition to EP3556285, *Abbott Diabetes Care, Inc. v. Dexcom, Inc.*, filed May 6, 2023, Michael Kent, "Advanced Biology", 2000, ISBN: 0-19-9141950-9, p. 154.
Document D26 to the Evidence List presented in the Notice of Opposition to EP3556285, *Abbott Diabetes Care, Inc. v. Dexcom, Inc.*, filed May 6, 2023, Steven B. Heymsfield et al., "Human Body Composition", 2005, ISBN: 978-0-7360-4655-8, p. 168.
Notice of Opposition to EP3556285, *Abbott Diabetes Care, Inc. v. Dexcom, Inc.*, filed May 6, 2023; 138 pages.
Preliminary Opinion in the Opposition to EP3556285, filed Feb. 8, 2024; 14 pages.
Reply to Notice of Opposition to EP3556285, filed by Abbott Diabetes Care, Inc., *Abbott Diabetes Care, Inc. v. Dexcom, Inc.*, filed Oct. 23, 2023; 31 pages.
Document (E1) D27 in Opposition to EP3556285, *Abbott Diabetes Care, Inc. v. Dexcom, Inc.*, Benedict, FG; Miles, WR; Johnson, A (Jun. 1919): "The Temperature of the Human Skin", Proceedings of the National Academy of Sciences of the United States of America; pp. 218-222.
Document (E2) D28 in Opposition to EP3556285, *Abbott Diabetes Care, Inc. v. Dexcom, Inc.*, Webb, Paul, Eur J Appl Physiol (1992) 64: 471-476, "Temperatures of skin, subcutaneous tissue, muscle and core in resting men in cold, comfortable and hot conditions.".
Document (E3) D29 in Opposition to EP3556285, *Abbott Diabetes Care, Inc. v. Dexcom, Inc.*, Bierman, William, "The Temperature of the Skin Surface" (Journal of the American Medical Association. 106 (14): 1158-1162).
Abbott Diabetes Care, Inc. Reply to Summons in the Opposition to EP3556285, dated Aug. 20, 2024; 19 pages.
Dexcom Inc.'s Written Submission in support of the Opposition to EP3556285, dated Aug. 14, 2024; 115 pages.

(56) References Cited

OTHER PUBLICATIONS

Definition of "housing" from the Collins English dictionary. Exhibit D31 in the Opposition to EP3556285.
GlucoWatch User Manual, 2003. Exhibit D33 in the Opposition to EP3556285; 70 pages.
Burnham RS, Mckinley RS, Vincent DD, "Three types of skin-surface thermometers: a comparison of reliability, validity, and responsiveness." Am J Phys Med Rehabil. Jul. 2006; 85(7):553-558. Exhibit D36 in the Opposition to EP3556285.
Kei-Ichiro Kitamura, Xin Zhu, Wenxi Chen, Tetsu Nemoto, "Development of a new method for the noninvasive measurement of deep body temperature without a heater," Medical Engineering & Physics, vol. 32, Issue 1, 2010, pp. 1-6. Exhibit D37 in the Opposition to EP3556285.
Kimberger O., Thell R., Schuh M., Koch J., Sessler D.I., Kurz A., "Accuracy and precision of a novel non-invasive core thermometer." British Journal of Anaesthesia, Aug. 2009; 103(2):226-231. Exhibit D38 in the Opposition to EP3556285.
Dexcom Letter in advance of Oral Proceedings, dated Oct. 11, 2024; 54 pages, in the Opposition to EP3556285, *Abbott Diabetes Care, Inc. v. Dexcom, Inc.*, filed May 6, 2023.
Information regarding the result of oral proceedings, dated Oct. 17, 2024; 2 pages, in the Opposition to EP3556285, *Abbott Diabetes Care, Inc. v. Dexcom, Inc.*, filed May 6, 2023.
Summons to Abbott Diabetes Care, Inc. to attend oral proceedings, dated Oct. 30, 2024, 1 page, in the Opposition to EP3556285, *Abbott Diabetes Care, Inc. v. Dexcom, Inc.*, filed May 6, 2023.
Aleppo, G., et al., "Replace-BG: A Randomized Trial Comparing Continuous Glucose Monitoring With and Without Routine Blood Glucose Monitoring in Adults With Well-Controlled Type 1 Diabetes," Diabetes Care 40(4):538-545, American Diabetes Association, United States (Apr. 2017).
Armour, J.C., et al., "Application of Chronic Intravascular Blood Glucose Sensor in Dogs," Diabetes 39(12):1519-1526, American Diabetes Association, United States (Dec. 1990).
Arnold, M. A., et al., "Selectivity Assessment of Noninvasive Glucose Measurements Based on Analysis of Multivariate Calibration Vectors", Journal of Diabetes Science and Technology, vol. 1, No. 4, 2007pp. 454-462.
Aussedat, B., et al., "A User-friendly Method for Calibrating a Subcutaneous Glucose Sensor-based Hypoglycaemic Alarm," Biosensors Bioelectronics 12(11):1061-1071, Elsevier Advanced Technology, United Kingdom (1997).
Bennion, N., et al., "Alternate Site Glucose Testing: a Crossover Design," Diabetes Technology & Therapeutics 4(1):25-33, Mary Ann Liebert, United States (2002).
Bindra, D.S., et al., "Design and in Vitro Studies of a Needle-Type Glucose Sensor for Subcutaneous Monitoring," Analytical Chemistry 63(17):1692-1696, American Chemical Society, United States (Sep. 11, 991).
Bisdikian, C., "An Overview of the Bluetooth Wireless Technology," IEEE Communications Magazine, pp. 86-94, (2001).
Blank, T.B., et al., "Clinical Results From a Noninvasive Blood Glucose Monitor," Optical Diagnostics and Sensing of Biological Fluids and Glucose and Cholesterol Monitoring II, Proceedings of SPIE vol. 4624, 10 Pages, (May 2002).
Boyne, M.S., et al., "Timing of Changes in Interstitial and Venous Blood Glucose Measured With a Continuous Subcutaneous Glucose Sensor," Diabetes 52(11):2790-2794, American Diabetes Association, United States (Nov. 2003).
Bremer, T.M., et al., "Benchmark Data From the Literature for Evaluation of New Glucose Sensing Technologies," Diabetes Technology & Therapeutics 3(3):409-418, Mary Ann Liebert, Inc, United States (2001).
Brooks, S.L., et al., "Development of an On-line Glucose Sensor for Fermentation Monitoring," Biosensors 3(1):45-56, (1987-1988).
Campbell et al., "Outcomes of Using Flash Glucose Monitory Technology by Children and Young People with Type 1 Diabetes in a Single Arm Study," Pediatric Diabetes, 2018:19:1294-1301; Anlage TW 7, Taylor Wessing, Statement of Defence in *Abbottv. Dexcom*, Opposition to EP 3782539.
Cass, A.E., et al., "Ferrocene-mediated Enzyme Electrode for Amperometric Determination of Glucose," Analytical Chemistry 56(4):667-671, American Chemical Society, United States (Apr. 1984).
Cheyne, E.H., et al., "Performance of a Continuous Glucose Monitoring System During Controlled Hypoglycaemia in Healthy Volunteers," Diabetes Technology & Therapeutics 4(5):607-613, Mary Ann Liebert, United States (2002).
Choudhary, P., et al., "Insulin Pump Therapy With Automated Insulin Suspension in Response to Hypoglycemia: Reduction in Nocturnal Hypoglycemia in Those at Greatest Risk," Diabetes Care 34(9):2023-2025, American Diabetes Association, United States (Sep. 2011).
Clarke, W.L. and Kovatchev, B., "Continuous Glucose Sensors: Continuing Questions about Clinical Accuracy," Journal of Diabetes Science and Technology 1(5):669-675, Sage, United States (Sep. 2007).
Clarke, W.L. and Kovatchev, B., "Statistical Tools to Analyze Continuous Glucose Monitor Data," Diabetes Technology & Therapeutics 11 Suppl 1(Suppl 1):S45-S54, Mary Ann Liebert, Inc., United States (Jun. 2009).
Cryer, P.E., "Preventing Hypoglycaemia: What is the Appropriate Glucose Alert Value?," Diabetologia 52(1):35-37, Berlin Springer Verlag, Germany (Jan. 2009).
Csoregi, E., et al., "Design and Optimization of a Selective Subcutaneously Implantable Glucose Electrode Based on "Wired" Glucose Oxidase," Analytical Chemistry 67(7):1240-1244, American Chemical Society, United States (Apr. 1995).
Deshmukh, H., et al., "Effect of Flash Glucose Monitoring on Glycemic Control, Hypoglycemia, Diabetes-Related Distress, and Resource Utilization in the Association of British Clinical Diabetologists (ABCD) Nationwide Audit," Diabetes Care 43(9):2153-2160, American Diabetes Association, United States (Sep. 2020), Anlage TW 5, Taylor Wessing, Statement of Defence in *Abbottv. Dexcom*, Opposition to EP 3782539.
Diabetes Control and Complications Trial Research Group, "The Effect of Intensive Treatment of Diabetes on the Development and Progression of Long-Term Complications in Insulin-Dependent Diabetes Mellitus", New England J. Med., vol. 329, No. 13, 1993, pp. 977-986.
El-Khatib, F.H., et al., "Adaptive Closed-loop Control Provides Blood-glucose Regulation Using Dual Subcutaneous Insulin and Glucagon Infusion in Diabetic Swine," Journal of Diabetes Science and Technology 1(2):181-192, Sage, United States (Mar. 2007).
Eren-Oruklu, M., "Estimation of Future Glucose Concentrations With Subject-specific Recursive Linear Models," Diabetes Technology & Therapeutics 11(4):243-253, Mary Ann Liebert, Inc., United States (Apr. 2009).
European Patent Application No. 08745803.0, Extended European Search Report mailed Sep. 27. 2012.
European Patent Application No. 08745805.5, Extended European Search Report mailed May 23, 2012.
European Patent Application No. 08745807.1, Extended European Search Report mailed October 8. 2012.
European Patent Application No. 08745809.7, Extended European Search Report mailed Jul. 2, 2012.
European Patent Application No. 08754499.5, Extended European Search Report mailed Sep. 20. 2012.
Exhibit CP-10, Second Expert Report of Dr. Cesar C. Palerm, Oct. 21, 2022, "Standards of Medical Care in Diabetes-2009" Position Statement, American Diabetes Association, 2009, Diabetes Care, 32(1):S13-S61.
Exhibit CP-4, Expert Report of Dr. Cesar C. Palerm, Sep. 20, 2022, "Animas VibeTM, the First Integrated Offering from Animas Corporation and Dexcom, Inc., Receives European CE Mark Approval", Products & Operating Company, 2011, 4 pages.
Exhibit CP-6, Second Expert Report of Dr. Cesar C. Palerm, Oct. 21, 2022, Bailey, T.S et al., "Reduction in Hemoglobin Ale with

(56) References Cited

OTHER PUBLICATIONS

Real-Time Continuous Glucose Monitoring: Results from a 12-Week Observational Study" Diabetes Technology & Therapeutics, 2007, 9(3):203-210.
Exhibit No. 13, to the Expert Report of Professor Nick Oliver, Sep. 20, 2022, Amiel, S et al., "Training in flexible, intensive insulin management to enable dietary freedom in people with type 1 diabetes: dose adjustment for normal eating (DAFNE) randomized controlled trial" BMJ, 2002, 325; 6 pages.
Exhibit No. 21, to the Expert Report of Professor Nick Oliver, Sep. 20, 2022, De Vries, J.H. "Glucose Sensing Issues For the Artificial Pancreas" Journal of Diabetes Science and Technology, 2008, 2(4):732-734.
Exhibit No. 3, to the Expert Report of Professor Nick Oliver, Sep. 20, 2022, "Defining and Reporting Hypoglycemia in Diabetes", American Diabetes Association, Diabetes Care, 2005, 28(5):1245-1249.
Exhibit No. 4, to the Expert Report of Professor Nick Oliver, Sep. 20, 2022, Amiel, S. A., et al., "Hypoglycaemia in Type 2 diabetes", Diabetic Medicine, 2008, 25:245-254.
Exhibit No. 8, to the Expert Report of Professor Nick Oliver, Sep. 20, 2022, Choudhary, p et al., "Hypoglycaemia in the treatment of diabetes mellitus" Oxford Textbook of Endocrinology and Diabetes, 2011 pp. 1849-1860.
Exhibit No. 9, to the Expert Report of Professor Nick Oliver, Sep. 20, 2022, "Guideline on clinical investigation of medicinal products in the treatment or prevention of diabetes mellitus" European Medicines Agency, May 14, 2012, 28 pages.
Facchinetti, Andrea, Ph.D et al., A new Index to Optimally Design and Compare Continuous Glucose Monitoring Glucose Prediction Algorithms, Diabetes Technology & Therapeutics, vol. 13, No. 2, 2011; 10 pages.
Feldman, B., et al., "A Continuous Glucose Sensor Based on Wired Enzyme Technology—Results From a 3-day Trial in Patients With Type 1 Diabetes," Diabetes Technology & Therapeutics 5(5):769-779, Mary Ann Liebert, United States (2003).
Feldman, B., et al., "Correlation of Glucose Concentrations in Interstitial Fluid and Venous Blood During Periods of Rapid Glucose Change," Abbott Diabetes Care, Inc. Freestyle Navigator Continuous Glucose Monitor Pamnhlet, (2004).
Garg, S. and Jovanovic, L., "Relationship of Fasting and Hourly Blood Glucose Levels to HbA1c Values: Safety, Accuracy, and Improvements in Glucose Profiles Obtained Using a 7-day Continuous Glucose Sensor," Diabetes Care 29(12):2644-2649, American Diabetes Association, United States (Dec. 2006).
Garg, S., et al., "Improvement in Glycemic Excursions With a Transcutaneous, Real-time Continuous Glucose Sensor: a Randomized Controlled Trial," Diabetes Care 29(1):44-50, American Diabetes Association, United States (Jan. 2006).
Garg, S.K., et al., "Improved Glucose Excursions Using an Implantable Real-time Continuous Glucose Sensor in Adults With Type 1 Diabetes," Diabetes Care 27(3):734-738, American Diabetes Association, United States (Mar. 2004).
Guerra, S., et al., A Dynamic Risk Measure from Continuous Glucose Monitoring Data, Diabetes Technology & Therapeutics, vol. 13, No. 8, pp. 843-852 (2011).
Haak, T., et al., "Use of Flash Glucose-Sensing Technology for 12 months as a Replacement for Blood Glucose Monitoring in Insulin-treated Type 2 Diabetes," Diabetes Therapy 8(3):573-586, Springer Healthcare, United States (Jun. 2017).
Hayter, P.G., et al., "Performance Standards for Continuous Glucose Monitors," Diabetes Technology & Therapeutics 7(5):721-726, Mary Ann Liebert, Inc., United States (Oct. 2005).
Heller, et al., "Electrochemical Glucose Sensors and Their Applications in Diabetes Management", Chemical Reviews, 108(7):2482-2505 (2008).
Hovorka, R., "Closing the loop", Chapter 13.4.9.2, Oxford Textbook of Endocrinology and Diabetes, Wass et al., Eds., 2011, p. 1869.
Innovation Milestones et al., 2021, retrieved from https://www.medtronicdiabetes.com/about-medtronic-innovation/milestone-timeline, 37 pages.
International Hypoglycaemia Study Group, "Glucose Concentrations of Less Than 3.0 mmol/L (54 mg/dL) Should Be Reported in Clinical Trials: A Joint Position Statement of the American Diabetes Association and the European Association for the Study of Diabetes", Diabetes Care, 2017, vol. 40, pp. 155-157.
International Preliminary Report on Patentability for Application No. PCT/US2011/055177, mailed on Apr. 18, 2013, 7 pages.
International Search Report and Written Opinion for Application No. PCT/US2011/055177, mailed on Feb. 23, 2012, 9 pages.
Isermann, R., and Balle, P., "Trends in the Application of Model-Based Fault Detection and Diagnosis of Technical Processes," Control Engineering Practice 5(5):709-719, (May 1997).
Isermann, R., "Supervision, Fault-detection and Fault-diagnosis Methods—an Introduction," Control Engineering Practice 5(5):639-652, (May 1997).
Johnson, P. C., "Peripheral Circulation," John Wiley & Sons, pp. 198, (1978).
Jungheim, K., et al., "How Rapid Does Glucose Concentration Change in Daily Life of Patients with Type 1 Diabetes?," pp. 250, (2002).
Jungheim, K., et al., "Risky Delay of Hypoglycemia Detection by Glucose Monitoring at the Arm," Diabetes Care (24)7:1303-1306, American Diabetes Association, United States (Jul. 2001).
Kuure-Kinsey, M., et al., "A Dual-rate Kalman Filter for Continuous Glucose Monitoring," Conference Proceedings 2006:63-66, IEEE Service Center (2006).
Li, Y., et al., "In Vivo Release From a Drug Delivery MEMS Device," Journal of Controlled Release 100(2):211-219, Elsevier Science Publishers, Netherlands (Nov. 2004).
Lo, B., and Yang, G-Z., "Key Technical Challenges and Current Implementations of Body Sensor Networks," Body Sensor Networks, pp. 1-5, (2005).
Lodwig, V., et al., "Continuous Glucose Monitoring with Glucose Sensors: Calibration and Assessment Criteria," Diabetes Technology & Theraneutics 5(4):572-586, Mary Ann Liebert, United States (2003).
Malin, S.F., et al., "Noninvasive Prediction of Glucose by Near-infrared Diffuse Reflectance Spectroscopy," Clinical Chemistry 45(9):1651-1658, Oxford University Press, United Kingdom (Sep. 1999).
Marshall, J., "Defining hypoglycaemia: what level has clinical relevance?," Diabetologia 52:31-34, (Nov. 2008).
Mcgarraugh, G., et al., "Physiological Influences on Off-Finger Glucose Testing," Diabetes Technology & Theraneutics 3(3):367-376, Mary Ann Liebert, United States (2001).
Mckean, B.D., and Gough, D.A., "A Telemetry-instrumentation System for Chronically Implanted Glucose and Oxygen Sensors," IEEE Transactions on Bio-medical Engineering 35(7):526-532, Institute Of Electrical And Electronics Engineers, United States (Jul. 1988).
Mcmurry, Jr., J. F., "The Artificial Pancreas Today", Henry Ford Hospital Medical Journal 31(2):77-83, Henry Ford Hospital, United States (1983).
Mgarraugh, G., et al., "Glucose Measurements Using Blood Extracted from the Forearm and the Finger," TheraSense, Inc., 16 Pages, (2001).
Morbiducci, U., et al., "Improved Usability of the Minimal Model of Insulin Sensitivity Based on an Automated Approach and Genetic Algorithms for Parameter Estimation," Clinical Science 112(4):257-263, Portland Press on behalf of the Medical Research Society and the Biochemical Society, United Kingdom (Feb. 2007).
Mougiakakou, S., et al., "A Real Time Simulation Model of Glucose-insulin Metabolism for Type 1 Diabetes Patients," Conference proceedings : Annual International Conference of the IEEE Engineering in Medicine and Biology Society 2006:298-301, IEEE Service Center, United States (2005).
Mougiakakou, S. G., et al., "A Communication Platform for Tele-monitoring and Tele-management of Type 1 Diabetes", Proceedings of the 2005 IEEE Engineering in Medicine and Biology 27th Annual Conference, Shanghai, China, pp. 2207-2210.

(56) References Cited

OTHER PUBLICATIONS

Oliver, N.S., et al., "Glucose Sensors: a Review of Current and Emerging Technology," Diabetic Medicine 26(3):197-210, Blackwell Science, United Kingdom (Mar. 2009).
Palerm, C.C., et al., "Hypoglycemia Detection and Prediction Using Continuous Glucose Monitoring-a Study on Hypoglycemic Clamp Data," Journal of Diabetes Science and Technology 1(5):624-629, Sage, United States (Sep. 2007).
Panteleon, A.E., et al., "The Role of the Independent Variable to Glucose Sensor Calibration," Diabetes Technology & Therapeutics 5(3):401-410, Mary Ann Liebert, Inc., United States (2003).
Parker, R., et al., "Robust Hoo Glucose Control in Diabetes Using a Physiological Model," AIChE Journal 46(12):2537-2549, (Apr. 2000).
PCT/US2012/043012 Isr and Written Opinion dated Nov. 20, 2012.
Pickup, J. C., et al., "Glycaemic control in type 1 diabetes during real time continuous glucose monitoring compared with self monitoring of blood glucose: meta-analysis of randomised controlled trials using individual patient data", British Medical Journal, 343:d3805, British Medical Association, England 14 pages (Jul. 2011).
Pickup, J.C., et al., "Implantable Glucose Sensors: Choosing the Appropriate Sensing Strategy," Biosensors 3(6):335-346, Elsevier Applied Science Publishers, United Kingdom (1987).
Pickup, J.C., et al., "In Vivo Molecular Sensing in Diabetes Mellitus: an Implantable Glucose Sensor With Direct Electron Transfer," Diabetologia 32(3):213-217, Berlin Springer Verlag, Germany (Mar. 1989).
Pishko, M.V., et al., "Amperometric Glucose Microelectrodes Prepared Through Immobilization of Glucose Oxidase in Redox Hydrogels," Analytical Chemistry 63(20):2268-2272, American Chemical Society, United States (Oct. 1991).
Puhr, S., et al., "Real-World Hypoglycemia Avoidance With a Predictive Low Glucose Alert Does Not Depend on Frequent Screen Views", Journal of Diabetes Science and Technology 14(1):83-86, Diabetes Technology Society, United States (Jan. 2020).
Quinn, C.P., et al., "Kinetics of Glucose Delivery to Subcutaneous Tissue in Rats Measured With 0.3-mm Amperometric Microsensors," The American Journal of Physiology 269(1 Pt 1):E155-E161, American Physiological Society, United States (Jul. 1995).
Rilstone, S., et al., "The impact of CGM with a predictive hypoglycaemia alert function on hypoglycaemia in physical activity for people with type 1 diabetes: PACE study", 58th Annual Meeting of the European Association for the Study of Diabetes, Stockholm, 2022, 2 pages.
Rodriguez, N., et al., "Flexible Communication and Control Protocol for Injectable Neuromuscular Interfaces, " IEEE Transactions on Biomedical Circuits and Systems 1(1):19-27, IEEE, United States (Mar. 2007).
Roe, J.N., and Smoller, B.R., "Bloodless Glucose Measurements," Critical Reviews in Therapeutic Drug Carrier Systems 15(3):199-241, Begell House, United States (1998).
Roussel, R., et al., "Important Drop in Rate of Acute Diabetes Complications in People With Type 1 or Type 2 Diabetes After Initiation of Flash Glucose Monitoring in France: The Relief Study", Diabetes Care 44(6):1368-1376, American Diabetes Association, United States (Jun. 2021).
Sakakida, M., et al., "Development of Ferrocene-Mediated Needle-Type Glucose Sensor as a Measure of True Subcutaneous Tissue Glucose Concentrations," Artificial Organs Today 2(2):145-158, (1992).
Sakakida, M., et al., "Ferrocene-Mediated Needle-Type Glucose Sensor Covered with Newly Designed Biocompatible Membrane," Sensors and Actuators B; Chemical 13(1-3):319-322, (May 1993).
Salehi, C., et al., "A Telemetry-Instrumentation System for Long-Term Implantable Glucose and Oxygen Sensors," Analytical Letters 23(13):2289-2308, (Aug. 2006).
Sandham, W., et al., "Blood Glucose Prediction for Diabetes Therapy Using a Recurrent Artificial Neural Network", 9th European Signal Processing Conference, 1998, Rhodes, Greece, pp. 1-4.
Schmidtke, D. W., et al., "Measurement and Modeling of the Transient Difference Between Blood and Subcutaneous Glucose Concentrations in the Rat After Injection of Insulin, " Proceedings of the National Academy of Sciences 95(1):294-299, National Academy of Sciences, United States (Jan. 1998).
Shaw, G.W., et al., "In Vitro Testing of a Simply Constructed, Highly Stable Glucose Sensor Suitable for Implantation in Diabetic Patients," Biosensors & Bioelectronics 6(5):401-406, Elsevier Advanced Technology, United Kingdom (1991).
Shichiri, M., et al., "Glycaemic Control in Pancreatectomized Dogs With a Wearable Artificial Endocrine Pancreas," Diabetologia 24(3):179-184, Berlin Springer Verlag, Germany (Mar. 1983).
Shichiri, M., et al., "In Vivo Characteristics of Needle-type Glucose Sensor—measurements of Subcutaneous Glucose Concentrations in Human Volunteers," Hormone and Metabolic Research. Supplement Series 20:17-20, Academic Press, Germany (1988).
Shichiri, M., et al., "Membrane Design for Extending the Long-Life of an Implantable Glucose Sensor," Diabetes Nutrition and Metabolism 2:309-313, (1989).
Shichiri, M., et al., "Needle-type Glucose Sensor for Wearable Artificial Endocrine Pancreas," Implantable Sensors for Closed-Loop Prosthetic Systems, Chapter 15, pp. 197-210, (1985).
Shichiri, M., et al., "Telemetry Glucose Monitoring Device With Needle-type Glucose Sensor: a Useful Tool for Blood Glucose Monitoring in Diabetic Individuals," Diabetes Care 9(3):298-301, American Diabetes Association, United States (May-Jun. 1986).
Shichiri, M., et al., "Wearable Artificial Endocrine Pancrease With Needle-type Glucose Sensor," Lancet 2(8308):1129-1131, Elsevier, United Kingdom (Nov. 1982).
Shiridhara., et al., "Accuracy of a 14-Day Factory-Calibrated Continuous Glucose Monitoring System With Advanced Algorithm in Pediatric and Adult Population With Diabetes," Journal of Diabetes Science and Technology 16(1):70-77, Diabetes Technology Society, United States (Jan. 2022).
Shults, M.C., et al., "A Telemetry-instrumentation System for Monitoring Multiple Subcutaneously Implanted Glucose Sensors," IEEE Transactions on Bio-medical Engineering 41(10):937-942, Institute Of Electrical And Electronics Engineers, United States (Oct. 1994).
Sparacino, G., et al., "Glucose Concentration Can Be Predicted Ahead in Time from Continuous Glucose Monitoring Sensor Time-Series", IEEE Transactions on Biomedical Engineering 54(5):931-937, Institute Of Electrical And Electronics Engineers, United States (May 2007).
Sternberg, R., et al., "Study and Development of Multilayer Needle-type Enzyme-based Glucose Microsensors," Biosensors 4(1):27-40, Elsevier Applied Science Publishers, United Kingdom (1989).
Swinnen, S. G. H. A., et al., "Changing the glucose cut-off values that define hypoglycaemia has a major effect on reported frequencies of hypoglycaemia", Diabetologia, 52(1):38-41 Berlin Springer Verlag, Germany (Jan. 2009).
Thompson, M., and Vandenberg, E.T., "In Vivo Probes: Problems and Perspectives," Clinical Biochemistry 19(5):255-261, Elsevier Science, United States (Oct. 1986).
Tura, A., et al., "Non-invasive glucose monitoring: assessment of technologies and devices according to quantitative criteria." Diabetes research and clinical practice 77(1):16-40 Elsevier Scientific Publishers, Ireland (Jul. 2007).
Turner, A.P., and Pickup, J.C., "Diabetes Mellitus: Biosensors for Research and Management," Biosensors 1(1):85-115, Elsevier Applied Science Publishers, United Kingdom (1985).
"Type 1 diabetes: diagnosis and management of type 1 diabetes in children, young people and adults", National Collaborating Centre for Women's and Children's Health and the National Collaborating Centre for Chronic Conditions, Clinical Guideline 15, 2004, pp. 1-112.
"Type 1 Diabetes Research Roadmap", JDRF, 2013, pp. 1-38.
Updike, S. J., et al., "Principles of Long-Term Fully Implanted Sensors with Emphasis on Radiotelemetric Monitoring of Blood Glucose from Inside a Subcutaneous Foreign Body Capsule (FBC)," Biosensors in the Body: Continuous in vivo Monitoring, Chapter 4, pp. 117-137, (1997).
Urging FDA to Act Promptly to Approve Artificial Pancreas Technologies, Dan Burton, House of Representatives, Congressional Record, vol. 157, Pt. 13, Nov. 30, 2011; 3 pages.

(56) References Cited

OTHER PUBLICATIONS

Velho, G., et al., "Strategies for Calibrating a Subcutaneous Glucose Sensor," Biomedica Biochimica Acta 48(11-12):957-964, Akademie Verlag, Germany (1989).

Wilson, G.S., et al., "Progress Toward the Development of an Implantable Sensor for Glucose," Clinical Chemistry 38(9):1613-1617, Oxford University Press, United Kingdom (Sep. 1992).

\* cited by examiner

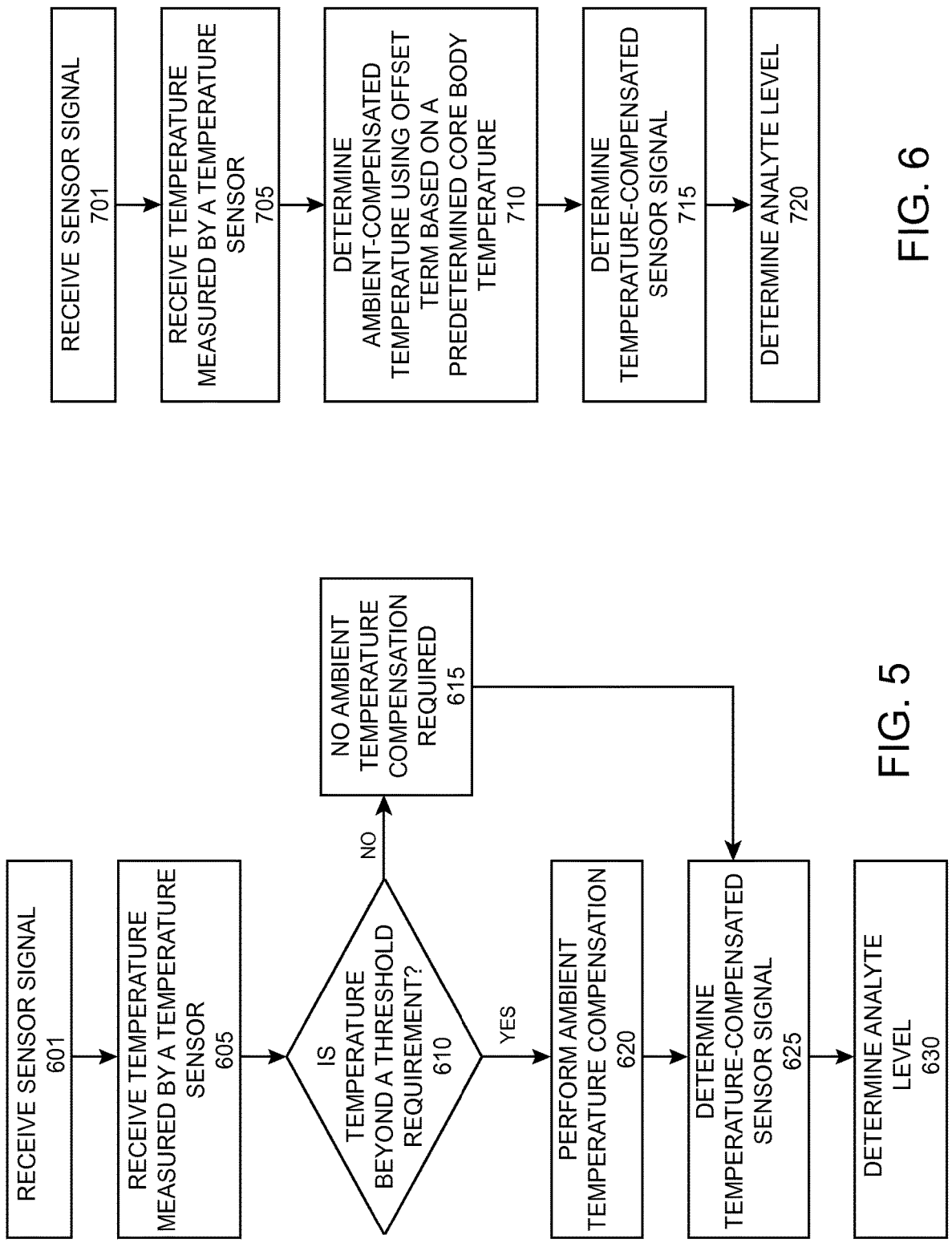

TEMPERATURE-COMPENSATED ANALYTE MONITORING DEVICES, SYSTEMS, AND METHODS THEREOF

CROSS-REFERENCE TO RELATED APPLICATIONS

This application is a continuation of U.S. application Ser. No. 16/525,915, filed Jul. 30, 2019, which is a continuation of U.S. application Ser. No. 15/873,464, filed Jan. 17, 2018, now U.S. Pat. No. 10,398,363; which is a divisional of U.S. application Ser. No. 13/526,394 filed Jun. 18, 2012, now U.S. Pat. No. 9,974,472; which application claims priority to U.S. Provisional Application No. 61/497,821, filed Jun. 16, 2011, the disclosures of each application are incorporated by reference herein in their entireties.

INCORPORATION BY REFERENCE

The following patents, applications and/or publications are incorporated herein by reference for all purposes: U.S. Pat. Nos. 7,041,468; 5,356,786; 6,175,752; 6,560,471; 5,262,035; 6,881,551; 6,121,009; 7,167,818; 6,270,455; 6,161,095; 5,918,603; 6,144,837; 5,601,435; 5,822,715; 5,899,855; 6,071,391; 6,120,676; 6,143,164; 6,299,757; 6,338,790; 6,377,894; 6,600,997; 6,773,671; 6,514,460; 6,592,745; 5,628,890; 5,820,551; 6,736,957; 4,545,382; 4,711,245; 5,509,410; 6,540,891; 6,730,200; 6,764,581; 6,299,757; 6,461,496; 6,503,381; 6,591,125; 6,616,819; 6,618,934; 6,676,816; 6,749,740; 6,893,545; 6,942,518; 6,514,718; 5,264,014; 5,262,305; 5,320,715; 5,593,852; 6,746,582; 6,284,478; 7,299,082; 7,866,026; U.S. Patent Publication No. 2010/0326842; U.S. Patent Publication No. 2010/0198034; U.S. Pat. Nos. 9,402,544; 7,811,231; U.S. Publication No. 2007/0095661; U.S. Publication No. 2006/0091006; U.S. Pat. No. 7,740,581; U.S. Publication No. 2008/0267823; U.S. Publication No. 2007/0108048; U.S. Publication No. 2008/0102441; U.S. Publication No. 2008/0066305; U.S. Publication No. 2007/0199818; U.S. Publication No. 2008/0148873; U.S. Publication No. 2007/0068807; US Publication No. 2010/0198034; U.S. Publication No. 2010/0325868; the disclosures of each of which are incorporated herein by reference in their entirety.

BACKGROUND

In vivo analyte monitoring systems include an in vivo analyte sensor. At least a portion of the sensor is positioned beneath the skin surface of a user to contact bodily fluid to monitor one or more analytes in the fluid over a period of time. This is also referred to as continuous analyte monitoring in that the sensor remains positioned in the user for a continuous period of time.

Analyte sensors may have temperature dependencies and the sensor signals produced by the sensors are may then be affected by temperature changes. An error caused by temperature measurement may lead to an associated error in analyte measurements, such as blood glucose measurements.

SUMMARY

Aspects of the present disclosure relate to analyte monitoring systems, devices, and methods thereof related to temperature compensation, such as temperature compensated glucose values. Included are devices, computer-implemented methods, and systems that determine temperature of an environment surrounding an in vivo glucose sensor, and whether the temperature adversely affects the in vivo analyte sensor glucose data, e.g., the temperature is too high and/or too low. If the temperature may adversely affect the glucose data, the system may be responsive to the temperature information so that erroneous glucose information is not presented to the user. Determined glucose values may be modified or not depending on the temperature and/or glucose values may be displayed to a user or not depending on the temperature. Temperature data may be in vivo temperature data (e.g., obtained at the location of a working electrode of an in vivo analyte sensor during a sensing process such as on or near the body-inserted sensor portion) and/or may be ambient temperature, and/or may be temperature of a processor of a sensor electronics unit such as a sensor control unit and/or may be skin surface temperature.

In certain embodiments, a processor of a glucose monitoring system may always compensate in vivo glucose sensor data based on temperature, but a display device will not display the temperature-compensated glucose values if the temperature is determined to exceed a predetermined threshold, or a processor of a glucose monitoring system will only compensate in vivo glucose sensor data based on temperature if temperature is determined to be within a predetermined range, and a display device will display temperature un-compensated glucose values if the temperature is determined to be within a first range predetermined range and will display temperature-compensated glucose values if temperature is determined to be in a second range.

Embodiments include obtaining glucose data from an in vivo glucose sensor, obtaining temperature data from one or more temperature sensors, comparing the temperature data to a predetermined temperature threshold, and determining a temperature-compensated glucose value if the temperature data does not exceed the predetermined threshold, and not determining a temperature-compensated glucose value if the temperature data does exceed the predetermined threshold. Certain embodiments may include not compensating for temperature if the temperature data is within a predetermined range. In other words, glucose values may be adjusted or not based on temperature data obtained at the same or substantially same time as the glucose data.

Embodiments include methods that include displaying information responsive to obtained temperature data. Embodiments include obtaining glucose data from an in vivo glucose sensor, obtaining temperature data from one or more temperature sensors, comparing the temperature data to a predetermined temperature threshold, and displaying on a user interface device a temperature-compensated glucose value if the temperature data does not exceed the predetermined threshold, and not displaying a temperature-compensated glucose value if the temperature data does exceed the predetermined threshold. In such embodiments, glucose values may be determined or not, but in any event are not communicated to a user if a temperature threshold is exceeded.

Embodiments include computer systems that analyze temperature data for its affects to a glucose sensor. Certain embodiments include an in vivo glucose sensor, at least one temperature sensor, a sensor electronics unit that receives glucose data from the in vivo analyte sensor, and a receiver unit that receives glucose data from the electronics unit. A display may be included with the sensor electronics unit or receiver unit. At least one processor of the electronics unit and/or the receiver unit includes instructions to process temperature data of the at least one temperature sensor and in vivo analyte sensor data of the in vivo analyte sensor, and compare the temperature data to a predetermined temperature threshold, and determine a temperature-compensated glucose value if the temperature data does not exceed the predetermined threshold, and not determine a temperature-compensated glucose value if the temperature data does exceed the predetermined threshold. The at least one processor may include instructions to not compensate for temperature if the temperature data is within a predetermined range. In other words, it may cause glucose values to be adjusted or not based on temperature data obtained at the same or substantially same time as the glucose data. In display embodiments, the one or more processors may include instructions to cause the display to display or not to display information responsive to obtained temperature data. At least one processor includes instructions to process temperature data of the at least one temperature sensor and in vivo analyte sensor data of the in vivo glucose sensor in include obtaining glucose data from an in vivo glucose sensor, and compare the temperature data to a predetermined temperature threshold, and display on the display a temperature-compensated glucose value if the temperature data does not exceed the predetermined threshold, and not display a temperature-compensated glucose value if the temperature data does exceed the predetermined threshold. In such embodiments, the one or more processors may cause glucose values to be determined or not, but in any event are not communicated to a user on a display device if a temperature threshold is exceeded.

In some aspects of the present disclosure, methods of detecting and/or determining an analyte level by compensating for ambient temperature using a temperature sensor (e.g., coupled to an in vivo analyte sensor) are provided. The methods includes receiving a sensor signal (e.g., sensor information, such as current, voltage, etc.) derived from an in vivo analyte sensor; detecting a temperature measurement from a temperature sensor; determining, with a processor, whether a temperature threshold requirement is exceeded based on the temperature measurement; and determining, with the processor, a temperature-compensated analyte sensor signal. When the threshold requirement is not exceeded, the temperature-compensated analyte sensor signal is determined using the temperature measurement. Only when the threshold requirement is exceeded, the temperature-compensated analyte sensor signal is determined using an ambient-compensated temperature that is derived by compensating the temperature measurement for ambient temperature.

In some aspects of the present disclosure, analyte monitoring devices are provided that include a housing; a processor coupled to the housing; and memory communicably coupled to the processor. An in vivo analyte sensor is communicably coupled to the processor, and a temperature sensor is communicably coupled to the processor. The memory includes instructions stored therein that, when executed by the processor, cause the processor to receive a sensor signal from the in vivo analyte sensor; detecting a temperature measurement from the temperature sensor; determine whether a threshold requirement is exceeded based on the temperature measurement; and determine a temperature-compensated analyte sensor signal. When the threshold requirement is not exceeded, the temperature-compensated analyte sensor signal is determined using the temperature measurement. Only when the threshold requirement is exceeded, the temperature-compensated analyte sensor signal is determined using an ambient-compensated temperature that is derived by compensating the temperature measurement for ambient temperature.

In some aspects of the present disclosure, methods of compensating for ambient temperature using a single temperature sensor are provided that include detecting a temperature measurement from a temperature sensor; and determining, with a processor, an ambient-compensated temperature from the temperature measurement using an offset term.

In some aspects of the present disclosure, analyte monitoring devices are provided that include a housing; a processor coupled to the housing; and memory communicably coupled to the processor. An in vivo analyte sensor is communicably coupled to the processor, and a temperature sensor is communicably coupled to the processor. The memory includes instructions stored therein that, when executed by the processor, cause the processor to detect a temperature measurement from the temperature sensor; and determine an ambient-compensated temperature from the temperature measurement using an offset term.

In some aspects of the present disclosure, methods of compensating for ambient temperature using temperature sensors are provided that include sampling at a first sampling rate, with a processor, first temperature measurements from a first temperature sensor on an on-body sensor; determining, with a processor, first ambient-compensated temperatures from the first temperature measurements; and determining, with a processor, final ambient-compensated temperatures by applying a correction gain or factor to the first ambient-compensated temperatures. The correction gain or factor changes value at a slower rate than the sampling rate.

In some aspects of the present disclosure analyte monitoring device are provided that include a housing; a processor coupled to the housing; and memory communicably coupled to the processor. An in vivo analyte sensor is communicably coupled to the processor, and a first temperature sensor and second temperature sensor are communicably coupled to the processor. The memory includes instructions stored therein that, when executed by the processor, cause the processor to sample at a first sampling rate, with a processor, first temperatures measured from a first temperature sensor on the housing; determine first ambient-compensated temperatures from the first temperature measurements; and determine final ambient-compensated temperatures by applying a correction gain or factor to the first ambient-compensated temperatures. The correction gain or factor changes value at a slower rate than the sampling rate.

In some aspects of the present disclosure, in vivo analyte sensors are provided that include a substrate layer; an electrode layer disposed on the substrate layer, and a temperature sensing element disposed on the substrate layer. The electrode layer includes a sensing area, and the temperature sensing element providing a signal for determining temperature adjacent the sensing area.

In some aspects of the present disclosure, analyte monitoring devices are provided that include a housing; electronic circuitry coupled to the housing, the electronic circuitry including a processor; and an in vivo analyte sensor electrically coupled to the electronic circuitry and extending from the housing. The in vivo analyte sensor include a substrate layer; an electrode layer disposed on the substrate layer; and a temperature sensing element disposed on the substrate layer, the temperature sensing element providing a signal for determining temperature adjacent a sensing area.

In some aspects of the present disclosure, analyte sensor devices are provided that include a body including an elongated member having a central tunnel that inserts into skin of a subject, electrodes disposed on the body, and a temperature sensor coupled to the body. The body is adapted to couple to the skin of the subject.

In some aspects of the present disclosure, methods are provided that include coupling an analyte sensor device to a skin of a subject and inserting a temperature sensor within the skin of the subject. The temperature sensor is disposed within the central tunnel. The sensor coupling device includes a body including an elongated member having a central tunnel that inserts into the skin of a subject, and electrodes disposed on the body. The body is adapted to couple to the skin of the subject.

In some aspects of the present disclosure, methods are provided that include receiving a first sensor signal from a first electrode on an in vivo analyte sensor on an on-body sensor; receiving a second sensor signal from a second electrode on the in vivo analyte sensor, and determining, with a processor, a compensated temperature at the two working electrodes based on the difference between the temperature dependencies for the different sensing chemistries on the two working electrodes. The first electrode and second electrode include different sensing chemistries with different temperature dependencies.

In some aspects of the present disclosure, analyte monitoring devices are provided that include a housing; a processor coupled to the housing; and memory communicably coupled to the processor. An in vivo analyte sensor is communicably coupled to the processor, and the in vivo analyte sensor includes two working electrodes. The memory includes instructions stored therein that, when executed by the processor, cause the processor to detect a first sensor signal from a first electrode on the in vivo analyte sensor; detect a second sensor signal from a second electrode on the in vivo analyte sensor; and determine a compensated temperature at the two working electrodes based on the difference between the temperature dependencies for the different sensing chemistries on the two working electrodes. The first electrode and second electrode include different sensing chemistries with different temperature dependencies.

BRIEF DESCRIPTION OF DRAWINGS

FIG. 5 illustrates a flowchart for a method of determining an analyte level by compensating for ambient temperature using a single temperature sensor on an on-body sensor, according to certain embodiments;

FIG. 6 illustrates a flowchart for a method of compensating for ambient temperature using a single temperature sensor on an on-body sensor, according to certain embodiments;

DETAILED DESCRIPTION

Figure 1:
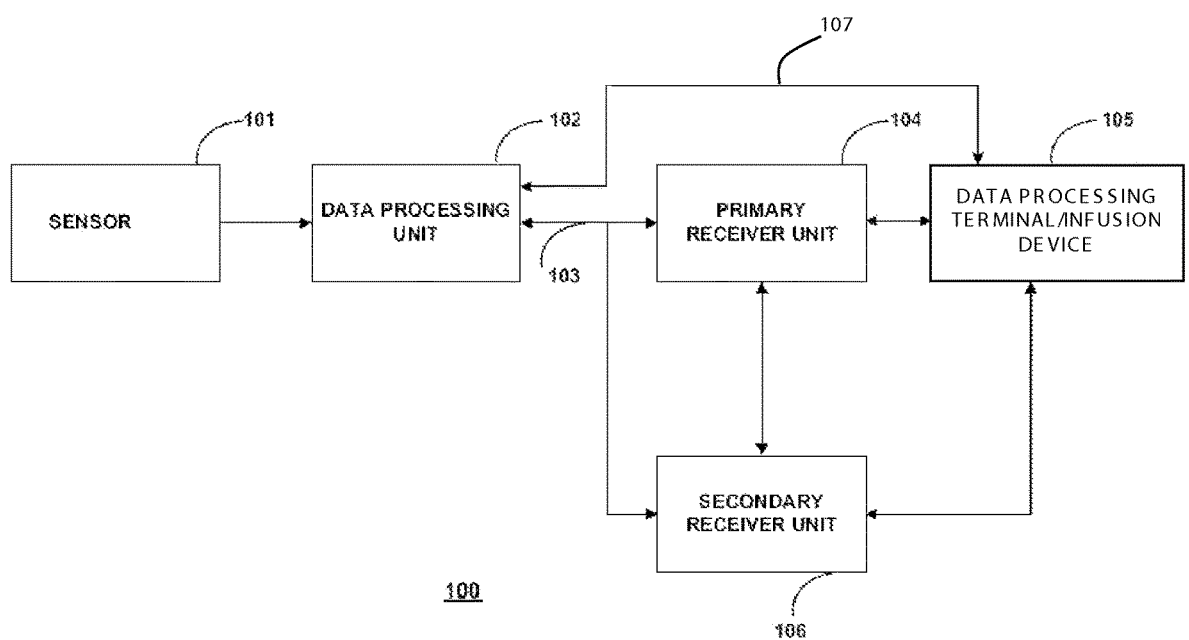
FIG. 1 shows a block diagram of an embodiment of an analyte monitoring system, according to certain embodiments.

Before the present disclosure is described in additional detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

The analyte sensor may be configured so that at least a portion thereof is placed under the skin of the patient to detect the analyte levels of the patient, and another portion of the analyte sensor—which may be above the skin—is coupled to electronics within a housing that is positioned externally on the skin of the subject. The electronics may include various components, such as communication element(s) for communication with a remote receiving unit. The analyte monitoring device that is coupled to the subject's body and includes the in vivo positioned analyte sensor, housing, and electronics (e.g., data processing, storage, and/or communication components) is also referred to herein as an "on-body unit", "OBU", "on-body sensor", "on body patch", or "patch".

Analyte sensors may have temperature dependencies and the sensor signals produced by the sensors may then be affected by temperature changes. An error caused by temperature may lead to an associated error in analyte measurements, such as glucose measurements.

It should be appreciated the subject matter of the disclosure is not limited to transcutaneous analyte sensor, but is also applicable to in vivo analyte sensors in general.

Temperature Compensation

As summarized above, aspects of the present disclosure relate to analyte monitoring systems, devices, and methods thereof related to temperature compensation. It should be appreciated that while the devices and methods may be described in terms of a subcutaneous sensor, other in vivo analyte sensors may also be applicable and the subject matter not limited to specifically subcutaneous analyte sensors.

It should also be appreciated that the embodiments described herein are exemplary and should not be viewed as limiting. For example, it should be appreciated that the methods described herein may be implemented in an on-body unit, the receiver, or mixed between the on-body unit and the receiver. Thus, various combinations of the steps performed on the on-body unit or receiver are contemplated. For example, an on-body unit may perform some steps such as temperature measurement and transmit the measurement to a receiver, where a processor on the receiver performs subsequent processing, such as determining ambient temperature compensation, determining temperature-compensated analyte sensor signals, determining analyte levels, etc. Or, as another example, the on-body unit may perform the steps of measuring the temperature, determining ambient temperature compensation, and determining temperature-compensated analyte sensor signals. For instance, the on-body unit may transmit the results to a receiver wherein the results are provided on a user interface.

It is noted that the combinations of steps between the on-body unit and receiver are appreciated for the one temperature sensor and two temperature sensor embodiments. Thus, for example, steps in the two temperature sensor embodiments may also be performed on the on-body unit or the receiver in other embodiments—e.g., sampling of temperature sensors, and/or correction factor or gain determination, determining ambient temperature compensation, determining temperature-compensated analyte sensor signals, etc.

It is also appreciated that temperatures may be measured by a processor on the on-body unit and/or receiver. For example, a processor may receive temperature data from a temperature sensor and calculate a temperature from the temperature data. The temperature may be, for example, an analog or digital signal derived by the temperature sensor. For example, in certain embodiments, a processor on the on-body unit may be coupled to the temperature sensor and provide a temperature measurement to the receiver, wherein the receiver detects the temperature measurement communicated and then performs additional processing steps based on the temperature measurement. It is appreciated that in another embodiment, the temperature data from the temperature sensor is sent to the receiver and the processor on the receiver calculates the temperature from the temperature data. The processor may then use this detected temperature for additional processing steps.

Compensating Sensor Signals

Temperature measurements are important for obtaining accurate analyte measurements (e.g., glucose measurements) with on-body sensors that are part of in vivo analyte monitoring systems—e.g., continuous glucose monitor (CGM) systems or intermittent or periodic glucose monitoring systems. The analyte-sensing chemistry on a subcutaneously positionable analyte sensor, or other in vivo analyte sensor, of the on-body sensor is temperature dependent and the sensor signal produced by the in vivo analyte sensor is thus affected by temperature.

Subcutaneously inserted glucose sensors, for example, may measure glucose by correlating the sensor signal output with glucose concentration. The signal response of analyte sensor may be linear across the operating range of glucose concentrations. However, the slope of this response may vary as temperature around the analyte sensor tip changes.

In order to compensate for this thermal effect, knowledge of temperature around the sensor sensing area is needed. The term "sensing area" is used herein to mean the area of the analyte sensor where the sensing chemistries are located. For example, in certain embodiments, the sensing area is disposed at the sensor tip, and thus the temperature at the sensor tip is estimated.

Therefore, the effect of temperature may be taken into account in order to calculate an accurate value for glucose concentration.

On-body sensors may utilize a temperature sensor disposed near the in vivo analyte sensor to estimate the sensor temperature. This temperature measurement is used to compensate the analyte sensor signal for temperature effects. For example, temperature-compensated analyte sensor signal may be determined by:

$$I_{TC}=I*1.07^{\wedge}(32.5-T),$$

where I is the raw sensor current, T is the measured temperature in degrees Celsius (C), and $I_{TC}$ is the temperature compensated signal that is proportional to glucose concentration.

Ambient temperature impinging on the on-body housing may influence temperature measurements, and in effect, create a temperature measurement error that will lead to a glucose calculation error. For example, in some instances, experiments have shown that in an ambient temperature environment of 20 degrees C., the resulting glucose error due to ambient temperature effects can be about 10%.

In some aspects of the present disclosure, on-body sensors employ a second temperature sensor used to compensate for errors in the sensor temperature measurement due to the influence of ambient temperature on the first temperature sensor. For example, one temperature sensor (T1) may be located close to the skin surface Tskin, and another temperatures sensor (T2) located close to the transmitter (TX) processor or on the printed circuit board (PCB).

The temperature which compensates for ambient temperature influence using two temperature sensors is determined by, for example:

$$T=T1+K*(T1-T2)$$

where K is related to the thermal resistances between the first temperature sensor and the second temperature sensor, and is a constant (e.g., 0.5, 0.2, or other constant) that may be derived empirically; T1 is the measured temperature at the temperature sensor near the sensor; T2 is the measured ambient temperature from the second temperature sensor; and T is the temperature which is compensated for ambient temperature influence. Other more complex models may be contemplated; for instance, K may not be constant but rather a function of T1 and/or T2, for instance.

Ambient Temperature Compensation Using a Single Temperature Sensor

To estimate the temperature at the sensing area of the in vivo analyte sensor, ambient compensation may be performed. In some aspects of the present disclosure, ambient temperature compensation is provided using a single temperature sensor on the on-body sensor. Thus, a second temperature is not required to compensate for ambient effects. Having a single temperature instead of multiple temperature sensors may provide one or more benefits, such as a reduction in cost, a reduction in complexity, etc.

FIG. 5 illustrates a flowchart for a method of determining an analyte level by compensating for ambient temperature using a single temperature sensor (e.g., a temperatures sensor that approximates skin temperature) on an on-body sensor, according to certain embodiments.

At block 601, a sensor signal is received from an in vivo analyte sensor that is transcutaneously positioned with the skin of a subject. For example, the on-body sensor may include a processor that is electrically coupled to the analyte sensor and receives the sensor signal.

At block 605, the processor receives a temperature signal from a temperature sensor coupled to the on-body sensor. The temperature sensor may be, for example, positioned at or near a skin contacting surface to represent skin temperature. Since skin temperature may be affected by ambient temperature, a change in skin temperature may be correlated to a change in ambient temperature. When the ambient temperature is low, skin temperature will decrease, and when the ambient temperature is high, skin temperature will increase. Thus, deviations from "normal" skin temperature may be used to represent how strong the ambient temperature effects are.

At block 610, the processor determines if the measured temperature has reached a predetermined threshold value. For instance, a normal temperature or normal temperature range may be established and any deviation past the established threshold or thresholds (e.g., outside the normal temperature range) will trigger the ambient temperature correction. It should be appreciated that the term "predetermined threshold" is used broadly herein, and may include an upper and lower threshold. For example, an upper threshold and lower threshold may be implemented in some instances to establish a range. In some instances, only an upper or lower threshold may be implemented.

If the skin temperature does not deviate beyond the threshold, then it can be assumed that the ambient temperature effects are minimal, and no ambient temperature compensation is required, as represented by block 615. The temperature measurement may then be used to determine the temperature compensated analyte sensor signal, $I_{TC}$, as represented by block 625, and transmitted or displayed as a corresponding analyte (e.g., glucose) level, as represented by block 630.

If the skin temperature deviates beyond the predetermined threshold, then it can be assumed that the ambient temperature effects are significant, and ambient temperature compensation is performed (e.g., a correction factor applied) to compensate for the effects of ambient temperature, as represented by block 620. The resulting ambient-compensated temperature is then used to determine the temperature-compensated analyte sensor signal, $I_{TC}$, as represented by block 625, for a more accurate analyte (e.g., glucose) level determination that is transmitted or displayed, as represented by block 630.

For example, skin temperature for most people may normally range between 30 and 35° C. in ambient temperature environments that people are comfortable in. In certain embodiments, ambient temperature compensation is applied when "extreme" skin temperatures are detected (e.g., when the skin temperatures deviate beyond the predetermined threshold or thresholds). For instance, when the skin temperature measurement from the temperature sensor drops below 30 degrees C., then a correction factor can be added to the temperature measurement.

It should be appreciated that the predetermined threshold or thresholds (e.g., the "normal" range) may vary, and further, that the actual compensation algorithm (e.g., correction factor) implemented may also vary. As an example, ambient temperature compensation may be provided by the correction factor:

If $T<30$, then $T_{corrected}=T+1$

AND

IF $T>35$, then $T_{corrected}=T-1$

As another example, the ambient temperature compensation may be provided by a slightly more complex correction factor, such as:

If $T<30$, then $T_{corrected}=T+(30-T)/5$

AND

If $T>35$, then $T_{corrected}=T-(T-35)/5$ $T_{corrected}$ is then used to determine the temperature-compensated analyte sensor signal. In this way, the temperature-compensated analyte sensor signal accounts for ambient temperature influence. It should be appreciated that correction factors of varying complexities may be implemented in other embodiments.

It should be appreciated that illness may also affect the skin temperature of a subject—e.g., to make the skin temperature elevate outside the normal range. In certain embodiments, the ambient temperature compensation is applied only if the temperature error causes a high reading. In this way, only low temperature measurements are compensated.

In certain embodiments, changes in skin temperature are used to detect and correct for ambient temperature influences. For example, an ambient correction factor may be applied after a change in skin temperature is detected. It should be appreciated that the magnitude of the change may vary in different implementations as desired. For example, in some instances, a "normal" temperature could be detected at the start of a sensor wear, and when the temperature deviates by some predetermined amount (or, for example, by an amount detected by monitoring the changes during a period at the start of a sensor wear), then the ambient temperature compensation can be performed, such as described above.

In certain embodiments, temperature changes above a certain absolute value over a predetermined period of time initiates the ambient temperature compensation. For instance, $$T(t=0)-T(t=-10)>5, \text{ then } T_{corrected}=T+1$$

$$T(t=0)-T(t=-10)<-5, \text{ then } T_{corrected}=T-1$$

In certain embodiments, the ambient temperature compensation is based on the rate of change of skin temperature. In other embodiments, a combination of absolute temperature checks and temperature rate of change could be used in both the detection and correction.

It should be appreciated that the embodiment shown in FIG. 5 is exemplary, and that one or more steps may be performed by a processor on the on-body unit and/or a receiver in communication with the on-body unit in other embodiments. For example, in certain embodiments, the temperature sensor is coupled to the on-body unit and a processor on the on-body unit is detecting the temperature measurement, determining whether the threshold requirement is met, performing the ambient temperature compensation, and determining the temperature-compensated signal. Then, for example, the temperature-compensated signal is sent to a receiver wherein the temperature-compensated analyte level is displayed on a user-interface of the receiver for instance. In another embodiment, for example, the temperature sensor is coupled to the on-body unit and a processor on the on-body unit transmits the temperature measurements to the receiver where a processor coupled to the receiver determines whether the threshold requirement is met, performs the ambient temperature compensation, and determines the temperature-compensated signal. Then, for example, the temperature-compensated analyte level is displayed on a user-interface of the receiver for instance. It should be appreciated that the steps may be split up in other combinations between the on-body unit and the receiver.

It should be appreciated that, in certain embodiments, the ambient temperature compensation may, for the most, always or continuously be performed on the received analyte sensor signal. For example, the processor may continuously perform the ambient temperature compensation on the analyte sensor signal in addition to determining if the threshold temperature has been exceeded. When the temperature measurement does not exceed the temperature threshold, the temperature-compensated analyte sensor signal is based off the uncompensated signal, resulting in uncompensated analyte levels. When the temperature measurement exceeds the temperature threshold, the temperature-compensated analyte sensor signal is based off the ambient-compensated signal, resulting in ambient-compensated analyte levels. Thus, the temperature-compensated analyte sensor signal results in a mixed signal of the uncompensated analyte levels and ambient-compensated analyte levels. The temperature-compensated analyte sensor signal may be transmitted (e.g., communicated to a receiver) or presented on a user interface (e.g., displayed on a display for the user).

In other embodiments, the ambient-temperature compensation is not always or continuously performed on the received analyte sensor signal, but rather, only when the temperature threshold is exceeded. When the temperature measurement does not exceed the temperature threshold, the temperature-compensated analyte sensor signal is based off the uncompensated signal, resulting in uncompensated analyte levels presented on a user interface (e.g., displayed on a display). When the temperature measurement exceeds the temperature threshold, ambient-compensation is performed and the temperature-compensated analyte sensor signal is based off the ambient-compensated signal, resulting in ambient-compensated analyte levels presented on the user interface. Again, the temperature-compensated analyte sensor signal results in a mixed signal of the uncompensated analyte levels and ambient-compensated analyte levels.

It is also appreciated that in certain embodiments, the ambient compensation may be based off predetermined temperature ranges rather than predetermined thresholds. For example, the uncompensated analyte sensor signal may be used when the temperature measurement falls within a predetermined range or ranges, and the ambient compensated signal is used when the temperature measurement falls within another predetermined range or ranges.

It should be appreciated that in certain embodiments the temperature compensation may be applied to an analyte sensor signal that is not yet calibrated or converted (e.g., scaled by a scaling factor) to a corresponding analyte level, and thereafter converted to the corresponding analyte level. In yet other embodiments, the temperature compensation is applied to an analyte sensor signal that already represents the analyte level (e.g., is already calibrated or converted to the corresponding analyte level), and the temperature-compensated analyte sensor signal is the temperature compensated analyte level.

Ambient Temperature Compensation Based on Core Body Temperature

As previously noted, some on-body units may include a correction algorithm that utilizes two temperatures sensors to compensate for ambient temperature influence on the temperature sensor. For example, one temperature sensor is located close to the skin in a can that protrudes from the bottom of the transmitter. The other temperature sensor is located on the printed circuit board (PCB) in the transmitter and is a feature provided by the controller chip. Again, the correction method employed is:

$$T=T1+K*(T1-T2)$$

This method can be considered an "extrapolation" method, since two temperature measurements are made at points where the temperature for each is lower than the sensing area temperature, and the sensing area temperature is estimated by extrapolating from these two measured temperatures. In this transmitter configuration, the two temperature sensors are generally well separated, which results in a stable K value that is robust over different transmitter locations on the body and for different body types. As transmitter designs become physically smaller, however, it becomes more difficult to separate the two temperature sensors thermally. Without adequate thermal separation, the K value becomes significantly less stable, and furthermore, becomes significantly larger, with the effect of amplifying the noise in the temperature measurement.

Utilizing a single temperature sensor instead of two may provide many advantages, such as cost savings. In some aspects of the present disclosure, ambient temperature compensation is based on a predetermined core body temperature and temperature measurements from a single temperature sensor.

FIG. 6 illustrates a flowchart for a method of compensating for ambient temperature using a single temperature sensor on an on-body unit, according to certain embodiments.

At block 701, a sensor signal is received from an analyte sensor that is transcutaneously positioned within the skin of a subject, or otherwise implanted in vivo. For example, the on-body unit may include a processor that is electrically coupled to the analyte sensor and receives the analyte sensor signal.

At block 705, the processor receives temperature data from a temperature sensor coupled to the on-body unit. For example, in certain embodiments, the temperature sensor may be positioned at or near a skin contacting surface to represent skin temperature.

At block 710, the processor determines an ambient-compensated temperature from the measured temperature using an offset term (e.g., an offset term based on a predetermined core body temperature). For example, a correction factor is applied to the measured temperature to correct for ambient temperature effects. The correction factor may have an offset term that is based on a predetermined core body temperature value—e.g., 37° C. since a user's core body temperature is relatively stable at approximately 37° C. For example, ambient temperature compensation may be provided by the following correction factor:

$$T_{est} = B_{corebody} + K*T1$$

where $B_{corebody}$ is a predetermined core body temperature (e.g., approximately 37 degrees C.); K is a constant that may be empirically derived; and T1 is the measured temperature by the temperature sensor; and $T_{est}$ is the estimated sensing area temperature that is compensated for ambient temperature influence.

The resulting sensing area (e.g., sensor tip) temperature estimate is compensated for ambient effects and may then be used to determine the temperature-compensated analyte sensor signal, $I_{TC}$, as represented by block 715, for a more accurate glucose level determination that is transmitted or displayed, as represented by block 720.

The sensing area temperature estimate is an "interpolation" method since the sensing area temperature estimate is in between the core body temperature and the temperature measured at the transmitter. Measurement noise is not amplified using the interpolation method.

As similarly stated above, it should be appreciated that the embodiment shown in FIG. 6 is exemplary, and that one or more steps may be performed by a processor on the on-body unit and/or a receiver in communication with the on-body unit in other embodiments. For example, in certain embodiments, the temperature sensor is coupled to the on-body unit and a processor on the on-body unit detects the temperature measurement, determines an ambient-compensated temperature from the measured temperature using an offset term, and determines the temperature-compensated signal. Then, for example, the temperature-compensated signal is sent to a receiver wherein the temperature-compensated analyte level is displayed on a user-interface of the receiver for instance. In another embodiment, for example, the temperature sensor is coupled to the on-body unit and a processor on the on-body unit transmits the temperature measurements to the receiver where a processor coupled to the receiver determines an ambient-compensated temperature from the measured temperature using an offset term, and determines the temperature-compensated signal. Then, for example, the temperature-compensated analyte level is displayed on a user-interface of the receiver for instance. It should be appreciated that the steps may be split up in other combinations between the on-body unit and the receiver.

Using One-Temperature Sensor Models and Two-Temperature Sensor Models

Subcutaneously inserted glucose sensors measure glucose by correlating the sensor signal output with glucose concentration. As stated above, this signal output is affected by temperature. As stated above, in some instances, temperature is estimated using two temperature sensors.

For example, in certain embodiments, one thermistor is disposed close to the skin surface to provide a skin temperature measurement, $T_{skin}$. Another thermistor is disposed away from the skin surface to provide a temperature measurement, $T_{cpu}$, that may be near the on-body processor that is has more influence from the ambient temperature and less influence from the sensor tip temperature than $T_{skin}$.

Figure 7:
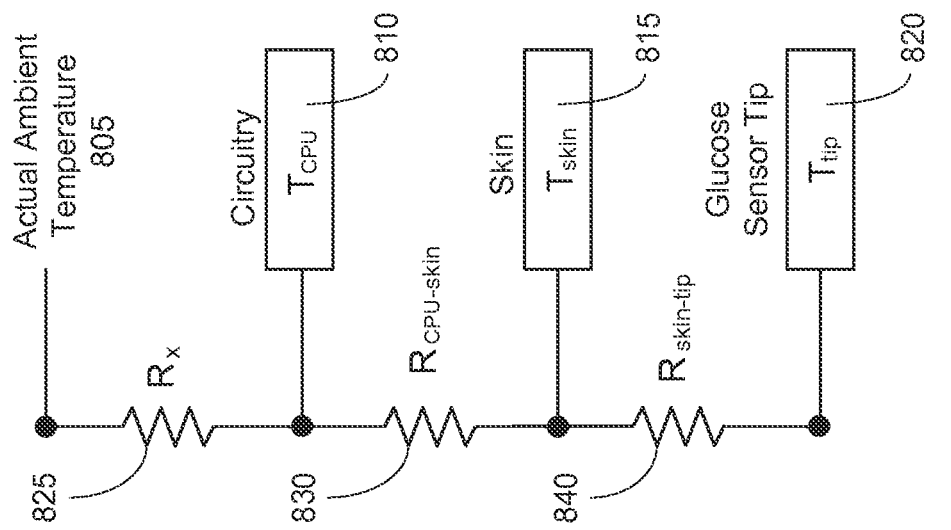
FIG. 7 illustrates a circuit diagram representation of an example two-thermistor model, according to certain embodiments.

FIG. 7 illustrates a circuit diagram representation of an example two-thermistor model, according to certain embodiments. It should be appreciated that in other embodiments a different type of temperature sensor may be implemented.

As shown, temperature 805 is ambient air temperature; temperature $T_{cpu}$ 810 is the temperature at the circuitry (e.g., processor); temperature $T_{skin}$ 815 is the temperature at the skin surface; and temperature $T_{tip}$ 820 is estimated temperature at the sensing area (e.g., at the sensor tip). Resistance $R_x$ 825 represents thermal resistance between the ambient air and circuitry; $R_{cpu-skin}$ 830 represents thermal resistance between the circuitry and the skin; and $R_{skin-tip}$ 835 represents thermal resistance between the skin and sensing area.

$K=R_{skin-tip}/R_{cpu-skin}$ is a fixed constant, which acts as a scaling factor to extrapolate the difference $T_{tip}-T_{skin}$ as a function of the difference $T_{skin}-T_{cpu}$.

$$T_{tip}-T_{skin}=K*(T_{skin}-T_{cpu})$$

This relationship is used to calculate the temperature at the sensing area, $T_{tip}$:

$$T_{tip}=T_{skin}+K*(T_{skin}-T_{cpu})$$

In some aspects, the two-thermistor model has relative insensitivity to changes in ambient temperature, core body temperature, and site-to-site thermal impedance variability. The two-sensor model may also possess minute-to-minute variability in the temperature sensor (e.g., thermistor) readings $T_{cpu}$ and $T_{skin}$ that can degrade the smoothness of the temperature corrected glucose signal. This is especially a concern when plasma-to-interstitial glucose lag compensation is required.

In certain embodiments, the one-sensor model described above assumes that the core body temperature is the dominant heat source, and that the thermal resistance between the core body and the sensing element is universally constant.

Figure 8:
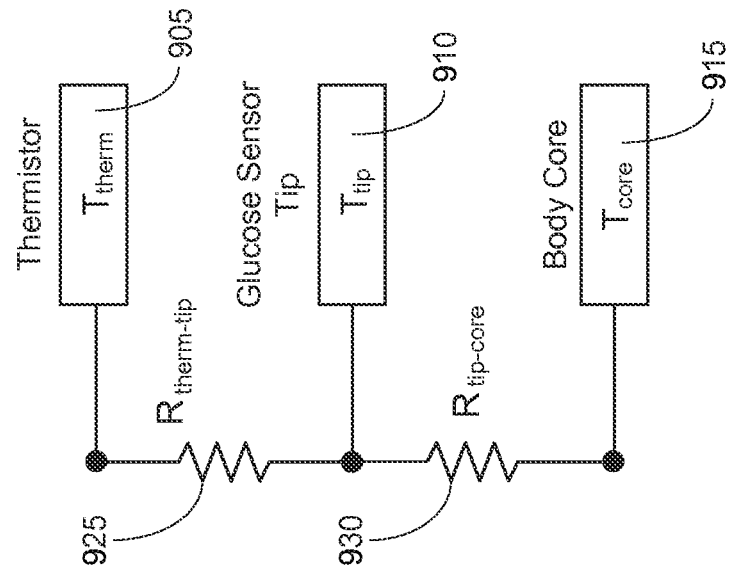
FIG. 8 illustrates a circuit diagram representation of an example one-thermistor model, according to certain embodiments.

FIG. 8 illustrates a circuit diagram representation of an example one-thermistor model, according to certain embodiments. As shown, temperature $T_{therm}$ 905 is the temperature at the thermistor; sensing area temperature (e.g., sensor tip temperature) $T_{tip}$ 910 is the estimated temperature at the sensing area, and body core temperature $T_{core}$ 915 is the predetermined body core temperature. $R_{therm\text{-}tip}$ 925 represents thermal resistance between the thermistor and the sensing area. $R_{tip\text{-}core}$ 930 represents thermal resistance between the sensing area and the core body.

Where $K_{1TM} = R_{tip\text{-}core}/R_{therm\text{-}tip}$, such that $T_{tip}$ can be calculated as follows:

$$T_{tip} = (T_{therm} * K_{1TM} + T_{core})/(1 + K_{1TM})$$

where $K_{1TM}$ is an empirically derived constant for the one-thermistor model.

Since the model does not extrapolate between two measurement channels, improved minute-to-minute smoothness occurs. Experimental data suggests that while the one-thermistor model has a very consistent minute-to-minute estimate, the site-to-site variability results in a poorer overall $T_{tip}$ estimate compared to the two-thermistor model. $R_{tip\text{-}core}$ in the one-thermistor model assumes knowledge of a constant thermal resistance between the body's core temperature and the sensing area (e.g., sensor tip). The value of this resistance might vary between the arm and abdomen sites because of different proximities to the body core.

The minute-to-minute variability that is caused by the extrapolation operation of the two-thermistor model measurements directly affects the minute-to-minute variability of the glucose measurement. In addition, it limits the extent of plasma-to-interstitial glucose lag correction possible.

In some aspects of the present disclosure, a correction gain is determined based on temperature estimates calculated using the one-thermistor model and the two-thermistor model. For instance, two thermistors are disposed on the on-body sensor, such as described above for the two-thermistor model. Temperature estimates are calculated using the one-thermistor model technique, resulting in sensor temperature estimate $T_{1TM}$. Temperature estimates are also calculated using the two-thermistor model, resulting in sensor temperature estimate $T_{2TM}$.

In certain embodiments, present to recent past comparisons of the two temperature estimates $T_{1TM}$ and $T_{2TM}$ are used to improve the accuracy of the sensor temperature measured $T_{1TM}$ and utilize this recursively modified estimate of the sensor temperature. The result is a sensor temperature estimate that has the minute-to-minute smoothness (which is related to precision) of the one-thermistor model, yet has the site-to-site variability (which is related to accuracy) of the two-thermistor model. This approach allows for a smoother temperature corrected raw glucose signal, which helps improve the signal quality of the final product, reduce the uncertainty of threshold and projected alarms due to unnecessary noise, reduce the uncertainty of rate arrows, reduce the impact of non-physiological temperature transients, and allow for better concordance to reference blood glucose.

Figure 9:
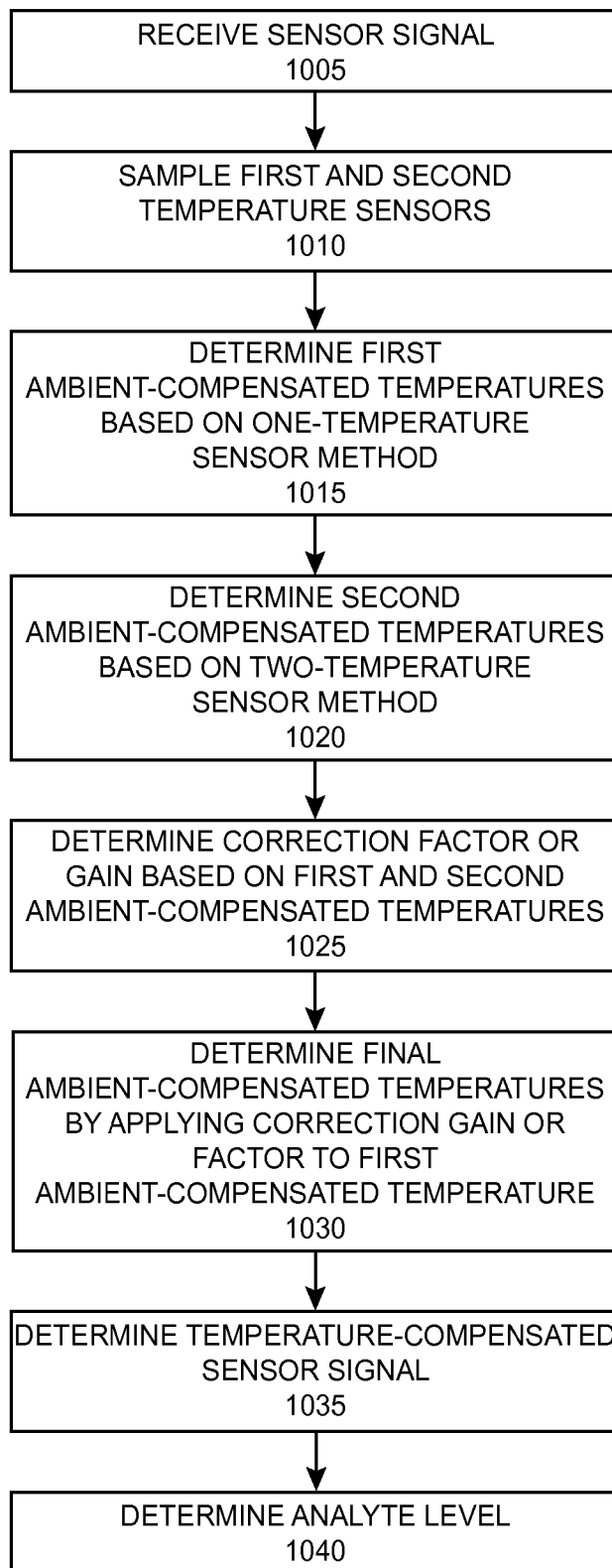
FIG. 9 illustrates method of compensating for ambient temperature using temperature sensors on an on-body sensor, according to certain embodiments.

FIG. 9 illustrates method of compensating for ambient temperature using temperature sensors on an on-body unit, according to certain embodiments.

At block 1005, a sensor signal is received from an analyte sensor that is transcutaneously positioned within the skin of a subject, or otherwise implanted in vivo. For example, the on-body unit may include two temperature sensors (e.g., two thermistors) and a processor that is electrically coupled to the analyte sensor and receives the sensor signal.

At block 1010, first and second thermistors on the on-body unit are sampled by the processor. At block 1015, the processor determines ambient-compensated temperatures based on a one temperature model. At block 1020, the processor determines ambient-compensated temperatures based on a two temperature model.

At block 1025, correction gain or factor is determined based on past sampled ambient-compensated temperatures for the one-thermistor and two-thermistor models. At block 1030, a final ambient-compensated temperature is determined by applying the correction gain or factor to the ambient-compensated temperatures determined in block 1015.

For example, in certain embodiment, a simple gain error model is assumed on the one thermistor model. In other words:

$$T_{1TM}(k) = K_{1TM}(k) \times T_{1TMnominal}(k)$$

where $T_{1TMnominal}$ is the nominal output based on the one-thermistor model as previously described, $K_{1TM}$ is the correction gain for this model, and $T_{1TM}$ is the final ambient-compensated temperature resulting from using the improved one-thermistor model.

"k" refers to the index of the sample instance/time. Note that the value $T_{1TMnominal}$ is computed during every sample instance and attempts to reflect the latest temperature, which may or may not be rapidly varying over time. However, $K_{1TM}$ is computed such that the value changes very slowly over time, with the assumption that the biological and environmental factors that affect this gain error changes very slowly over time. $K_{1TM}$ changes at a rate slower than the sampling rate. In certain embodiments, this is achieved by performing a moving average between the nominal one-thermistor model and two-thermistor model outputs:

$$K_{1TM}(k) := \frac{1}{N} \sum_{j=0}^{N-1} \frac{T_{2TM}(k-j)}{T_{1TMnominal}(k-j)}$$

where $T_{2TM}$ is the output of the two-thermistor model, and N is a relatively large positive window such that $K_{1TM}$ varies very slowly and reliably over time. The values of $T_{1TMnominal}$ and $T_{2TM}$ pairs are such that both values are valid and/or can be computed at any time index within the set of N most recent pairs.

In an alternative embodiment, the same assumptions are made as the previous embodiment, but the evolution of $K_{1TM}$ is governed by a calculation that is more robust to occasional $T_{1TM}$ nominal and $T_{2TM}$ outliers. As in the previous embodiment, the values of $T_{1TMnominal}$ and $T_{2TM}$ pairs must be such that both values are valid and/or can be computed at any time index within the set of N most recent pairs.

$$K_{1TM}(k) := \frac{\sum_{j=0}^{N-1} T_{2TM}(k-j)}{\sum_{j=0}^{N-1} T_{1TMnominal}(k-j)}$$

In yet another embodiment, parameter adaption is used. One example is to use the MIT adaption rule:

$$d/dt\, K_{1TM}(t) = -\gamma e(t) \frac{\partial e}{\partial K_{1TM}}$$

$$= \gamma \left[\frac{T_{2TM}(k)}{T_{1TMnominal}(k)}\right]^2 \left[\frac{1}{K_{1TM}(k)}\right]^3$$

Where $\gamma$ is an adaption scaling factor that governs the aggressiveness level of the adaptation, and needs to be tuned a priori. Taking a backwards difference approximation to discretize the above equation, the following difference equation that governs the time evolution of $K_{1TM}$ is obtained:

$$K_{1TM}(k) = K_{1TM}(k-1) + \frac{\gamma}{\delta}\left[\frac{T_{2TM}(k)}{T_{1TMnominal}(k)}\right]^2 \left[\frac{1}{K_{1TM}(k)}\right]$$

where $\delta$ is the sample time of the calculation. To avoid the need to solve for the root of a quadratic equation, a time delayed approximate can be used:

$$K_{1TM}(k) = K_{1TM}(k-1) + \frac{\gamma}{\delta}\left[\frac{T_{2TM}(k)}{T_{1TMnominal}(k)}\right]^2 \left[\frac{1}{K_{1TM}(k-1)}\right]$$

The three embodiments described above are based on the assumption that the main source of inaccuracy of the one-thermistor model is predominately a gain error. If an offset error is assumed, the same concepts described in the embodiments above can be implemented with a slight modification. For example, one would assume:

$$T_{1TM}(k) = D_{1TM}(k) + T_{1TMnominal}(k)$$

where the offset difference $D_{1TM}$ can be corrected by the following windowed comparison between the nominal one-thermistor model and two-thermistor model approaches.

$$D_{1TM}(k) := \sum_{j=0}^{N-1} T_{2TM}(k-j) - \sum_{j=0}^{N-1} T_{1TMnominal}(k-j)$$

The final ambient-compensated temperature may then be used, for example, to determine a temperature-compensated signal, as represented by block 1035. The corresponding analyte (e.g., glucose) level may then be transmitted or displayed, as represented by block 1040.

In addition, given that two thermistors are available, the above embodiments can be implemented on both thermistors such that instead of using a single modified one-thermistor model, an average of two modified one-thermsitor model outputs is used.

Again, as similarly stated above, it should be appreciated that the embodiment shown in FIG. 9 is exemplary, and that one or more steps may be performed by a processor on the on-body unit and/or a receiver in communication with the on-body unit in other embodiments. For example, in certain embodiments, the temperature sensors are coupled to the on-body unit and a processor on the on-body unit samples the temperatures sensors, determines the ambient-compensated temperature from the one-temperature sensor model and two-temperature sensor model, determines the correction factor or gain, determines the final ambient-compensated temperatures. The processor on the on-body unit may then either determine the temperature-compensated signal, or transmit the final ambient-compensated signal to a receiver having a processor that determines the temperature compensated signal and presents the corresponding analyte level on a user interface. It should be appreciated that these embodiments are exemplary, and that the steps may be split up in other combinations between the on-body unit and the receiver. For example, in other embodiments, one or more of the steps in determining the ambient-compensated signal and/or final ambient compensated signal may be performed by the receiver.

Provided below is an example analysis. It should be appreciated that the example analysis is exemplary and is not meant to be limiting.

Example Analysis:

Using the temperature sensor close to the skin, the equation for sensor (skin) temperature becomes:

$$T = 0.25*Tc + 0.75*T1$$

wherein Tc is the body core temperature 37 degrees C. and is treated as a constant.

Using the temperature sensor on the PCB, the equation for sensor (skin) temperature becomes:

$$T = 0.54*Tc + 0.46*T2$$

If the core temperature is 37 degrees C., these two equations will correct for the ambient effect. Further, the intrinsic measurement error in T1 or T2 is not amplified (like with the two temperature sensors implementation), but rather attenuated a bit.

Moreover, if the core body temperature does deviate from 37 degrees C., the resulting error is not significant, and further does not depend on the ambient temperature. For example, the following data was found:

For the temperature sensor close to the skin (T1): The resulting error, Terr, is 0.25 degrees C. per degree deviation from 37 degrees C.

| Tc | Terr | Glucose Error (assume F = 105 rather than 1.07) |
| --- | --- | --- |
| 36 | 0.25 | −1.2% |
| 37 | 0 | 0% |
| 38 | −0.25 | 1.2% |
| 39 | −0.5 | 2.5% |
| 40 | −0.75 | 3.7% |

For the temperature on the PCB (T2), the resulting error is only modestly worse; Terr, is 0.5 degrees C. per degree deviation from 37 degrees C.

| Tc | Terr | Glucose Error (assume F = 105 rather than 1.07) |
| --- | --- | --- |
| 36 | 0.54 | −2.6% |
| 37 | 0 | 0% |
| 38 | −0.54 | 2.6% |
| 39 | −1.08 | 5.5.4% |
| 40 | −1.62 | 8.2% |

Temperature Sensors Disposed Adjacent the Sensing Area

In some aspects of the present disclosure, an on-body sensor is provided with a temperature sensor disposed on the analyte sensor adjacent to the sensing area (e.g., at sensor tip on the sensor tail). In such case, extrapolation is not required to determine the temperature value at the sensing area. This may provide one or more benefits, such as less data required to be transmitted to the controller, promoting shorter RF packets and longer battery life, reducing complexity of system software, etc.

In some aspects of the present disclosure, embedded temperature sensors are provided. The term "embedded temperature sensor" is used herein to mean a temperature sensor that is disposed on an analyte sensor such that it is exposed to body fluids (e.g., interstitial fluids) when the analyte sensor is positioned in vivo.

An embedded temperature sensor enables the temperature of the interstitial fluid itself to be measured. In this way, the temperature at the location of the sensor chemistry of in vivo analyte sensors may be measured. Since the sensing chemistry is within interstitial fluid, a measurement of the interstitial fluid temperature provides a very accurate temperature measurement for the sensing area.

In certain aspects of the present disclosure, the embedded temperature sensors are resistive temperature detection (RTD) devices. RTDs are devices which increase in electrical resistance with increasing temperature. Temperature may be measured, for example, by driving a reference current through the device and measuring the voltage across the device. Platinum provides high accuracy, linearity, and stability when used as an RTD. It should be appreciated that other materials (e.g., metals or metal-alloys, etc.) may be used as an RTD.

As a non-limiting example, a platinum RTD may have a nominal resistance at 0 degrees C. and a temperature coefficient of 0.00385Ω/Ω/degrees C. The nominal 0 degrees C. resistance may range from 100Ω to 500Ω, for example, depending on construction. The absolute resistance of the RTD at any given temperature T determined as follows:

$$RTD(T)=RTD_0+T*0.00385\Omega/\Omega/\text{degrees C.}$$

where RTD(T) is equal to the absolute RTD resistance in Ohms; $RTD_0$ is equal to the resistance of the RTD at 0 degrees C. in Ohms; and T is equal to the temperature in degrees C. And further, the linearity of the platinum RTD may, for example, be less than +/−0.5% from 0-100 degrees C.

In certain embodiments, platinum is used as a sensor conductive base material to form an electrode that is also an embedded RTD. The platinum RTD trace may be made by any variety of manufacturing processes. For example, laser ablation may be used to create the electrodes and accommodate very fine feature sizes, as well as allow for a long platinum RTD trace to increase its resistance.

Figure 10:
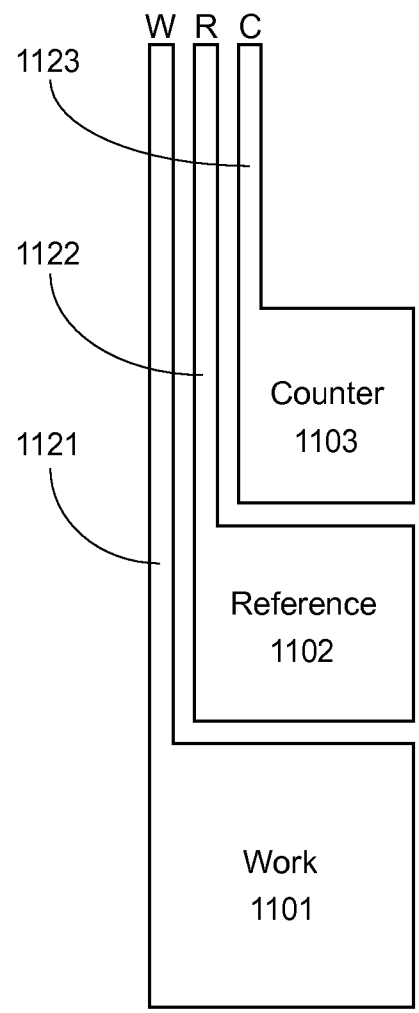
FIG. 10 illustrates an electrode arrangement for a typical three-terminal sensor, according to certain embodiments.

FIG. 10 illustrates an electrode arrangement for a typical three-terminal sensor, according to certain embodiments. The subcutaneous tail of a three-terminal analyte sensor is shown including a working electrode 1101, reference electrode 1102, and counter electrode 1103. Each of the three electrodes 1101, 1102, 1103 has a single electrical trace 1121, 1122, 1123, respectively, that extends from the along the sensor tail towards the electronics in the on-body sensor. The electrical traces provide the electrical communication path between the corresponding electrodes and electronics in the on-body sensor.

Figure 11:
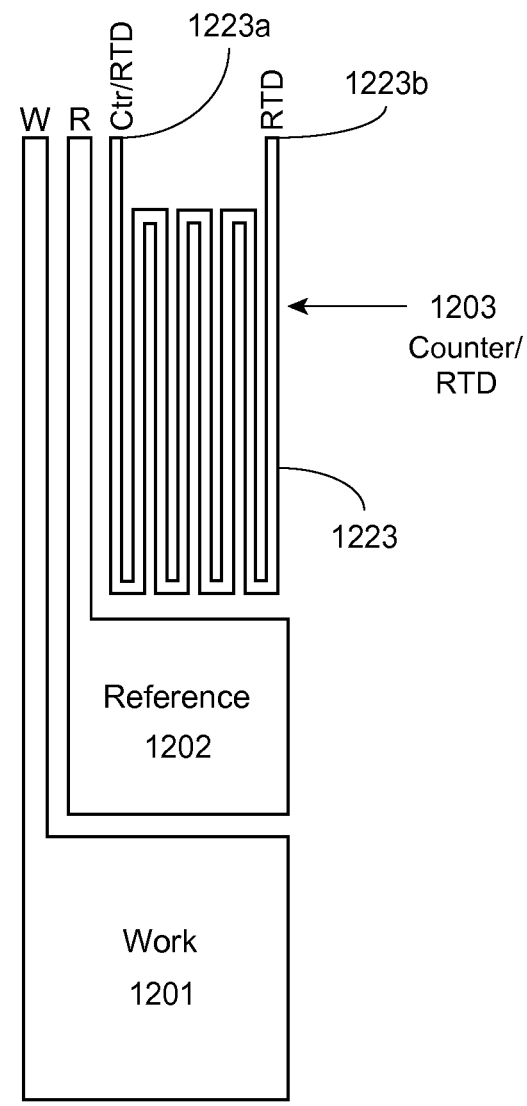
FIG. 11 illustrates an electrode arrangement for a three-terminal analyte sensor wherein one of the electrodes is also an embedded RTD, according to certain embodiments.

FIG. 11 illustrates an electrode arrangement for a three-terminal analyte sensor wherein one of the electrodes is also an embedded RTD, according to certain embodiments. The subcutaneous tail of the three-terminal analyte sensor is shown including a working electrode 1201 and reference electrode 1202, as well as a counter electrode 1203 that is also an embedded RTD. When the sensor is positioned in vivo into the skin of the subject, the embedded RTD and electrode 1203 is embedded in the subject and exposed to interstitial fluid.

The embedded RTD and electrode 1203 includes an electrical trace having two ends 1223a, 1223b such that current can be applied to the RTD and voltage measured across the two ends 1223a, 1223b. In the embodiment shown, the embedded RTD and electrode 1203 is a single electrical trace 1223 that extends back and forth longitudinally to increase the distance of the electrical trace. A long trace increases resistance and facilitates a better measurement. In certain embodiments, a long platinum RTD trace is used to increase its resistance and facilitate a better measurement.

Figure 12:
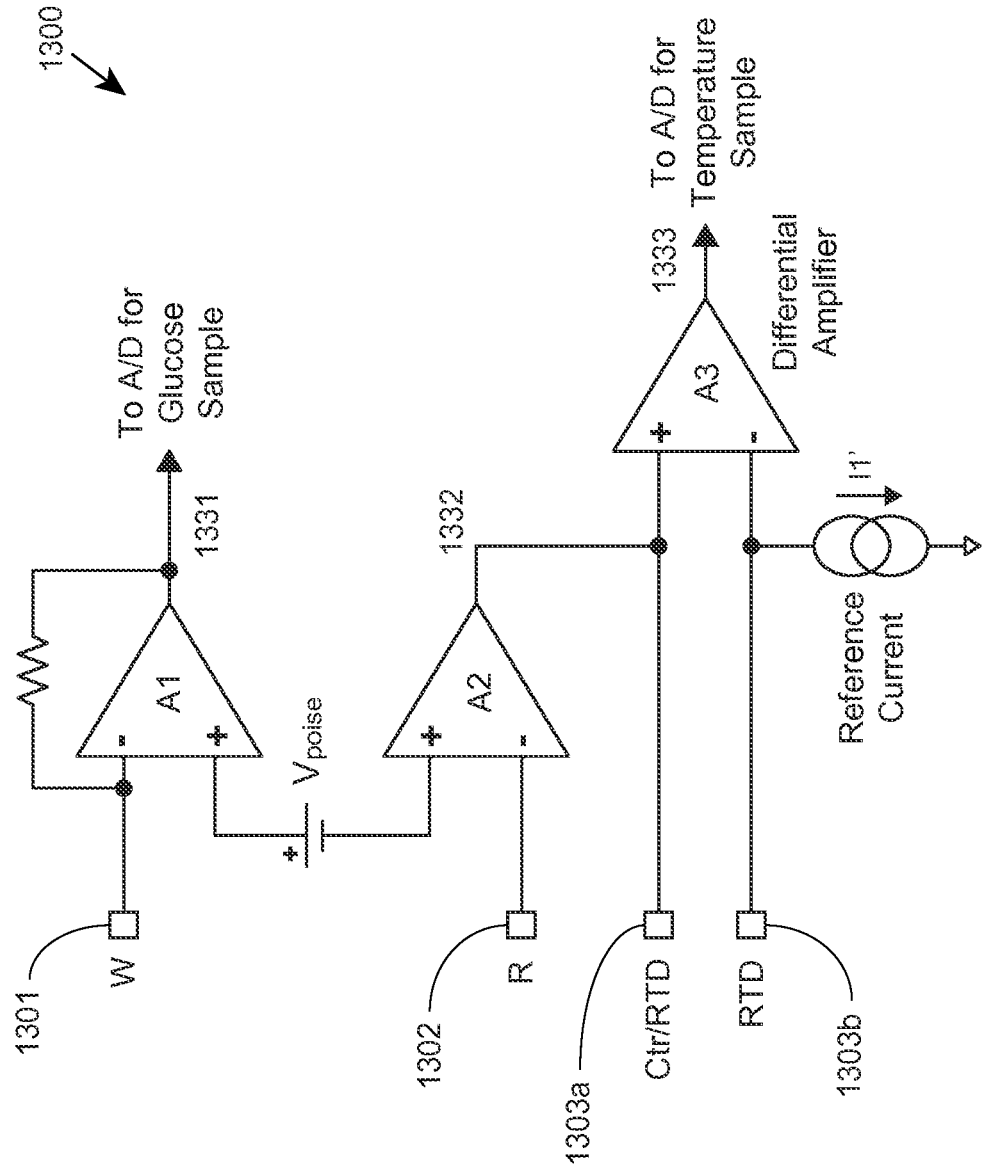
FIG. 12 illustrates a partial circuit diagram for an example analog front-end circuit for a three-terminal analyte sensor with one of the electrodes as an embedded RTD, according to certain embodiments.

FIG. 12 illustrates a partial circuit diagram for an example analog front-end circuit for a three-terminal analyte sensor with one of the electrodes as an embedded RTD, according to certain embodiments. As shown, analog front-end 1300 includes a working electrode contact point 1301 (e.g., to electrically couple to working electrode 1201 in FIG. 11) and a reference electrode contact point 1302 (e.g., to electrically couple to reference electrode 1202 in FIG. 11). Analog front-end 1300 also includes contact points 1303a, 1303b. Contact point 1303a electrically couples to the counter electrode of the analyte sensor and also serves as one end of the embedded RTD (e.g., end 1203a in FIG. 11). Contact point 1303b serves as a contact point that electrically couples to the other end of the embedded RTD (e.g., end 1203b in FIG. 11).

Analog front-end also includes amplifiers A1, A2 that are electrically coupled to the working and reference electrodes to provide the condition analyte signal 1331 for sampling by an A/D converter (not shown). Contact point 1303a is electrically coupled to the inverting input of amplifier A3. Contact point 1303b is electrically coupled to the non-inverting input of differential amplifier A3 along with the output 1332 of amplifier A2. Amplifier A3 measures the voltage across the RTD which is created by the flow of current provided through the RTD, as indicated by reference current, I1. The output 1333 of amplifier A3 provides the temperature signal to the A/D converter for the temperature sample.

It should be appreciated that other circuit elements may also be implemented to the analog front-end 1300—e.g., to improve performance, such as a reference resistor for the reference current to flow through, which could eliminate temperature and other errors in the A/D converter.

It should also be appreciated that in other embodiments, the embedded RTD could be implemented as one of the other electrodes—e.g., the reference electrode or working electrode. Furthermore, it should also be appreciated that an embedded RTD may be implemented in an analyte sensor with a different number of electrodes than three—e.g., a two-electrode sensor. For example, a two-electrode sensor may have a working electrode as well as a reference electrode that is also an embedded RTD.

It should be appreciated that the shape of the embedded RTD and electrode may vary in other embodiments. For example, in other embodiments, the embedded RTD and electrode may extend back and forth longitudinally a number of times that is different than shown in FIG. 11. Or alternatively, for example, the embedded RTD and electrode may extend back and forth latitudinally, or both latitudinally and longitudinally. It should be appreciated that in other embodiments, any variety of patterns and designs may be used for the shape of the embedded RTD and electrode, as long as the counter electrode has sufficient surface area exposed to the interstitial fluid. Moreover, the position of the two ends of the embedded RTD and electrode may also vary in different embodiments.

Temperature Sensors and Analyte Sensor Devices Having Elongated Members with Central Tunnels In some aspects of the present disclosure, analyte sensor devices are provided that include a body having an elongated member (e.g., a hollow tube) with a central tunnel therein. Electrodes are disposed on the outside of the body and a temperature sensor coupled to the body. In certain embodiments, the central tunnel houses a temperature sensor. In this way, the temperature sensor provides a direct temperature measurement at the analyte sensor tip.

For example, in certain embodiments, a needle is disposed within the central tunnel during insertion. In certain embodiments, the sharp is withdrawn and a temperature sensor is inserted into the central tunnel of the hollow tube. The inserted temperature sensor may then provide temperature measurements at the analyte sensor tip.

In certain embodiments, the temperature sensor is adapted to pierce the skin and serve as the needle. For example, the temperature sensor may be formed as the needle, formed as part of the sharp, or coupled to a needle. In some instances, the temperature sensor is adapted to pierce the skin of the subject and is softened by exposure to body fluids—e.g., made from or include a material that softens when exposed to body fluids. In this way, the sharp softens when inserted into the subject and does not become an irritant.

In certain embodiments, the on-body housing of the analyte sensor device is adapted to couple to an insulin delivery tube and insulin pump. For example, the analyte sensor device may serve as an insulin delivery cannula. In such case, the analyte sensor device functions as an analyte monitoring system and integrated insulin delivery cannula.

In certain embodiments two conductors, such as wires or conductive plastic, are extruded in the walls of the insulin delivery cannula. One of the wires acts as a reference electrode for the analyte (e.g., glucose) sensing function. For example, in some instances, the one wire may be made from silver or other suitable conductor with or without a coating, and the second wire made from either gold or other highly conducting material. Both wires are fully embedded into the walls of the cannula (e.g., a soft cannula) and would extend near the tip of the cannula. At or near the tip of the cannula, each of the two wires terminates at a feature that allows the wires to electrochemically communicate with tissue and body fluids in conjunction with appropriate chemical or biological materials. For instance, the silver wire could be plated or chemically chloridized with silver chloride to form an Ag/AgCl reference electrode or auxiliary electrode in a two electrode system. The other wire may be, for example, coated or deposited with glucose sensing chemistry to form a working electrode. In some instances, either or both electrodes may be covered by a thin layer of membrane to restrict the glucose flux as well as to protect the electrode components. Further, in some instances, a section of the cannula may be laser ablated or chemically etched to increase the surface area of the active working or reference electrode.

In certain embodiments, a thermocouple is extruded into the insulin delivery cannula. For example, the thermocouple may be co-extruded into an insulin delivery cannula such as described above. The thermocouple may be co-extruded with the other materials in order to provide temperature sensing at the location of interest at the implanted site—e.g., close to the sensing chemistry.

In certain embodiments, the dual function soft cannula may be attached to a housing and adhesive patch to facilitate retention on the skin. The housing may include the additional components needed for continuous glucose sensing—e.g., a thermistor or thermocouple for skin temperature measurement and a counter electrode to return electrons to the body to form a closed sensor circuit. The wires of these two components may be molded inside the plastic cannula housing, for example. These wires along with the two electrode wires may be exposed at the distal end of the cannula and arranged around a keyed fluid and electrical connecting point. The connection point allows all wires to be connected to their counterparts embedded inside a connector on a multi conducting insulin delivery tube, for instance, when the cannula is connected to the tube.

In certain embodiments, the wires for the thermistor or thermocouple for skin temperature measurements and a wire to act as a counter electrode is extruded or embedded into the cannula, creating a multi-function structure.

The wires embedded inside the wall of the insulin delivery tubing enable a dual function device that delivers insulin and provides continuous glucose monitoring support functionality such as sensor signal transduction, calibration and user interface. The integrated system described above may be attached to or worn on the body.

In certain embodiments, the integrated system may include an insulin delivery pump, the CGM system, the data collection and processing hardware, and the user interface including control buttons and display. In some instances, the system may also have a discrete glucose meter embedded in it so that the user can check the blood glucose with the system using test strips.

In certain embodiments, the hardware of the insulin delivery pump and the continuous glucose monitor are combined into a more compact assembly and attached to the body using an adhesive patch. Other components (data processing algorithms, user interface, and/or discrete glucose meter, etc.) may, for example, be integrated into a separate controller that communicates with the assembly wirelessly. This embodiment may significantly improve usability of the system.

Thermocouples

In some aspects of the present disclosure, ambient temperature compensation is provided using a thermocouple temperature sensor. The thermocouple temperature sensors are included of dissimilar metals—e.g., metal-inks. Example metals may include, but are not limited to, gold, silver, carbon, titanium, and alloys thereof.

The physical properties of the dissimilar metals create a thermocouple temperature sensor at the junction of the dissimilar metals. A small voltage that is dependent on temperature will exist between the dissimilar metals. The voltage produced by a thermocouple is known and predictable based on the properties of the two dissimilar metals. Measurement of this voltage results in data that can be used to accurately determine the temperature of the analyte sensor (e.g., glucose sensor). For example, measurement of this small signal can be performed by the electronics located in the on-body unit—e.g., in the transmitter of the on-body unit.

For example, in certain embodiments, calibration can be done by applying two different voltages to a measurement circuit and computing the zero point and scale of the measurement circuit. This method may in some instances, include one or more benefits—e.g., cost, accuracy, and speed. For example, thermocouple sensors can be manufactured very inexpensively and may be conducive to high volume processing.

In certain embodiments, the thermocouple is created by depositing two different metals onto the analyte sensor tail and joining them at a junction located close to the actual sensing area. For example, the metals may be deposited onto the analyte sensor substrate by any variety of methods, such as, but not limited to, sputtering, electroplating, or using a metallic ink. In some instances, the thermocouple may be constructed using metal wire.

The two traces of different metals are electrically conducted ("bonded") to form the junction. Having the junction adjacent to the actual sensor active area provides a temperature measurement close to the sensing area, resulting in an accurate measurement.

In certain embodiments, the thermocouple is formed on the same side of the analyte sensor as the sensing area (e.g., glucose sensing area). In other embodiments, the thermocouple is formed on the opposite side of the analyte sensor as the sensing area.

Figures 13, 14:
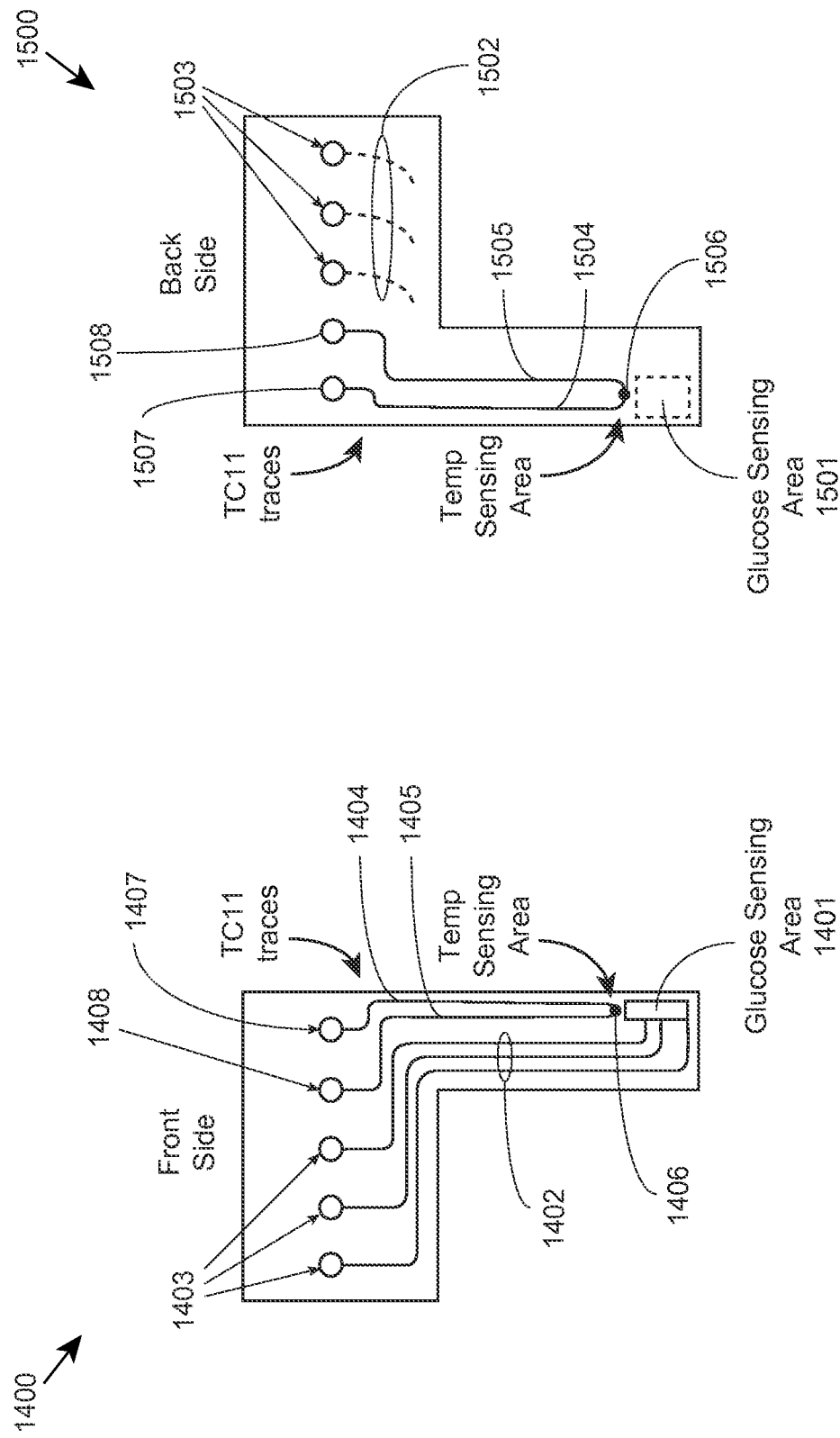
FIG. 13 illustrates a front-side view of an analyte sensor having thermocouple temperature sensor, according to certain embodiments.
FIG. 14 illustrates a back-side view of an analyte sensor having thermocouple temperature sensor, according to certain embodiments.

FIG. 13 illustrates a front-side view of an analyte sensor having thermocouple temperature sensor, according to certain embodiments. The analyte sensor 1400 shown is a glucose sensor having a glucose sensing area 1401 including three electrodes—e.g., working electrode, reference electrode, and counter electrode. Electrical traces 1402 extend from the electrodes in the sensing area 1401 to corresponding contact points 1402 for connection to the electronics in the on-body sensor.

Glucose sensor 1400 also includes two traces 1404, 1405. Trace 1404 and 1405 are made of dissimilar materials (e.g., different metals or metal-alloys) that extend from corresponding contact points 1407, 1408, respectively, to a junction point 1406 located next to the glucose sensing area 1401. Contact points 1407, 1408 provide electrical connection to the electronics on the on-body sensor for measurement of the voltage produced by the junction of dissimilar materials.

In the embodiment shown, the two traces 1404, 1405 of dissimilar materials are on the same side (e.g., front side) of the glucose sensor 1400, and further are on the same side of the sensor 1400 as the glucose sensing area 1401 and electrode traces 1402. While the distance between the junction point 1406 and the glucose sensing area 1401 may vary in different embodiments, having the junction point 1406 closer to the glucose sensing area 1401 provides a more accurate temperature estimate at the glucose sensing area 1401. Some space is needed to provide distance between the junction point 1406 and the glucose sensing area 1401 for insulation between the two.

FIG. 14 illustrates a back-side view of an analyte sensor having thermocouple temperature sensor, according to certain embodiments. The analyte sensor 1500 shown is a glucose sensor having a glucose sensing area 1501 including three electrodes—e.g., working electrode, reference electrode, and counter electrode. Electrical traces 1502 extend from the electrodes in the sensing area 1501 to corresponding contact points 1502 for connection to the electronics in the on-body sensor.

Glucose sensor 1500 also includes two traces 1504, 1505. Trace 1504 and 1505 are made of dissimilar materials (e.g., different metals or metal-alloys) that extend from corresponding contact points 1508, 1509, respectively, to a junction point 1506 located next to the glucose sensing area 1501. Contact points 1507, 1508 provide electrical connection to the electronics on the on-body sensor for measurement of the voltage produced by the junction of dissimilar materials.

In the embodiment shown, the two traces 1504,1505 of dissimilar materials are on the opposite side (e.g., back side) of the glucose sensor 1500 than the glucose sensing 1501 and electrode traces 1402 (e.g., on the front-side).

While the position of the junction point 1506 relative to the glucose sensing area 1501 may vary in different embodiments, having the junction point 1506 closer to the glucose sensing area 1501 provides a more accurate temperature estimate at the glucose sensing area 1501. In the embodiment shown, the junction point 1506 and the glucose sensing area 1501 are insulated from one another by the substrate itself, allowing the two traces 150 to extend further along the analyte sensor (e.g., directly opposite the glucose sensing area 1501).

It should be appreciated that in certain embodiments one of the two thermocouple traces could be made of the same material as the electrode traces. It should also be appreciated that in other embodiments one of the thermocouple traces may be on the opposite side of the sensor as the other thermocouple trace with a junction point near the glucose sensing area (e.g., implemented using a through-hole via).

In certain embodiments, the thermocouple sensor includes dissimilar metal traces on facing sides of two pieces of substrate (e.g., Kapton or another type of Polymer) that adhere together. In such case, the sensor is electrically isolated from the body as well as not crowding or disturbing the glucose sensing traces since the thermal sensing traces would be on a different plane. It should be appreciated that each of the dissimilar metals may be disposed on either inner facing side of the two pieces of substrate, independent of one another, such that a junction point is formed when the two pieces of substrate are combined. For example, one dissimilar metal may be one facing side while the other dissimilar metal is on the other facing side, and when the two facing sides are brought together, the two dissimilar metals forming a thermocouple junction point. This also applies to the other sensor concepts described herein as well.

Figure 15:
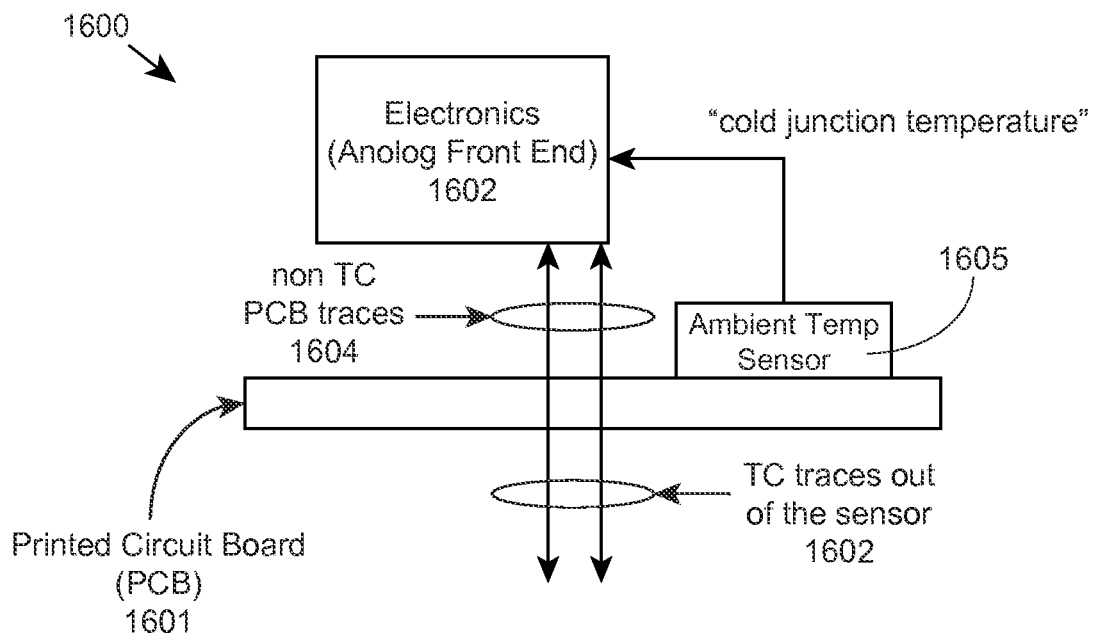
FIG. 15 illustrates a system block diagram of an on-body sensor having a thermocouple temperature sensor, according to certain embodiments.

FIG. 15 illustrates a system block diagram of an on-body sensor having a thermocouple temperature sensor, according to certain embodiments. On-body sensor 1600 includes a printed circuit board (PCB) 1601 having various electronic components thereon, including, for example, the analog front-end circuitry 1602. The thermocouple traces 1602 on the analyte sensor terminate on the PCB 1601 at contact points 1603 that are electrically coupled to non-thermocouple traces 1604 disposed on the PCB 1601. The non-thermocouple traces 1604 electrically couple the thermocouple traces 1602 to the analog front-end circuitry 1602 for measuring the voltage providing by the thermocouple.

In certain embodiments, such as shown, an ambient temperature sensor 1605 generates a signal that is used for "cold junction temperature" compensation in the system. In some instances, the "cold junction" temperature sensor 1605 is positioned at the point that the dissimilar metal traces 1602 are connected to the PCB 1601 in the on-body device. The voltage that is measured at the cold junction is a function of the temperature differential between the cold junction and the bonding point.

Thermocouple tape having two dissimilar metals is described in U.S. Pat. No. 3,729,343, filed on Jan. 8, 1971 and issued on Apr. 24, 1973, the entirety of which is hereby incorporated by reference.

In some aspects of the present disclosure, an analyte sensor is provided having a sensor substrate that includes two dissimilar materials on opposite sides with a thermocouple junction formed by a through-hole within the substrate.

In certain embodiments, a metal (or metal-alloy) trace is disposed on one side of the sensor substrate and a thermocouple trace (e.g., a conductive ink layer) on the opposite side of the substrate. A thermocouple junction is formed between the metal trace on one side and the conductive ink layer on the opposite side by a through-hole (e.g., a laser-drilled hole in the substrate). The conductive ink is disposed in the through-hole and forms a thermocouple junction between the metal trace on one side of the substrate and the conductive ink on the opposite side of the substrate. The conductive ink material may be made from any variety of materials suitable for creating a thermocouple junction—such as metal or metal alloys including, but not limited to, platinum, carbon, copper, iron, silver, etc.

In some aspects of the present disclosure, methods of making the above-mentioned thermocouple are provided. The methods include forming a metal or metal-alloy layer (e.g., a film plated with the metal or metal-alloy) on a sensor substrate; removing a portion of the metal or metal-alloy layer (e.g., by forming a laser-drilled hole); forming a conductive ink layer (e.g., a conductive ink trace) on the opposite side of the substrate as the metal or metal-ally layer; filling the through-hole with the conductive ink such that a thermocouple junction is formed between the conductive ink layer and the metal layer.

In certain embodiments, the metal or metal-alloy layer is also a sensor electrode. It should be appreciated that the conductive ink may be applied to the sensor substrate at various times. For example, in certain embodiments, the conductive ink layer may be applied before the through-hole is formed and again applied afterwards to fill the through-hole. In other embodiments, the conductive ink is applied after the through-hole to form the conductive ink layer and fill the through-hole.

Figure 16:
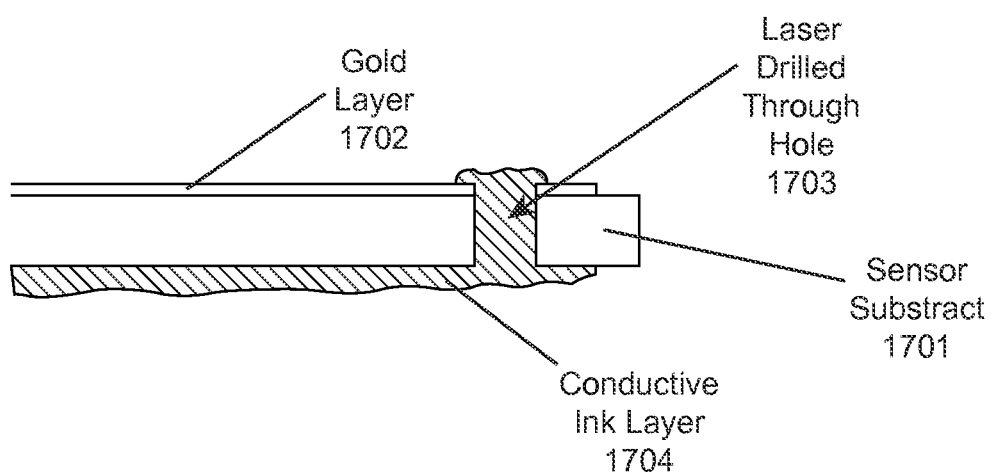
FIG. 16 illustrates a cross-sectional view of an analyte sensor substrate having a thermocouple junction, according to certain embodiments.

FIG. 16 illustrates a cross-sectional view of an analyte sensor substrate having a thermocouple junction, according to certain embodiments. The sensor substrate 1701 includes a layer of gold 1702 on one side of the substrate 1701. A through-hole 1703 is formed (e.g., via laser drilling) in the sensor substrate 1701 such that a portion of the layer of gold 1702 is removed. It should be appreciated that in other embodiments, the portion of the layer of gold 1702 at the through-hole may be removed before the laser drilled through-hole is formed—e.g., via an etching process, etc.—or otherwise disposed on the substrate 1701 in a printed pattern.

As shown in FIG. 16, a conductive ink layer 1704 is disposed on the opposite side of the sensor substrate 1701 as the layer of gold 1702. The through-hole 1703 is filled with the conductive ink such that the conductive ink layer 1703 and layer of gold 1703 are connected and a thermocouple junction formed.

Provided below is an example analysis. It should be appreciated that the example analysis is exemplary and is not meant to be limiting.

Example Analysis:

The following analysis is provided for exemplary purposes and is not meant to be limiting. The following analysis is based on the following: a sensor temperature range of 32 degrees C. to 42 degrees C. (typical body temperature of 37 degrees C.+/−5 degrees C.); a cold junction temperature range of 10 degrees C. to 50 degrees C.; thermocouple op amp similar to operation amplifier, OPA333, manufactured by Texas Instruments; an analog to digital converter (ADC) with a resolution less than 0.1 degrees C. and input voltage range of 0 to 400 mV; a modulator clock of 32768 Hz and conversion time of 125 mS (12 Bits); thermocouple sensitivity of 40.7 µV/degrees C. (e.g., type T Cu-Cn).

The analysis was also based on the OPA333 operation amplifier having the following features: low offset voltage of 10 µV(max); zero drift of 0.05 µV/° C. (max); 0.01 Hz to 10 Hz noise of 1.1 µVpp; quiescent current of 17 µA; single-supply operation; supply voltage of 1.8V to 5.5V; rail-to-rail input/output; and microsize packages (SC70 and SOT23).

The results of the analysis were as follows: ADC 1 bit resolution=97.65 µV (12 bits—range of 400 mV); required minimum gain for thermocouple amplifier=2.4; maximum amplifier offset at ADC=24 µV (this is <1ADC count.); and type-T thermocouple output at 25.2C=1.000 mV. Any calibration for the ADC slope and offset variation may be done by applying a known voltage during manufacture, for example.

The actual gain may be chosen much higher than minimum. The signal as seen by the thermocouple amplifier is the combination of the cold junction thermocouple and the sensor tip thermocouple. Exact calculations depend on the Seebeck voltage of the materials chosen.

In some instances, the cold junction thermocouple may vary in a temperature range that is higher than the sensor tip thermocouple and also lower than the sensor tip thermocouple. In such case, provided the cold junction temperature is known and sensitivity of the cold junction TC is known, a subtraction can be made that eliminates the cold junction contribution.

In some instances, the method for cold junction compensation uses a precision thermistor and requires no calibration.

In certain embodiments, one of the existing sensor electrode conductors is used as one of the thermocouple connections. Having a thermocouple output that is a differential voltage allows the sensor electrode conductor to be used and avoid using two additional connections to the sensor.

In some instances, carbon-polymer contacts are used with a thermocouple amplifier having high impedance input (non-inverting). This method helps avoid some thermal gradient issue and provides a more direct sensor temperature measurement.

Types of Temperature Sensors:

It should be appreciated that any variety of temperature sensors may be applicable to the subject matter of the present disclosure. The following temperature sensors are exemplary and are not intended to be limiting.

Thermistor:

In some aspects of the present disclosure, a thermistor sensor may be used for temperature compensation. The thermistor sensor may be disposed, for example, on a sensor tail that is positioned under the skin or near the tip of the analyte sensor. Example thermistors that may be implemented include, but are not limited to, surface mounted thermistors of type 0402, 0201, or 0105. Other example may include, but are not limited to, glass beads types, epoxy bead types, or small chip thermistors.

In some aspects of the present disclosure, the thermistor sensor is located in a thermally conductive structure such that it protrudes from the bottom of the skin worn transmitter device and provides a low thermal resistance path from the user's skin to a thermistor located in the electronics.

Figure 17:
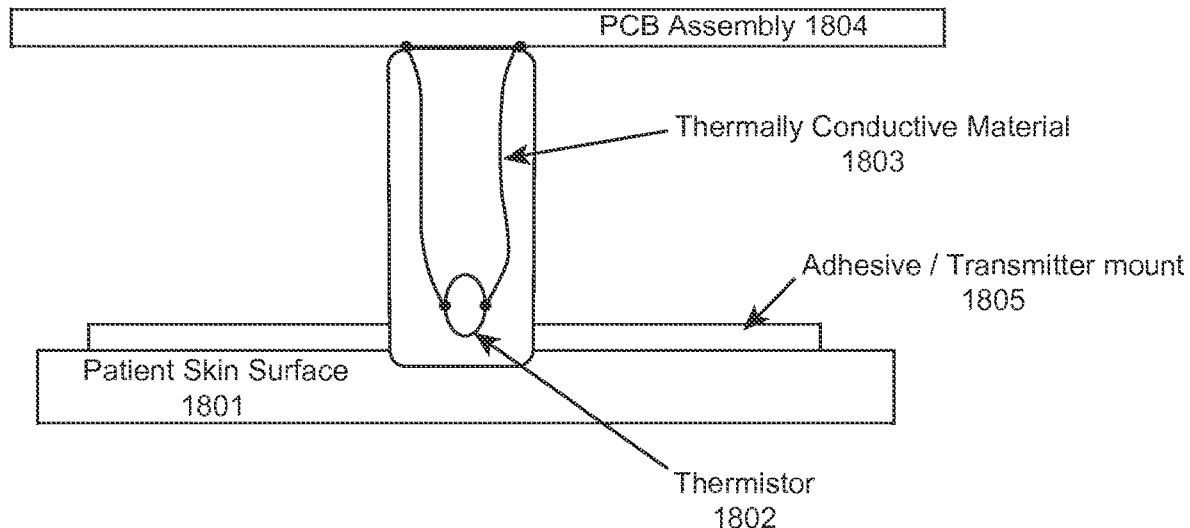
FIG. 17 illustrates an on-body sensor having a thermistor located in a thermally conductive structure such that it protrudes from the bottom of the on-body sensor, according to certain embodiments.

FIG. 17 illustrates an on-body sensor having a thermistor located in a thermally conductive structure such that it protrudes from the bottom of the on-body sensor, according to certain embodiments. On-body sensor 1800 is shown attached to a patient's skin surface 1801. The on-body sensor 1800 includes a thermistor 1802 that is disposed within a thermally conductive material 1803. The thermistor 1802 is electrically coupled to the on-body sensor's printed circuit board (PCB) 1804 for electrical coupling to the electronics on the PCB. The on-body sensor 1800 includes an adhesive layer 1805 that mounts the on body sensor 1800 to the patient's skin 1801. The thermally conductive material 1803 including the thermistor 1802 extends beyond the adhesive layer 1805 and protrudes from the on-body sensor 1800. The thermally conductive material 1803 contacts the skin 1801 of the patient to provide temperature measurement of the patient's skin 1801.

Resistive Temperature Device:

In some aspects of the present disclosure, a resistive temperature device (RTD) type sensor may be used for temperature compensation. For example, an RTD type sensor may be constructed from traces of metal (e.g., including, but not limited to, metals such as gold or platinum, or metal-alloys thereof) and deposited onto the sensor substrate. For instance, an RTD device such as a wire wound encapsulated device may be incorporated onto the sensor tail. The RTD device may then measure by the sensor electronics.

Pyro-Electric Sensor:

In some aspects of the present disclosure, a pyro-electric sensor may be used for temperature compensation. Pyro-electric sensors are sensitive to the infra-red light emitted by a warm object—e.g., the patients skin. In certain embodiments, an optical path is constructed from the patient's skin surface to the pyro-electric sensor that is located inside the electronics of the on-body unit. In this way, the skin surface temperature can be sensed and measured.

Semiconductor Sensor:

In some aspects of the present disclosure, a semiconductor sensor may be used for temperature compensation. In certain embodiments, a semiconductor sensor (such as, but not limited to, a diode junction or band gap type temperature sensor) is disposed (e.g., directly or disposed on a small device) either on the sensor tail or very close to the sensor insertion site to sense the glucose sensor temperature.

Temperature Compensation and Sensing Elements:

In some aspects of the present disclosure, analyte monitoring devices and systems include a sensing area that includes two or more sensing elements disposed on the sensing surface. For example, the sensing surface may be on a working electrode. Additional details regarding multiple sensing elements disposed on a sensing surface may be found in U.S. Provisional Patent Application No. 61/421,371, filed Dec. 9, 2010, the entirety of which is incorporated herein by reference.

In certain embodiments, more than one sensing element is disposed at the sensing area (e.g., sensor tip). As demonstrated above, temperature compensation may be performed when multiple sensing elements are at the sensor tip. Furthermore, it has been shown that very small sensing layer areas improve repeatability of the sensor sensitivity. Further, multiple sensing dots may promote the collection of sufficient current for generating a viable signal.

In certain embodiments, on-body sensors are provided having multiple sensing elements at the sensing area, wherein some of the sensing elements are made of a different material than other sensing elements. For example, some of the sensing elements are made of a first material and the other sensing elements are made of a second material. The different materials have different temperature responses. Thus, current from the sensing elements of one material may be collected and compared to the current from the sensing elements of the second material to determine the temperature at the sensor tip. In this way, a temperature measurement is performed almost directly at the sensor tip.

Figure 18:
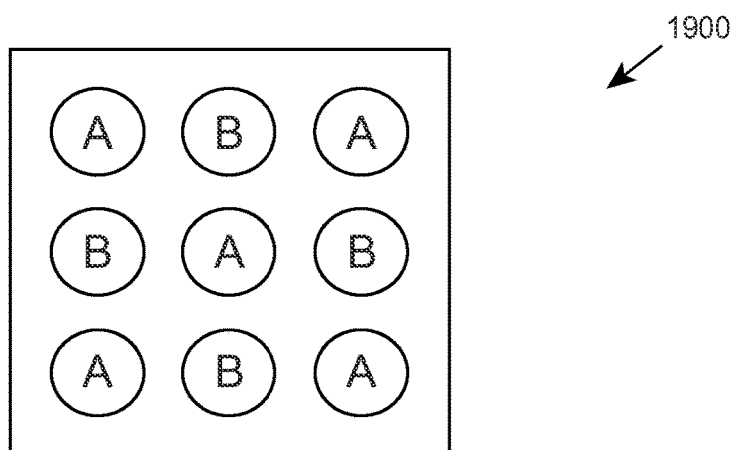
FIG. 18 illustrates a top view of multiple sensing elements disposed on a sensing surface, according to certain embodiments.

FIG. 18 illustrates a top view of multiple sensing elements disposed on a sensing surface, according to certain embodiments. Sensing surface 1900 is shown including sensing elements A and sensing elements B. Sensing elements A are made of a first material and sensing elements B are made from a different material than sensing elements A. The different materials (e.g., sensing chemistries) have different temperature dependencies and thus different temperature responses. Current from sensing elements A are compared to current from sensing elements B to determine the temperature at the sensor tip. In this way, a temperature measurement is performed almost directly at the sensor tip.

It should be appreciated that the number of sensing elements may vary in different embodiments. Further, it should also be appreciated that the sensing elements may be disposed on the sensing surface in a variety of shapes and patterns, and should not be limited to the embodiment shown in FIG. 18.

Temperature Compensation and Electrodes with Different Chemistries

In some aspects of the present disclosure, temperature compensation is performed when multiple working electrodes having different chemistries are present. For example, in some instances, an OBU may include a double sensor having different enzymes. For example, an on-body sensor may include two working electrodes having different sensing chemistries on each electrode. Because the sensing chemistry is different, their temperature dependencies are different. However, in a limited temperature range, the functional dependence is the same. Sensor current may be determined by, for example:

$$I \sim (1+a)^{(T-T_{nom})}$$

where I is the sensor current, a is a known positive constant much less than unity, and $T_{nom}$ is a set temperature. The sensor current also depends on the surface area, the amount of sensing material, and efficiency of the sensing chemistry and diffusion controlling membrane—collectively referred to herein as factor A. The ratio of the sensor currents is:

$$\frac{I_1}{I_2} = \frac{A_1(I+a_1)^{(T-T_{nom})}}{A_2(I+a_2)^{(T-T_{nom})}}$$

Solving for T:

$$T = T_{nom} + \frac{\ln(I_1/I_2) - \ln(A_1/A_2)}{\ln\left(\frac{I+a_1}{I+a_2}\right)}$$

All of the quantities on the rights side of the equation are, in principle, known. If A1 is set equal to A2, then I1=I2 when $T=T_{nom}$.

Once T is calculated, the sensor current is compensated for temperature and the analyte level calculated.

Temperature Compensation Using a Known Reservoir

In some aspects of the present disclosure, a secondary sensing element is used to directly measure the effect of temperature on the chemistry, independent of the user's analyte level (e.g., blood glucose). This measurement data is used in conjunction with measurement data from the primary sensor, which is dependent on temperature and the user's blood glucose, to remove the temperature effect. In this way, a more accurate estimate of the user's blood glucose concentration may be achieved. Moreover, temperature variation may be automatically compensated without implementing the mathematical model used in the some of the two sensor models described above, and instead use the chemistry to compensate itself.

In certain embodiments, an on-body sensor includes a secondary sensing element and a known volume of glucose at a known concentration (e.g., as provided by a "reservoir"). Having a secondary sensing element and a known volume of glucose at a known concentration (e.g., as provided by a "reservoir") enables temperature variation to be "cancelled out" without having to model the actual temperature variation of the chemistry. The secondary sensing element may be disposed under the skin, for example, and the secondary dot and reservoir isolated from the rest of the system. In some instances, the reservoir is physically small, but lasts for the entire sensor life.

In certain embodiments, this type of thermometer may be operated in two ways; in the linear range, and in saturation. In the linear range, the current is a function of the glucose concentration and the temperature. The glucose concentration as a function of time is calculated by keeping track of the total charge collected. This yields the expected current at the nominal temperature. Any difference between the expected current and the actual current may be attributed to temperature variation. In certain embodiments, a membrane is disposed between the sensing element and the reservoir for operation in the linear range.

In saturation, the current is determined solely by enzyme activity. Since this is a function of temperature, temperature variation may be measured directly. When operating in saturation, the membrane may be thinner, even if glucose concentrations should need to remain high.

In certain embodiments, the reservoir is kept away from the sensing element until the sensor has started, whether operating in either the linear range or saturation. In this way, any time limit to the stability of the sensing layer in a wet environment is accounted for. For example, a temporary barrier may be implemented that ceases to separate the second sensing area and the reservoir when the analyte sensor is transcutaneously positioned—e.g., a barrier that is broken, dissolved, or otherwise removed upon the insertion process.

In certain embodiments, the secondary sensor signal is an analog signal which controls the gain of the primary sensor circuit. The gain control may be linear since the secondary signal itself contains the complex non-linear variation that may be more difficult to model.

In certain embodiments, the secondary sensor signal is sampled and the primary signal gain modified in a software algorithm. The software algorithm may be executed by a processing device in the on-body electronics for example. The gain control may be linear since the secondary signal itself contains the complex non-linear variation that may be more difficult to model.

Provided below are example analyses related to using a known reservoir. The example analyses are exemplary and are not meant to be limiting.

Example 1

A sensing dot with an area of 0.01 square millimeter (1/10 the area of the primary sensing dot), and a cubical reservoir of side length 0.5 millimeters filled with 10 millimolar glucose solution starts with a current of 6 nA, and finishes with a current of 0.6 nA.

Example 2

$a = 6.02 \times 10^{23}$ molecules/mole
$q = 1.6 \times 10^{-19}$ C/molecules
T-122 hours=439,200 seconds (sensor life)
$\beta = 6$ nA/(mM/Liter)/mm$^2$ = 6 (A/meter$^2$)(1/(M/Liter)) = $10^{-23}$ (A/meter$^2$)(1/molecule)(Liter) = $10^{-26}$ (Amp)(m)/molecule

Example 3

Time Evolution of Glucose Concentration
N=# of molecules in reservoir
$dN/dt = -\alpha I$
$\alpha$ = molecules/(Amp×sec) = molecules/c = 1/q
n = #molecules/m$^3$ concentration
V = reservoir volume
$dn/dt = -I/(qV)$
$I = \beta An$
A = m$^2$ area of sensing dot
$dn/dt = -\beta An/(qV)$
$n(t) = n_0 \exp(-\beta An/(qV)) = n_0 \exp(-6.25 \times 10^{-8} At/V)$

Example 4

Time Constant vs Sensor Life:
$6.25 \times 10^{-8}$ (AT)/V ≈ 2
A = 10-8 m$^2$
T = $4.4 \times 10^5$ s
V ≈ 1.4×10-10 m3
Cube: 0.5 mm on a side
Maximum and Minimum Concentrations and Currents
$\beta = 0.6$ nA/(mM/Liter)
Maximum current $I_o = 6$ nA
Maximum concentration $n_o = 10$ mM/L
After 5 days (and 2 time constants) $I_f \approx 0.6$ nA It should be understood that techniques introduced above can be implemented by programmable circuitry programmed or configured by software and/or firmware, or they can be implemented entirely by special-purpose "hard-wired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

The term "logic", as used herein, can include, for example, special purpose hardwired circuitry, software and/or firmware in conjunction with programmable circuitry, or a combination thereof.

Electrochemical Sensors

Embodiments of the present disclosure relate to methods and devices for detecting at least one analyte, including glucose, in body fluid. Embodiments relate to the continuous and/or automatic in vivo monitoring of the level of one or more analytes using a continuous analyte monitoring system that includes an analyte sensor at least a portion of which is to be positioned beneath a skin surface of a user for a period of time and/or the discrete monitoring of one or more analytes using an in vitro blood glucose ("BG") meter and an analyte test strip. Embodiments include combined or combinable devices, systems and methods and/or transferring data between an in vivo continuous system and an in vivo system. In certain embodiments, the systems, or at least a portion of the systems, are integrated into a single unit.

An analyte sensor as described herein may be an in vivo analyte sensor or an in vitro sensor (i.e., a discrete monitoring test strip). Such a sensor can be formed on a substrate, e.g., a substantially planar substrate. In certain embodiments, the sensor is a wire, e.g., a working electrode wire inner portion with one or more other electrodes associated (e.g., on, including wrapped around) therewith. The sensor may also include at least one counter electrode (or counter/reference electrode) and/or at least one reference electrode or at least one reference/counter electrode.

Accordingly, embodiments include analyte monitoring devices and systems that include an analyte sensor at least a portion of which is positionable beneath the skin surface of the user for the in vivo detection of an analyte, including glucose, lactate, ketones, and the like, in a body fluid. Embodiments include wholly implantable analyte sensors and analyte sensors in which only a portion of the sensor is positioned under the skin and a portion of the sensor resides above the skin, e.g., for contact to a sensor control unit (which may include a transmitter), a receiver/display unit, transceiver, processor, etc. The sensor may be, for example, subcutaneously positionable in a user for the continuous or periodic monitoring of a level of an analyte in the user's interstitial fluid. For the purposes of this description, continuous monitoring and periodic monitoring will be used interchangeably, unless noted otherwise. The sensor response may be correlated and/or converted to analyte levels in blood or other fluids. In certain embodiments, an analyte sensor may be positioned in contact with interstitial fluid to detect the level of glucose, which detected glucose may be used to infer the glucose level in the user's bloodstream. Analyte sensors may be insertable into a vein, artery, or other portion of the body containing fluid. Embodiments of the analyte sensors may be configured for monitoring the level of the analyte over a time period which may range from seconds, minutes, hours, days, weeks, to months, or longer.

In certain embodiments, the analyte sensors, such as glucose sensors, are capable of in vivo detection of an analyte for one hour or more, e.g., a few hours or more, e.g., a few days or more, e.g., three or more days, e.g., five days or more, e.g., seven days or more, e.g., several weeks or more, or one month or more. Future analyte levels may be predicted based on information obtained, e.g., the current analyte level at time to, the rate of change of the analyte, etc. Predictive alarms may notify the user of a predicted analyte level that may be of concern in advance of the user's analyte level reaching the future predicted analyte level. This provides the user an opportunity to take corrective action.

FIG. 1 shows a data monitoring and management system such as, for example, an analyte (e.g., glucose) monitoring system 100 in accordance with certain embodiments. Aspects of the subject disclosure are further described primarily with respect to glucose monitoring devices and systems, and methods of glucose detection, for convenience only and such description is in no way intended to limit the scope of the embodiments. It is to be understood that the analyte monitoring system may be configured to monitor a variety of analytes at the same time or at different times.

Analytes that may be monitored include, but are not limited to, acetyl choline, amylase, bilirubin, cholesterol, chorionic gonadotropin, glycosylated hemoglobin (HbA1c), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times.

The analyte monitoring system 100 includes an analyte sensor 101, a data processing unit 102 connectable to the sensor 101, and a primary receiver unit 104. In some instances, the primary receiver unit 104 is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link 107, which may optionally be configured for bi-directional communication. Further, the data processing unit 102 may include a transmitter or a transceiver to transmit and/or receive data to and/or from the primary receiver unit 104 and/or the data processing terminal 105 and/or optionally a secondary receiver unit 106.

Also shown in FIG. 1 is an optional secondary receiver unit 106 which is operatively coupled to the communication link 103 and configured to receive data transmitted from the data processing unit 102. The secondary receiver unit 106 may be configured to communicate with the primary receiver unit 104, as well as the data processing terminal 105. In certain embodiments, the secondary receiver unit 106 may be configured for bi-directional wireless communication with each of the primary receiver unit 104 and the data processing terminal 105. As discussed in further detail below, in some instances, the secondary receiver unit 106 may be a de-featured receiver as compared to the primary receiver unit 104, for instance, the secondary receiver unit 106 may include a limited or minimal number of functions and features as compared with the primary receiver unit 104. As such, the secondary receiver unit 106 may include a smaller (in one or more, including all, dimensions), compact housing or embodied in a device including a wrist watch, arm band, PDA, mp3 player, cell phone, etc., for example. Alternatively, the secondary receiver unit 106 may be configured with the same or substantially similar functions and features as the primary receiver unit 104. The secondary receiver unit 106 may include a docking portion configured to mate with a docking cradle unit for placement by, e.g., the bedside for night time monitoring, and/or a bi-directional communication device. A docking cradle may recharge a power supply.

Only one analyte sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105. Multiple sensors may be positioned in a user for analyte monitoring at the same or different times. In certain embodiments, analyte information obtained by a first sensor positioned in a user may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The sensor 101 may be configured to at least periodically sample the analyte level of the user and convert the sampled analyte level into a corresponding signal for transmission by the data processing unit 102. The data processing unit 102 is coupleable to the sensor 101 so that both devices are positioned in or on the user's body, with at least a portion of the analyte sensor 101 positioned transcutaneously. The data processing unit may include a fixation element, such as an adhesive or the like, to secure it to the user's body. A mount (not shown) attachable to the user and mateable with the data processing unit 102 may be used. For example, a mount may include an adhesive surface. The data processing unit 102 performs data processing functions, where such functions may include, but are not limited to, filtering and encoding of data signals, each of which corresponds to a sampled analyte level of the user, for transmission to the primary receiver unit 104 via the communication link 103. In certain embodiments, the sensor 101 or the data processing unit 102 or a combined sensor/data processing unit may be wholly implantable under the skin surface of the user.

In certain embodiments, the primary receiver unit 104 may include an analog interface section including an RF receiver and an antenna that is configured to communicate with the data processing unit 102 via the communication link 103, and a data processing section for processing the received data from the data processing unit 102 including data decoding, error detection and correction, data clock generation, data bit recovery, etc., or any combination thereof.

In operation, the primary receiver unit 104 in certain embodiments is configured to synchronize with the data processing unit 102 to uniquely identify the data processing unit 102, based on, for example, an identification information of the data processing unit 102, and thereafter, to periodically receive signals transmitted from the data processing unit 102 associated with the monitored analyte levels detected by the sensor 101.

Referring again to FIG. 1, the data processing terminal 105 may include a personal computer, a portable computer including a laptop or a handheld device (e.g., a personal digital assistant (PDA), a telephone including a cellular phone (e.g., a multimedia and Internet-enabled mobile phone including an iPhone™, a Blackberry®, or similar phone), an mp3 player (e.g., an iPOD™, etc.), a pager, and the like), and/or a drug delivery device (e.g., an infusion device), each of which may be configured for data communication with the receiver via a wired or a wireless connection. Additionally, the data processing terminal 105 may further be connected to a data network (not shown) for storing, retrieving, updating, and/or analyzing data corresponding to the detected analyte level of the user.

The data processing terminal 105 may include a drug delivery device (e.g., an infusion device), such as an insulin infusion pump or the like, which may be configured to administer a drug (e.g., insulin) to the user, and which may be configured to communicate with the primary receiver unit 104 for receiving, among others, the measured analyte level. Alternatively, the primary receiver unit 104 may be configured to integrate an infusion device therein so that the primary receiver unit 104 is configured to administer an appropriate drug (e.g., insulin) to users, for example, for administering and modifying basal profiles, as well as for determining appropriate boluses for administration based on, among others, the detected analyte levels received from the data processing unit 102. An infusion device may be an external device or an internal device, such as a device wholly implantable in a user.

In certain embodiments, the data processing terminal 105, which may include an infusion device, e.g., an insulin pump, may be configured to receive the analyte signals from the data processing unit 102, and thus, incorporate the functions of the primary receiver unit 104 including data processing for managing the user's insulin therapy and analyte monitoring. In certain embodiments, the communication link 103, as well as one or more of the other communication interfaces shown in FIG. 1, may use one or more wireless communication protocols, such as, but not limited to: an RF communication protocol, an infrared communication protocol, a Bluetooth enabled communication protocol, an 802.11x wireless communication protocol, or an equivalent wireless communication protocol which would allow secure, wireless communication of several units (for example, per Health Insurance Portability and Accountability Act (HIPPA) requirements), while avoiding potential data collision and interference.

Figure 2:
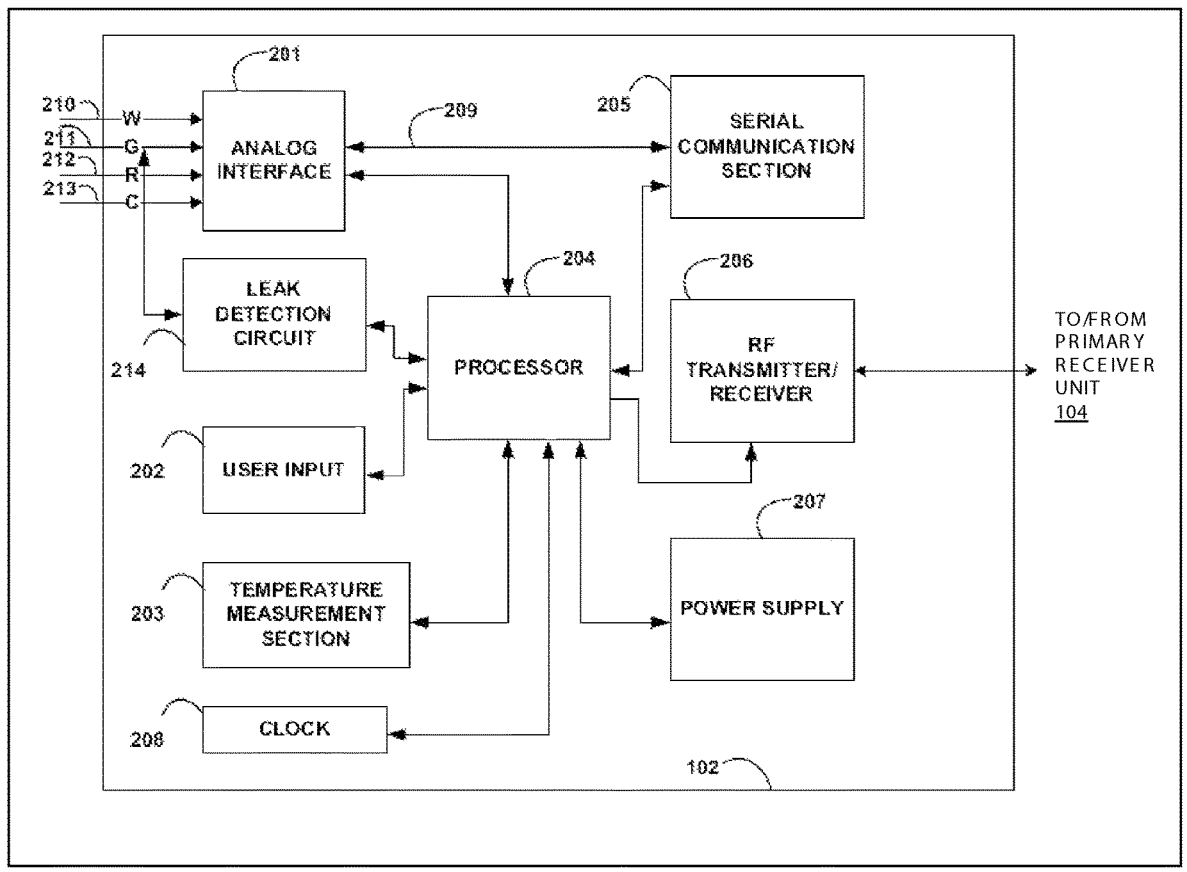
FIG. 2 shows a block diagram of an embodiment of a data processing unit of the analyte monitoring system shown in FIG. 1, according to certain embodiments.

FIG. 2 shows a block diagram of an embodiment of a data processing unit 102 of the analyte monitoring system shown in FIG. 1. User input and/or interface components may be included or a data processing unit may be free of user input and/or interface components. In certain embodiments, one or more application-specific integrated circuits (ASIC) may be used to implement one or more functions or routines associated with the operations of the data processing unit (and/or receiver unit) using for example one or more state machines and buffers.

As can be seen in the embodiment of FIG. 2, the analyte sensor 101 (FIG. 1) includes four contacts, three of which are electrodes: a work electrode (W) 210, a reference electrode (R) 212, and a counter electrode (C) 213, each operatively coupled to the analog interface 201 of the data processing unit 102. This embodiment also shows an optional guard contact (G) 211. Fewer or greater electrodes may be employed. For example, the counter and reference electrode functions may be served by a single counter/reference electrode. In some cases, there may be more than one working electrode and/or reference electrode and/or counter electrode, etc.

Figure 3:
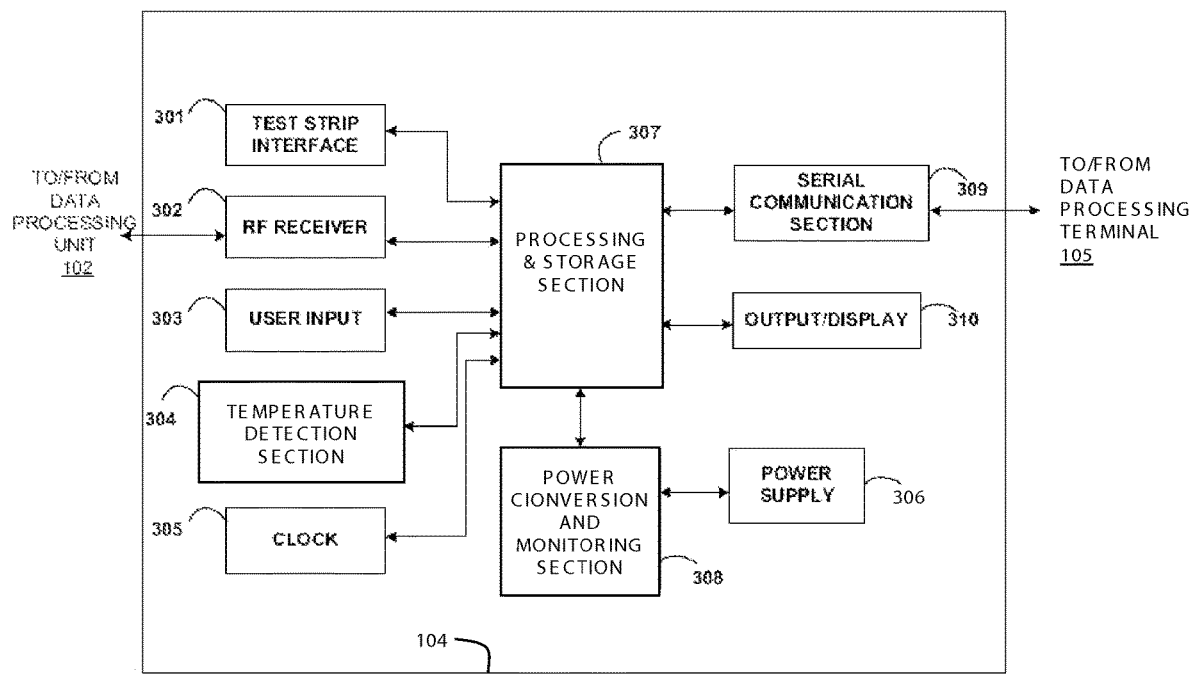
FIG. 3 shows a block diagram of an embodiment of the primary receiver unit of the analyte monitoring system of FIG. 1, according to certain embodiments.

FIG. 3 is a block diagram of an embodiment of a receiver/monitor unit such as the primary receiver unit 104 of the analyte monitoring system shown in FIG. 1. The primary receiver unit 104 includes one or more of: a test strip interface 301, an RF receiver 302, a user input 303, an optional temperature detection section 304, and a clock 305, each of which is operatively coupled to a processing and storage section 307. The primary receiver unit 104 also includes a power supply 306 operatively coupled to a power conversion and monitoring section 308. Further, the power conversion and monitoring section 308 is also coupled to the processing and storage section 307. Moreover, also shown are a receiver serial communication section 309, and an output 310, each operatively coupled to the processing and storage section 307. The primary receiver unit 104 may include user input and/or interface components or may be free of user input and/or interface components.

In certain embodiments, the test strip interface 301 includes an analyte testing portion (e.g., a glucose level testing portion) to receive a blood (or other body fluid sample) analyte test or information related thereto. For example, the test strip interface 301 may include a test strip port to receive a test strip (e.g., a glucose test strip). The device may determine the analyte level of the test strip, and optionally display (or otherwise notice) the analyte level on the output 310 of the primary receiver unit 104. Any suitable test strip may be employed, e.g., test strips that only require a very small amount (e.g., 3 microliters or less, e.g., 1 microliter or less, e.g., 0.5 microliters or less, e.g., 0.1 microliters or less), of applied sample to the strip in order to obtain accurate glucose information. Embodiments of test strips include, e.g., FreeStyle® or Precision® blood glucose test strips from Abbott Diabetes Care Inc. (Alameda, Calif.). Glucose information obtained by an in vitro glucose testing device may be used for a variety of purposes, computations, etc. For example, the information may be used to calibrate sensor 101, confirm results of sensor 101 to increase the confidence thereof (e.g., in instances in which information obtained by sensor 101 is employed in therapy related decisions), etc.

In further embodiments, the data processing unit 102 and/or the primary receiver unit 104 and/or the secondary receiver unit 106, and/or the data processing terminal/infusion device 105 may be configured to receive the analyte value wirelessly over a communication link from, for example, a blood glucose meter. In further embodiments, a user manipulating or using the analyte monitoring system 100 (FIG. 1) may manually input the analyte value using, for example, a user interface (for example, a keyboard, keypad, voice commands, and the like) incorporated in one or more of the data processing unit 102, the primary receiver unit 104, secondary receiver unit 106, or the data processing terminal/infusion device 105.

Additional detailed descriptions of exemplary sensors are provided in U.S. Pat. Nos. 5,262,035; 5,264,104; 5,262,305; 5,320,715; 5,593,852; 6,175,752; 6,650,471; 6,746,582, and 7,811,231, each of which is incorporated herein by reference in their entirety.

Figure 4:
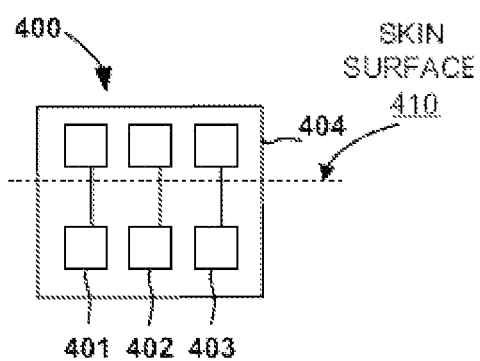
FIG. 4 shows a schematic diagram of an embodiment of an analyte sensor, according to certain embodiments.

FIG. 4 schematically shows an embodiment of an analyte sensor 400 in accordance with the embodiments of the present disclosure. This sensor embodiment includes electrodes 401, 402 and 403 on a base 404. Electrodes (and/or other features) may be applied or otherwise processed using any suitable technology, e.g., chemical vapor deposition (CVD), physical vapor deposition, sputtering, reactive sputtering, printing, coating, ablating (e.g., laser ablation), painting, dip coating, etching, and the like. Materials include, but are not limited to, any one or more of aluminum, carbon (including graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The analyte sensor 400 may be wholly implantable in a user or may be configured so that only a portion is positioned within (internal) a user and another portion outside (external) a user. For example, the sensor 400 may include a first portion positionable above a surface of the skin 410, and a second portion positioned below the surface of the skin. In such embodiments, the external portion may include contacts (connected to respective electrodes of the second portion by traces) to connect to another device also external to the user such as a transmitter unit. While the embodiment of FIG. 4 shows three electrodes side-by-side on the same surface of base 404, other configurations are contemplated, e.g., fewer or greater electrodes, some or all electrodes on different surfaces of the base or present on another base, some or all electrodes stacked together, electrodes of differing materials and dimensions, etc.

The substrate may be formed using a variety of non-conducting materials, including, for example, polymeric or plastic materials and ceramic materials. Suitable materials for a particular sensor may be determined, at least in part, based on the desired use of the sensor and properties of the materials.

In certain embodiments, the substrate is flexible. For example, if the sensor is configured for implantation into a user, then the sensor may be made flexible (although rigid sensors may also be used for implantable sensors) to reduce pain to the user and damage to the tissue caused by the implantation of and/or the wearing of the sensor. A flexible substrate often increases the user's comfort and allows a wider range of activities. Suitable materials for a flexible substrate include, for example, non-conducting plastic or polymeric materials and other non-conducting, flexible, deformable materials. Examples of useful plastic or polymeric materials include thermoplastics such as polycarbonates, polyesters (e.g., polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensors are made using a relatively rigid substrate to, for example, provide structural support against bending or breaking. Examples of rigid materials that may be used as the substrate include poorly conducting ceramics, such as aluminum oxide and silicon dioxide. An implantable sensor having a rigid substrate may have a sharp point and/or a sharp edge to aid in implantation of a sensor without an additional insertion device.

It will be appreciated that for many sensors and sensor applications, both rigid and flexible sensors will operate adequately. The flexibility of the sensor may also be controlled and varied along a continuum by changing, for example, the composition and/or thickness of the substrate.

In addition to considerations regarding flexibility, it is often desirable that implantable sensors should have a substrate which is physiologically harmless, for example, a substrate approved by a regulatory agency or private institution for in vivo use.

The sensor may include optional features to facilitate insertion of an implantable sensor. For example, the sensor may be pointed at the tip to ease insertion. In addition, the sensor may include a barb which assists in anchoring the sensor within the tissue of the user during operation of the sensor. However, the barb may be small enough so that little damage is caused to the subcutaneous tissue when the sensor is removed for replacement.

Electronics Unit

A sensor electronics unit such as a sensor control unit can be integrated in the sensor, part or all of which is subcutaneously implanted or it can be configured to be placed on the skin of a user. The sensor control unit is optionally formed in a shape that is comfortable to the user and which may permit concealment, for example, under a user's clothing. The thigh, leg, upper arm, shoulder, or abdomen are convenient parts of the user's body for placement of the sensor control unit to maintain concealment. However, the sensor control unit may be positioned on other portions of the user's body. Certain embodiments of the sensor control unit has a thin, oval shape to enhance concealment. However, other shapes and sizes may be used.

The particular profile, as well as the height, width, length, weight, and volume of the sensor control unit may vary and depends, at least in part, on the components and associated functions included in the sensor control unit. In general, the sensor control unit includes a housing may be formed as a single integral unit that rests on the skin of the user. The housing may contain most or all of the electronic components of the sensor control unit.

The housing of the sensor control unit may be formed using a variety of materials, including, for example, plastic and polymeric materials, such as rigid thermoplastics and engineering thermoplastics. Suitable materials include, for example, polyvinyl chloride, polyethylene, polypropylene, polystyrene, ABS polymers, and copolymers thereof. The housing of the sensor control unit may be formed using a variety of techniques including, for example, injection molding, compression molding, casting, and other molding methods. Hollow or recessed regions may be formed in the housing of the sensor control unit. The electronic components of the sensor control unit and/or other items, including a battery or a speaker for an audible alarm, may be placed in the hollow or recessed areas.

The sensor control unit may be attached to the skin of the user, for example, by adhering the sensor control unit directly to the skin of the user with an adhesive provided on at least a portion of the housing of the sensor control unit which contacts the skin or by suturing the sensor control unit to the skin through suture openings in the sensor control unit.

When positioned on the skin of a user, the sensor and the electronic components within the sensor control unit are coupled via conductive contacts. The one or more working electrodes, counter electrode (or counter/reference electrode), optional reference electrode, and optional temperature probe are attached to individual conductive contacts. For example, the conductive contacts are provided on the interior of the sensor control unit. Other embodiments of the sensor control unit have the conductive contacts disposed on the exterior of the housing. The placement of the conductive contacts is such that they are in contact with the contact pads on the sensor when the sensor is properly positioned within the sensor control unit.

Sensor Electronics

The sensor electronics also may include at least a portion of the electronic components that operate the sensor and the analyte monitoring device system. The electronic components of the sensor control unit may include a power supply for operating the sensor control unit and the sensor, a sensor circuit for obtaining signals from and operating the sensor, a measurement circuit that converts sensor signals to a desired format, and a processing circuit that, at minimum, obtains signals from the sensor circuit and/or measurement circuit and provides the signals to an optional transmitter. In certain embodiments, the processing circuit may also partially or completely evaluate the signals from the sensor and convey the resulting data to the optional transmitter and/or activate an optional alarm system if the analyte level exceeds a threshold. The processing circuit often includes digital logic circuitry.

The sensor control unit may optionally contain a transmitter for transmitting the sensor signals or processed data from the processing circuit to a receiver/display unit; a data storage unit for temporarily or permanently storing data from the processing circuit; a temperature probe circuit for receiving signals from and operating a temperature probe; a reference voltage generator for providing a reference voltage for comparison with sensor-generated signals; and/or a watchdog circuit that monitors the operation of the electronic components in the sensor control unit.

Moreover, the sensor control unit may also include digital and/or analog components utilizing semiconductor devices, including transistors. To operate these semiconductor devices, the sensor control unit may include other components including, for example, a bias control generator to correctly bias analog and digital semiconductor devices, an oscillator to provide a clock signal, and a digital logic and timing component to provide timing signals and logic operations for the digital components of the circuit.

As an example of the operation of these components, the sensor circuit and the optional temperature probe circuit provide raw signals from the sensor to the measurement circuit. The measurement circuit converts the raw signals to a desired format, using for example, a current-to-voltage converter, current-to-frequency converter, and/or a binary counter or other indicator that produces a signal proportional to the absolute value of the raw signal. This may be used, for example, to convert the raw signal to a format that can be used by digital logic circuits. The processing circuit may then, optionally, evaluate the data and provide commands to operate the electronics.

Calibration

Analyte sensors may be configured to require no system calibration or no user calibration. For example, a sensor may be factory calibrated and need not require further calibrating. In certain embodiments, calibration may be required, but may be done without user intervention, i.e., may be automatic. In those embodiments in which calibration by the user is required, the calibration may be according to a predetermined schedule or may be dynamic, i.e., the time for which may be determined by the system on a real-time basis according to various factors, including, but not limited to, glucose concentration and/or temperature and/or rate of change of glucose, etc.

In addition to a transmitter, an optional receiver may be included in the sensor control unit. In some cases, the transmitter is a transceiver, operating as both a transmitter and a receiver. The receiver may be used to receive calibration data for the sensor. The calibration data may be used by the processing circuit to correct signals from the sensor. This calibration data may be transmitted by the receiver/display unit or from some other source such as a control unit in a doctor's office. In addition, the optional receiver may be used to receive a signal from the receiver/display units to direct the transmitter, for example, to change frequencies or frequency bands, to activate or deactivate the optional alarm system and/or to direct the transmitter to transmit at a higher rate.

Calibration data may be obtained in a variety of ways. For instance, the calibration data may be factory-determined calibration measurements which can be input into the sensor control unit using the receiver or may alternatively be stored in a calibration data storage unit within the sensor control unit itself (in which case a receiver may not be needed). The calibration data storage unit may be, for example, a readable or readable/writeable memory circuit. In some cases, a system may only need to be calibrated once during the manufacturing process, where recalibration of the system is not required.

If necessary, calibration may be accomplished using an in vitro test strip (or other reference), e.g., a small sample test strip such as a test strip that requires less than about 1 microliter of sample (for example Freestyle® or Precision® blood glucose monitoring test strips from Abbott Diabetes Care, Alameda, Calif.). For example, test strips that require less than about 1 nanoliter of sample may be used. In certain embodiments, a sensor may be calibrated using only one sample of body fluid per calibration event. For example, a user need only lance a body part one time to obtain a sample for a calibration event (e.g., for a test strip), or may lance more than one time within a short period of time if an insufficient volume of sample is firstly obtained. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, etc., to calibrate. In certain embodiments, a system need only be calibrated once by a user, where recalibration of the system is not required.

Alternative or additional calibration data may be provided based on tests performed by a health care professional or by the user. For example, it is common for diabetic individuals to determine their own blood glucose concentration using commercially available testing kits. The results of this test is input into the sensor control unit either directly, if an appropriate input device (e.g., a keypad, an optical signal receiver, or a port for connection to a keypad or computer) is incorporated in the sensor control unit, or indirectly by inputting the calibration data into the receiver/display unit and transmitting the calibration data to the sensor control unit.

Other methods of independently determining analyte levels may also be used to obtain calibration data. This type of calibration data may supplant or supplement factory-determined calibration values.

In certain embodiments of the present disclosure, calibration data may be required at periodic intervals, for example, every eight hours, once a day, or once a week, to confirm that accurate analyte levels are being reported. Calibration may also be required each time a new sensor is implanted or if the sensor exceeds a threshold minimum or maximum value or if the rate of change in the sensor signal exceeds a threshold value. In some cases, it may be necessary to wait a period of time after the implantation of the sensor before calibrating to allow the sensor to achieve equilibrium. In certain embodiments, the sensor is calibrated only after it has been inserted. In other embodiments, no calibration of the sensor is needed.

Analyte Monitoring Device

In certain embodiments, the analyte monitoring device includes a sensor control unit and a sensor. In these embodiments, the processing circuit of the sensor control unit is able to determine a level of the analyte and activate an alarm system if the analyte level exceeds a threshold value. The sensor control unit, in these embodiments, has an alarm system and may also include a display, such as an LCD or LED display.

A threshold value is exceeded if the datapoint has a value that is beyond the threshold value in a direction indicating a particular condition. For example, a datapoint which correlates to a glucose level of 200 mg/dL exceeds a threshold value for hyperglycemia of 180 mg/dL, because the datapoint indicates that the user has entered a hyperglycemic state. As another example, a datapoint which correlates to a glucose level of 65 mg/dL exceeds a threshold value for hypoglycemia of 70 mg/dL because the datapoint indicates that the user is hypoglycemic as defined by the threshold value. However, a datapoint which correlates to a glucose level of 75 mg/dL would not exceed the same threshold value of 70 mg/dL for hypoglycemia because the datapoint does not indicate that particular condition as defined by the chosen threshold value.

An alarm may also be activated if the sensor readings indicate a value that is outside of (e.g., above or below) a measurement range of the sensor. For glucose, the physiologically relevant measurement range may be 30-400 mg/dL, including 40-300 mg/dL and 50-250 mg/dL, of glucose in the interstitial fluid.

The alarm system may also, or alternatively, be activated when the rate of change or acceleration of the rate of change in analyte level increase or decrease reaches or exceeds a threshold rate or acceleration. For example, in the case of a subcutaneous glucose monitor, the alarm system may be activated if the rate of change in glucose concentration exceeds a threshold value which may indicate that a hyperglycemic or hypoglycemic condition is likely to occur. In some cases, the alarm system is activated if the acceleration of the rate of change in glucose concentration exceeds a threshold value which may indicate that a hyperglycemic or hypoglycemic condition is likely to occur.

A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Drug Delivery System

The subject matter of the present disclosure also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

Each of the various references, presentations, publications, provisional and/or non-provisional U.S. Patent Applications, U.S. Patents, non-U.S. Patent Applications, and/or non-U.S. Patents that have been identified herein, is incorporated herein by reference in its entirety.

Other embodiments and modifications within the scope of the present disclosure will be apparent to those skilled in the relevant art. Various modifications, processes, as well as numerous structures to which the embodiments of the subject matter of the present disclosure may be applicable will be readily apparent to those of skill in the art to which the present disclosure is directed upon review of the specification. Various aspects and features of the present disclosure may have been explained or described in relation to understandings, beliefs, theories, underlying assumptions, and/or working or prophetic examples, although it will be understood that the present disclosure is not bound to any particular understanding, belief, theory, underlying assumption, and/or working or prophetic example. Although various aspects and features of the present disclosure may have been described largely with respect to applications, or more specifically, medical applications, involving diabetic humans, it will be understood that such aspects and features also relate to any of a variety of applications involving non-diabetic humans and any and all other animals. Further, although various aspects and features of the present disclosure may have been described largely with respect to applications involving partially implanted sensors, such as transcutaneous or subcutaneous sensors, it will be understood that such aspects and features also relate to any of a variety of sensors that are suitable for use in connection with the body of an animal or a human, such as those suitable for use as fully implanted in the body of an animal or a human. Finally, although the various aspects and features of the present disclosure have been described with respect to various embodiments and specific examples herein, all of which may be made or carried out conventionally, it will be understood that the present disclosure is entitled to protection within the full scope of the appended claims.

The following examples are put forth so as to provide those of ordinary skill in the art with a complete disclosure and description of how to make and use the embodiments of the present disclosure, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The temperature sensor may be internal or external to the on-body housing. The temperature sensor may also sit above the skin, or be provided as an electrode running along the analyte sensor to be transcutaneously implanted below the skin. The temperature sensor electrode would then be electrically coupled to a temperature measurement circuit within the on-body housing. The temperature measurements may be transmitted to the blood glucose meter upon request. For manufacturability and cost-effectiveness, particularly when the on-body housing is intended to be disposable, it may be desirable to avoid the inclusion of a temperature sensor and/or control circuitry in the on-body housing. As such, in certain embodiments, there is provided reader (e.g., a blood glucose meter, or other hand-held measurement or analysis instrument) with a temperature measurement sensor and control system. The temperature measurement sensor may be provided on the permanent hand-held instrument to avoid disposing of the temperature measurement components when the on-body housing is disposed.

The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times. In certain embodiments, the analyte sensor is a glucose sensor. In another embodiment, the analyte sensor is a ketone sensor.

Example Embodiments

In some aspects of the present disclosure, methods of detecting and/or determining an analyte level by compensating for ambient temperature using a single temperature sensor (e.g., coupled to an in vivo analyte sensor) are provided that include receiving an analyte sensor signal (e.g., analyte sensor information, such as current, voltage, etc.) derived from an in vivo analyte sensor; detecting a temperature measurement from a temperature sensor; determining, with a processor, whether a threshold requirement is exceeded based on the temperature measurement; and determining, with the processor, a temperature-compensated analyte sensor signal. When the threshold requirement is not exceeded, the temperature-compensated analyte sensor signal is determined using the temperature measurement. Only when the threshold requirement is exceeded, the temperature-compensated analyte sensor signal is determined using an ambient-compensated temperature that is derived by compensating the temperature measurement for ambient temperature.

In certain embodiments, the processor is coupled to an on-body unit including the in vivo analyte sensor.

In certain embodiments, the processor is coupled to a receiver that communicates wired or wirelessly with an on-body unit including the in vivo analyte sensor.

In certain embodiments, the temperature measurement is performed by an on-body unit including the in vivo analyte sensor.

In certain embodiments, the temperature measurement is performed by a receiver that communicates wired or wirelessly with an on-body unit including the in vivo analyte sensor.

In certain embodiments, the methods include determining an analyte level based on the temperature-compensated analyte sensor signal.

In certain embodiments, the temperature sensor is coupled to an on-body unit including the in vivo analyte sensor.

In certain embodiments, the temperature measurement represents skin temperature.

In certain embodiments, the ambient-compensated temperature is derived by adding a correction factor to the temperature measurement.

In certain embodiments, the analyte is glucose.

In certain embodiments, the threshold requirement includes an upper threshold value, and adding a correction factor decreases the temperature measurement when the upper threshold value is exceeded.

In certain embodiments, the threshold requirement includes a lower threshold value, and adding a correction factor increases the temperature measurement when the lower threshold value is exceeded.

In certain embodiments, the threshold requirement includes an upper threshold value and a lower threshold value, and adding a correction factor decreases the temperature measurement when the upper threshold value is exceeded and increases the temperature measurement when the lower threshold value is exceeded.

In certain embodiments, the threshold requirement is exceeded when a value of the temperature measurement exceeds the threshold requirement.

In certain embodiments, the threshold requirement is exceeded when a rate-of-change of the temperature measurement exceeds the threshold requirement.

In certain embodiments, the methods include detecting a calibration temperature measured by the temperature sensor when the on-body sensor is coupled to a body of a test subject; and determining, with a processor, a threshold requirement based on the calibration temperature.

In certain embodiments, the threshold requirement includes a predetermined amount of deviation from the calibration temperature.

In certain embodiments, the threshold requirement includes an amount of deviation from the calibration temperature, and the amount of deviation is detected by monitoring changes during a period of time.

In certain embodiments, the calibration temperature is determined based on temperature measurements during a period of time.

In certain embodiments, the threshold requirement is exceeded when a rate-of-change of the temperature measurement exceeds the threshold requirement.

In certain embodiments, the processor determining the threshold requirement is coupled to an on-body unit including the in vivo analyte sensor.

In certain embodiments, the processor determining the threshold requirement is coupled to a receiver that communicates wired or wirelessly with an on-body unit including the in vivo analyte sensor.

In some aspects of the present disclosure, analyte monitoring devices are provided. The analyte monitoring devices include a housing; a processor coupled to the housing; and memory communicably coupled to the processor. An in vivo analyte sensor is communicably coupled to the processor, and a temperature sensor is communicably coupled to the processor. The memory includes instructions stored therein that, when executed by the processor, cause the processor to receive an sensor signal from the in vivo analyte sensor; detecting a temperature measurement from the temperature sensor; determine whether a threshold requirement is exceeded based on the temperature measurement; and determine a temperature-compensated analyte sensor signal. When the threshold requirement is not exceeded, the temperature-compensated analyte sensor signal is determined using the temperature measurement. Only when the threshold requirement is exceeded, the temperature-compensated analyte sensor signal is determined using an ambient-compensated temperature that is derived by compensating the temperature measurement for ambient temperature.

In certain embodiments, the temperature measurement represents skin temperature.

In certain embodiments, the ambient-compensated temperature is derived by adding a correction factor to the temperature measurement.

In certain embodiments, the analyte is glucose.

In certain embodiments, the threshold requirement includes an upper threshold value, and adding a correction factor decreases the temperature measurement when the upper threshold value is exceeded.

In certain embodiments, the threshold requirement includes a lower threshold value, and adding a correction factor increases the temperature measurement when the lower threshold value is exceeded.

In certain embodiments, the threshold requirement includes an upper threshold value and a lower threshold value, and adding a correction factor decreases the temperature measurement when the upper threshold value is exceeded and increases the temperature measurement when the lower threshold value is exceeded.

In certain embodiments, the threshold requirement is exceeded when a value of the temperature measurement exceeds the threshold requirement.

In certain embodiments, the threshold requirement is exceeded when a rate-of-change of the temperature measurement exceeds the threshold requirement.

In certain embodiments, the memory includes instructions that, when executed by the processor, cause the processor to detect a calibration temperature measured by the temperature sensor when the analyte monitoring device is coupled to a body of a test subject; and determine a threshold requirement based on the calibration temperature.

In certain embodiments, the threshold requirement includes a predetermined amount of deviation from the calibration temperature.

In certain embodiments, the threshold requirement includes an amount of deviation from the calibration temperature, and the amount of deviation is detected by monitoring changes during a period of time.

In certain embodiments, the calibration temperature is determined based on temperature measurements during a period of time.

In certain embodiments, the threshold requirement is exceeded when a rate-of-change of the temperature measurement exceeds the threshold requirement.

In certain embodiments, the in vivo analyte sensor is coupled to the housing.

In certain embodiments, the temperature sensor is coupled to the housing.

In certain embodiments, the in vivo analyte sensor is coupled to an on-body unit, and the analyte monitoring device receives wired or wireless communications from the on-body unit.

In certain embodiments, the temperature sensor is coupled to the housing.

In certain embodiments, the memory includes instructions that, when executed by the processor, cause the processor to determine an analyte level based on the temperature-compensated analyte sensor signal.

In certain embodiments, the temperature measurement is performed by an on-body unit including the in vivo analyte sensor and communicated to the analyte monitoring device.

In certain embodiments, the temperature measurement is performed by the analyte monitoring device.

In some aspects of the present disclosure, methods of compensating for ambient temperature using a single temperature sensor are provided. The methods include detecting a temperature measurement from a temperature sensor; and determining, with a processor, an ambient-compensated temperature from the temperature measurement using an offset term.

In certain embodiments, the offset term is based on a predetermined core body temperature.

In certain embodiments, the temperature sensor is coupled to an on-body unit including an in vivo analyte sensor.

In certain embodiments, the temperature sensor protrudes from a skin-contacting surface of the on-body sensor, and the temperature measurement represents skin temperature.

In certain embodiments, the methods include receiving a sensor signal from an in vivo analyte sensor; and determining, with a processor, a temperature-compensated analyte sensor signal with the ambient-compensated temperature.

In certain embodiments, the processor that determines the ambient-compensated temperature is the same processor as the processor that determines the temperature-compensated analyte sensor signal.

In certain embodiments, the processor that determines the ambient-compensated temperature and the processor that determines the temperature-compensated analyte sensor signal are coupled to a receiver that communicates wired or wirelessly with an on-body unit including the in vivo analyte sensor.

In certain embodiments, the processor that determines the ambient-compensated temperature and the processor that determines the temperature-compensated analyte sensor signal are coupled to an on-body unit including the in vivo analyte sensor.

In certain embodiments, the processor that determines the ambient-compensated temperature is coupled to an on-body unit including the in vivo analyte sensor, and the processor that determines the temperature-compensated analyte sensor signal is coupled to a receiver that communicates wired or wirelessly with the on-body unit.

In certain embodiments, the methods include determining an analyte level based on the temperature-compensated analyte sensor signal.

In certain embodiments, the temperature measurement is performed by an on-body unit including the in vivo analyte sensor.

In certain embodiments, the temperature measurement is performed by a receiver that communicates wired or wirelessly with an on-body unit including the in vivo analyte sensor.

In certain embodiments, the temperature sensor is disposed on a printed circuit board of the on-body sensor.

In certain embodiments, the predetermined core body temperature is between 36° C. and 38° C.

In certain embodiments, the predetermined core body temperature is approximately 37° C.

In some aspects of the present disclosure, analyte monitoring devices are provided. The analyte monitoring devices include a housing; a processor coupled to the housing; and memory communicably coupled to the processor. An in vivo analyte sensor is communicably coupled to the processor, and a temperature sensor is communicably coupled to the processor. The memory includes instructions stored therein that, when executed by the processor, cause the processor to detect a temperature measurement from the temperature sensor; and determine an ambient-compensated temperature from the temperature measurement using an offset term.

In certain embodiments, the offset term is based on a predetermined core body temperature.

In certain embodiments, the temperature sensor protrudes from a skin-contacting surface of the housing, and the temperature measurement represents skin temperature.

In certain embodiments, the memory includes instructions that, when executed by the processor, cause the processor to receive a sensor signal from the in vivo analyte sensor; and determine a temperature-compensated analyte sensor signal with the ambient-compensated temperature.

In certain embodiments, the memory includes instructions that, when executed by the processor, cause the processor to determine an analyte level based on the temperature-compensated analyte sensor signal.

In certain embodiments, the in vivo analyte sensor is coupled to the housing.

In certain embodiments, the temperature sensor is coupled to the housing.

In certain embodiments, the in vivo analyte sensor is coupled to an on-body unit, and the analyte monitoring device receives wired or wireless communications from the on-body unit.

In certain embodiments, the temperature sensor is coupled to the housing.

In certain embodiments, the temperature measurement is performed by an on-body unit including the in vivo analyte sensor and communicated to the analyte monitoring device.

In certain embodiments, the temperature measurement is performed by the analyte monitoring device.

In certain embodiments, the temperature sensor is coupled to an on-body unit including the in vivo analyte sensor.

In certain embodiments, the temperature sensor is disposed on a printed circuit board coupled to the housing.

In certain embodiments, the predetermined core body temperature is between 36° C. and 38° C.

In certain embodiments, the predetermined core body temperature is approximately 37° C.

In some aspects of the present disclosure, methods of compensating for ambient temperature using temperature sensors are provided. The methods include sampling at a first sampling rate, with a processor, first temperature measurements from a first temperature sensor on an on-body sensor; determining, with a processor, first ambient-compensated temperatures from the first temperature measurements; and determining, with a processor, final ambient-compensated temperatures by applying a correction gain or factor to the first ambient-compensated temperatures. The correction gain or factor changes value at a slower rate than the sampling rate.

In certain embodiments, the processor sampling first temperatures at a first sampling rate, the processor determining first ambient-compensated temperatures, and the processor determining final ambient compensated temperatures are the same processor.

In certain embodiments, the sampling of first temperatures at a first sampling rate, the determining of first ambient-compensated temperatures, and the determining of final ambient compensated temperatures are performed by an on-body unit including an in vivo analyte sensor.

In certain embodiments, the sampling of first temperatures at a first sampling rate, the determining of first ambient-compensated temperatures, and the determining of final ambient compensated temperatures are performed by a receiver that communicates with an on-body unit including an in vivo analyte sensor.

In certain embodiments, one or more of the processor sampling first temperatures at a first sampling rate, the processor determining first ambient-compensated temperatures, and the processor determining final ambient compensated temperatures are different processors.

In certain embodiments, the sampling of first temperatures at a first sampling rate, the determining of first ambient-compensated temperatures, and the determining of final ambient compensated temperatures are each performed by either a processor coupled to an on-body unit including an in vivo analyte sensor or by a processor coupled to a receiver that communicates with the on-body unit.

In certain embodiments, the correction gain is applied to the first ambient-compensated temperatures.

In certain embodiments, the methods include sampling at the first sampling rate, with a processor, second temperature measurements from a second temperature sensor on the on-body sensor; and determining, with a processor, second ambient-compensated temperatures with the second temperature measurements. The correction gain is calculated by performing a moving average between first ambient-compensated temperatures and second ambient-compensated temperatures, such that the correction gain is based on a set of recent pairs of first ambient-compensated temperatures and second ambient-compensated temperatures.

In certain embodiments, the processor sampling first temperatures at a first sampling rate, the processor determining first ambient-compensated temperatures, the processor determining final ambient compensated temperatures, the processor sampling second temperatures at the first sampling rate, and the processor determining the second ambient-compensated temperature are the same processor.

In certain embodiments, the sampling of first temperatures at a first rate, the determining of first ambient-compensated temperatures, the determining of final ambient compensated temperatures, the determining of final ambient compensated temperatures, the sampling of second temperatures at the first sampling rate, and the determining of the second ambient-compensated temperature are performed an on-body unit including an in vivo analyte sensor.

In certain embodiments, the sampling of first temperatures at a first rate, the determining of first ambient-compensated temperatures, the determining of final ambient compensated temperatures, the determining of final ambient compensated temperatures, the sampling of second temperatures at the first sampling rate, and the determining of the second ambient-compensated temperature are performed by a receiver that communicates with an on-body unit including an in vivo analyte sensor.

In certain embodiments, one or more of the processor sampling first temperatures at a first sampling rate, the processor determining first ambient-compensated temperatures, the processor determining final ambient compensated temperatures, the processor sampling second temperatures at the first sampling rate, and the processor determining the second ambient-compensated temperature are different processors.

In certain embodiments, the sampling of first temperatures at a first rate, the determining of first ambient-compensated temperatures, the determining of final ambient compensated temperatures, the determining of final ambient compensated temperatures, the sampling of second temperatures at the first sampling rate, and the determining of the second ambient-compensated temperature are each performed by either a processor coupled to an on-body unit including an in vivo analyte sensor or by a processor coupled to a receiver that communicates with the on-body unit.

In certain embodiments, the correction gain is calculated using parameter adaptation.

In certain embodiments, the parameter adaptation is MIT adaptation.

In certain embodiments, the correction factor is applied to the first ambient-compensated temperatures.

In certain embodiments, the methods include sampling at the first sampling rate, with a processor, second temperatures measured from a second temperature sensor on the on-body sensor; and determining, with a processor, second ambient-compensated temperatures with the second temperature measurements. The correction factor is calculated by performing windowed comparisons between the first ambient-compensated temperatures and the second ambient-compensated temperatures, such that the correction factor is based on a set of recent pairs of first ambient-compensated temperatures and second ambient-compensated temperatures.

In certain embodiments, the processor sampling first temperatures at a first sampling rate, the processor determining first ambient-compensated temperatures, the processor determining final ambient compensated temperatures, the processor sampling second temperatures at the first sampling rate, and the processor determining the second ambient-compensated temperature are the same processor.

In certain embodiments, the sampling of first temperatures at a first rate, the determining of first ambient-compensated temperatures, the determining of final ambient compensated temperatures, the determining of final ambient compensated temperatures, the sampling of second temperatures at the first sampling rate, and the determining of the second ambient-compensated temperature are performed an on-body unit including an in vivo analyte sensor.

In certain embodiments, the sampling of first temperatures at a first rate, the determining of first ambient-compensated temperatures, the determining of final ambient compensated temperatures, the determining of final ambient compensated temperatures, the sampling of second temperatures at the first sampling rate, and the determining of the second ambient-compensated temperature are performed by a receiver that communicates with an on-body unit including an in vivo analyte sensor.

In certain embodiments, one or more of the processor sampling first temperatures at a first sampling rate, the processor determining first ambient-compensated temperatures, the processor determining final ambient compensated temperatures, the processor sampling second temperatures at the first sampling rate, and the processor determining the second ambient-compensated temperature are different processors.

In certain embodiments, the sampling of first temperatures at a first rate, the determining of first ambient-compensated temperatures, the determining of final ambient compensated temperatures, the determining of final ambient compensated temperatures, the sampling of second temperatures at the first sampling rate, and the determining of the second ambient-compensated temperature are each performed by either a processor coupled to an on-body unit including an in vivo analyte sensor or by a processor coupled to a receiver that communicates with the on-body unit.

In some aspects of the present disclosure analyte monitoring device are provided. The analyte monitoring device include a housing; a processor coupled to the housing; and memory communicably coupled to the processor. An in vivo analyte sensor is communicably coupled to the processor, and a first temperature sensor and second temperature sensor are communicably coupled to the processor. The memory includes instructions stored therein that, when executed by the processor, cause the processor to sample at a first sampling rate, with a processor, first temperatures measured from a first temperature sensor on the housing; determine first ambient-compensated temperatures from the first temperature measurements; and determine final ambient-compensated temperatures by applying a correction gain or factor to the first ambient-compensated temperatures. The correction gain or factor changes value at a slower rate than the sampling rate.

In certain embodiments, the in vivo analyte sensor is coupled to the housing.

In certain embodiments, the first temperature sensor and/or second temperature sensor is coupled to the housing.

In certain embodiments, the in vivo analyte sensor is coupled to an on-body unit, and the analyte monitoring device receives wired or wireless communications from the on-body unit.

In certain embodiments, the first temperature sensor and/or second temperature sensor is coupled to the housing.

In certain embodiments, the first temperature measurement and/or second temperature measurement is performed by an on-body unit including the in vivo analyte sensor and communicated to the analyte monitoring device.

In certain embodiments, the first temperature measurement and/or second temperature measurement is performed by the analyte monitoring device.

In certain embodiments, the correction gain is applied to the first ambient-compensated temperatures.

In certain embodiments, the memory includes instructions that, when executed by the processor, cause the processor to sample at the first sampling rate second temperatures measured from a second temperature sensor on the housing; and determine second ambient-compensated temperatures with the second temperature measurements. The correction gain is calculated by performing a moving average between first ambient-compensated temperatures and second ambient-compensated temperatures, such that the correction gain is based on a set of recent pairs of first ambient-compensated temperatures and second ambient-compensated temperatures.

In certain embodiments, the in vivo analyte sensor is coupled to the housing.

In certain embodiments, the first temperature sensor and/or second temperature sensor is coupled to the housing.

In certain embodiments, the in vivo analyte sensor is coupled to an on-body unit, and the analyte monitoring device receives wired or wireless communications from the on-body unit.

In certain embodiments, the first temperature sensor and/or second temperature sensor is coupled to the housing.

In certain embodiments, the first temperature measurement and/or second temperature measurement is performed by an on-body unit including the in vivo analyte sensor and communicated to the analyte monitoring device.

In certain embodiments, the first temperature measurement and/or the second temperature measurement is performed by the analyte monitoring device.

In certain embodiments, the correction gain is calculated using parameter adaptation.

In certain embodiments, the correction gain is calculated using MIT adaptation.

In certain embodiments, the correction factor is applied to the first ambient-compensated temperatures.

In certain embodiments, the memory includes instructions that, when executed by the processor, cause the processor to sample at the first sampling rate second temperatures measured from a second temperature sensor on the housing; and determine second ambient-compensated temperatures with the second temperature measurements. The correction factor is calculated by performing windowed comparisons between the first ambient-compensated temperatures and the second ambient-compensated temperatures, such that the correction factor is based on a set of recent pairs of first ambient-compensated temperatures and second ambient-compensated temperatures.

In certain embodiments, the first temperature sensor is disposed at a skin-contacting surface of the housing and the second temperature sensor is disposed on a printed circuit board coupled to the housing.

In certain embodiments, the memory includes instructions that, when executed by the processor, cause the processor to receive a sensor signal from the in vivo analyte sensor; and determine a temperature-compensated analyte sensor signal with the ambient-compensated temperature.

In certain embodiments, the memory includes instructions that, when executed by the processor, cause the processor to determine, with the processor, an analyte level based on the temperature-compensated analyte sensor signal.

In certain embodiments, the in vivo analyte sensor is coupled to the housing.

In certain embodiments, the first temperature sensor and/or second temperature sensor is coupled to the housing.

In certain embodiments, the in vivo analyte sensor is coupled to an on-body unit, and the analyte monitoring device receives wired or wireless communications from the on-body unit.

In certain embodiments, the first temperature sensor is disposed at a skin-contacting surface of the housing and the second temperature sensor is disposed on a printed circuit board on the housing.

In some aspects of the present disclosure, in vivo analyte sensors are provided. The in vivo analyte sensors include a substrate layer; an electrode layer disposed on the substrate layer; and a temperature sensing element disposed on the substrate layer, the temperature sensing element providing a signal for determining temperature adjacent the sensing area. The electrode layer includes a sensing area, In certain embodiments, the temperature sensing element is a thermistor.

In certain embodiments, the temperature sensing element is a resistance temperature detector (RTD).

In certain embodiments, the electrode layer includes a plurality of electrodes, and one electrode of the plurality of electrodes is the temperature sensing element.

In certain embodiments, the plurality of electrodes includes a working electrode, reference, electrode, and a counter electrode, and the temperature sensing element is the counter electrode and includes two contact points for electric coupling to a current providing circuit.

In certain embodiments, the temperature sensing element extends back and forth a plurality of times.

In certain embodiments, the temperature sensing element includes two traces of dissimilar metals that join at a junction adjacent the sensing area.

In certain embodiments, the two dissimilar metals are gold, silver, carbon, titanium, or an alloy thereof.

In certain embodiments, the two traces are on a same side of the substrate layer as the electrode layer.

In certain embodiments, the two traces are on an opposite side of the substrate layer as the electrode layer.

In certain embodiments, the junction is directly opposite the sensing area.

In certain embodiments, each of the two traces are on a different side of the substrate layer from one another, and a through-hole is used to join the two traces.

In certain embodiments, the two traces are conductive ink.

In certain embodiments, the temperature sensing element is a pyro-electric sensor.

In certain embodiments, the temperature sensing element is a semiconductor sensor.

In certain embodiments, the temperature sensing element includes a second sensing area and a analyte reservoir, the analyte reservoir includes a known volume of analyte at a known concentration.

In certain embodiments, the secondary sensing area is isolated and the reservoir lasts for the life of the sensor.

In certain embodiments, the analyte sensors include a membrane between the second sensing area and the reservoir.

In certain embodiments, the analyte sensors include a temporary barrier between the second sensing area and the reservoir that ceases to separate the second sensing area and the reservoir when the analyte sensor is positioned in vivo.

In some aspects of the present disclosure, analyte monitoring devices are provided that include a housing; electronic circuitry coupled to the housing, the electronic circuitry including a processor; and an in vivo analyte sensor electrically coupled to the electronic circuitry and extending from the housing. The in vivo analyte sensor include a substrate layer; an electrode layer disposed on the substrate layer; and a temperature sensing element disposed on the substrate layer, the temperature sensing element providing a signal for determining temperature adjacent a sensing area.

In certain embodiments, the temperature sensing element is a thermistor.

In certain embodiments, the temperature sensing element is a resistance temperature detector (RTD).

In certain embodiments, the electrode layer includes a plurality of electrodes, and one electrode of the plurality of electrodes is the temperature sensing element.

In certain embodiments, the plurality of electrodes includes a working electrode, reference, electrode, and a counter electrode, and the temperature sensing element is the counter electrode and includes two electrical contacts for electric coupling to a current providing circuit.

In certain embodiments, the temperature sensing element extends back and forth a plurality of times.

In certain embodiments, the electronic circuitry includes a working electrode contact that electrically couple to the working electrode, a reference electrode contact that electrically couple to the reference electrode, and two counter electrode contacts that electrically couple to the two electrical contacts of the temperature sensing element and supply the temperature sensing element with current.

In certain embodiments, the electronic circuitry includes two electrode contacts that electrically couple to two electrical contacts of the temperature sensing element and supply the temperature sensing element with current.

In certain embodiments, the temperature sensing element includes two traces of dissimilar metals that join at a junction adjacent the sensing area.

In certain embodiments, the two dissimilar metals are gold, silver, carbon, titanium, or an alloy thereof.

In certain embodiments, the two traces are on a same side of the substrate layer as the electrode layer.

In certain embodiments, the two traces are on an opposite side of the substrate layer as the electrode layer.

In certain embodiments, the junction is directly opposite the sensing area.

In certain embodiments, each of the two traces are on a different side of the substrate layer from one another, and a through-hole is used to join the two traces.

In certain embodiments, the two traces are conductive ink.

In certain embodiments, the temperature sensing element is a pyro-electric sensor.

In certain embodiments, the temperature sensing element is a semiconductor sensor.

In certain embodiments, the temperature sensing element includes a second sensing area and a analyte reservoir, the analyte reservoir includes a known volume of analyte at a known concentration.

In certain embodiments, the secondary sensing area is isolated and the reservoir lasts for the life of the analyte sensor.

In certain embodiments, the analyte sensors include a membrane between the second sensing area and the reservoir.

In certain embodiments, the analyte sensors include a temporary barrier between the second sensing area and the reservoir that ceases to separate the second sensing area and the reservoir when the analyte sensor is positioned in vivo.

In some aspects of the present disclosure, analyte sensor devices are provided that include a body including an elongated member having a central tunnel that inserts into skin of a subject; electrodes disposed on the body; and a temperature sensor coupled to the body. The body is adapted to couple to the skin of the subject.

In certain embodiments, the temperature sensor is disposed within the central tunnel and adapted to pierce the skin of the patient, and the electrodes disposed on the outside of the body.

In certain embodiments, the temperature sensor is softened by exposure to body fluids.

In certain embodiments, the central tunnel is for insulin delivery.

In certain embodiments, the electrodes include wires disposed on the body, and the temperature sensor includes a thermocouple wire disposed on the body.

In certain embodiments, the analyte sensor device includes a housing adapted to couple to an insulin delivery tube and insulin pump; and electronic circuitry coupled to the housing, the electronic circuitry including a processor for determining analyte levels.

In some aspects of the present disclosure, methods are provided that include coupling an analyte sensor device to a skin of a subject and inserting a temperature sensor within the skin of the subject. The temperature sensor is disposed within the central tunnel. The sensor coupling device includes a body including an elongated member having a central tunnel that inserts into the skin of a subject, and electrodes disposed on the body. The body is adapted to couple to the skin of the subject.

In certain embodiments, before the temperature sensor is inserted within the skin of the subject, the methods include piercing the skin of the subject with a needle disposed within the central tunnel; removing the needle from the central tunnel; and inserting the temperature sensor within the central tunnel.

In certain embodiments, the methods include determining an analyte level based on a sensor signal from the electrodes that has been compensated for temperature from the temperature sensor.

In certain embodiments, the temperature sensor is adapted to pierce the skin of the subject.

In certain embodiments, the temperature sensor is softened by exposure to body fluids.

In some aspects of the present disclosure, methods are provided that include receiving a first sensor signal from a first electrode on an in vivo analyte sensor on an on-body sensor; receiving a second sensor signal from a second electrode on the in vivo analyte sensor, and determining, with a processor, a compensated temperature at the two working electrodes based on the difference between the temperature dependencies for the different sensing chemistries on the two working electrodes. The first electrode and second electrode include different sensing chemistries with different temperature dependencies.

In certain embodiments, the temperature is determined based on a ratio of the first sensor signal and the second sensor signal.

In certain embodiments, the temperature is determined based on a predetermined temperature, sensor areas, quantity of sensing materials, and efficiencies of the sensing chemistries, and diffusion controlling membrane.

In certain embodiments, the methods include determining, with a processor, a temperature-compensated analyte sensor signal with the compensated temperature.

In certain embodiments, the processor that determines the compensated temperature is the same processor as the processor that determines the temperature-compensated analyte sensor signal.

In certain embodiments, the processor that determines the compensated temperature and the processor that determines the temperature-compensated analyte sensor signal are coupled to a receiver that communicates wired or wirelessly with an on-body unit including the in vivo analyte sensor.

In certain embodiments, the processor that determines the compensated temperature and the processor that determines the temperature-compensated analyte sensor signal are coupled to an on-body unit including the in vivo analyte sensor.

In certain embodiments, the processor that determines the compensated temperature is coupled to an on-body unit including the in vivo analyte sensor, and the processor that determines the temperature-compensated analyte sensor signal is coupled to a receiver that communicates wired or wirelessly with the on-body unit.

In certain embodiments, the methods include determining an analyte level based on the temperature-compensated analyte sensor signal.

In certain embodiments, the temperature-compensated analyte sensor signal is determined with the first sensor signal and not the second sensor signal.

In certain embodiments, the temperature-compensated analyte sensor signal is determined with the second sensor signal and not the first sensor signal.

In certain embodiments, the temperature-compensated analyte sensor signal is determined with both the first sensor signal and the second sensor signal.

In certain embodiments, the first electrode includes a first plurality of sensing elements on the in vivo analyte sensor and the second electrode includes a second plurality of sensing elements disposed on the in vivo analyte sensor.

In some aspects of the present disclosure, analyte monitoring devices are provided that include a housing; a processor coupled to the housing; and memory communicably coupled to the processor. An in vivo analyte sensor is communicably coupled to the processor, and the in vivo analyte sensor includes two working electrodes. The memory includes instructions stored therein that, when executed by the processor, cause the processor to detect a first sensor signal from a first electrode on the in vivo analyte sensor; detect a second sensor signal from a second electrode on the in vivo analyte sensor; and determine a compensated temperature at the two working electrodes based on the difference between the temperature dependencies for the different sensing chemistries on the two working electrodes. The first electrode and second electrode include different sensing chemistries with different temperature dependencies.

In certain embodiments, the in vivo analyte sensor is coupled to the housing.

In certain embodiments, the compensated temperature is determined by the analyte monitoring device.

In certain embodiments, the in vivo analyte sensor is coupled to an on-body unit, and the analyte monitoring device receives wired or wireless communications from the on-body unit.

In certain embodiments, the memory includes instructions that, when executed by the processor, cause the processor to determine an analyte level based on the temperature-compensated analyte sensor signal.

In certain embodiments, the compensated temperature is determined by an on-body unit including the in vivo analyte sensor and communicated to the analyte monitoring device.

In certain embodiments, the temperature is determined based on a ratio of the first sensor signal and the second sensor signal, In certain embodiments, the temperature is determined based on a predetermined temperature, sensor areas, quantity of sensing materials, and efficiencies of the sensing chemistries, and diffusion controlling membrane.

In certain embodiments, the memory includes instructions stored therein that, when executed by the processor, cause the processor to determining a temperature-compensated analyte sensor signal with the compensated temperature.

In certain embodiments, the in vivo analyte sensor is coupled to the housing.

In certain embodiments, the compensated temperature is determined by the analyte monitoring device.

In certain embodiments, the in vivo analyte sensor is coupled to an on-body unit, and the analyte monitoring device receives wired or wireless communications from the on-body unit.

In certain embodiments, the memory includes instructions that, when executed by the processor, cause the processor to determine an analyte level based on the temperature-compensated analyte sensor signal.

In certain embodiments, the compensated temperature is determined by an on-body unit including the in vivo analyte sensor and communicated to the analyte monitoring device.

In certain embodiments, the temperature-compensated analyte sensor signal is determined with the first sensor signal and not the second sensor signal.

In certain embodiments, the temperature-compensated analyte sensor signal is determined with the second sensor signal and not the first sensor signal.

In certain embodiments, the temperature-compensated analyte sensor signal is determined with both the first sensor signal and the second sensor signal.

In certain embodiments, the first electrode includes a first plurality of sensing elements on the in vivo analyte sensor and the second electrode includes a second plurality of sensing elements disposed on the in vivo analyte sensor.

In some aspects of the present disclosure, analyte monitoring systems are provided that include an on-body unit and receiver. The on-body includes a first processor and first memory communicably coupled to the first processor; an in vivo analyte sensor communicably coupled to the first processor; and a temperature sensor communicably coupled to the first processor. The receiver is configured to communicate with the on-body unit and includes a second processor and second memory communicably coupled to the second processor. At least one of the first and second memory includes instructions stored therein that, when executed by at least one of the first and second processors, cause the at least one first and second processors to receive a sensor signal from the in vivo analyte sensor; detect a temperature measurement from the temperature sensor; determine whether a threshold requirement is exceeded based on the temperature measurement; and determine a temperature-compensated analyte sensor signal. When the threshold requirement is not exceeded, the temperature-compensated analyte sensor signal is determined using the temperature measurement. Only when the threshold requirement is exceeded, the temperature-compensated analyte sensor signal is determined using an ambient-compensated temperature that is derived by compensating the temperature measurement for ambient temperature.

It should be appreciated that the steps may be performed in various combinations by the processor on the on-body unit and the receiver in communication with the on-body unit in different embodiments. For example, in certain embodiments, the temperature sensor is coupled to the on-body unit and a processor on the on-body unit is detecting the temperature measurement, determining whether the threshold requirement is met, performing the ambient temperature compensation, and determining the temperature-compensated signal. Then, for example, the temperature-compensated signal is sent to a receiver wherein the temperature-compensated analyte level is displayed on a user-interface of the receiver for instance. In another embodiment, for example, the temperature sensor is coupled to the on-body unit and a processor on the on-body unit transmits the temperature measurements to the receiver where a processor coupled to the receiver determines whether the threshold requirement is met, performs the ambient temperature compensation, and determines the temperature-compensated signal. Then, for example, the temperature-compensated analyte level is displayed on a user-interface of the receiver for instance. It should be appreciated that the steps may be split up in other combinations between the on-body unit and the receiver.

In certain embodiments, the temperature measurement represents skin temperature.

In certain embodiments, the ambient-compensated temperature is derived by adding a correction factor to the temperature measurement.

In certain embodiments, the analyte is glucose.

In certain embodiments, the threshold requirement includes an upper threshold value, and wherein adding a correction factor decreases the temperature measurement when the upper threshold value is exceeded.

In certain embodiments, the threshold requirement includes a lower threshold value, and wherein adding a correction factor increases the temperature measurement when the lower threshold value is exceeded.

In certain embodiments, the threshold requirement includes an upper threshold value and a lower threshold value, and wherein adding a correction factor decreases the temperature measurement when the upper threshold value is exceeded and increases the temperature measurement when the lower threshold value is exceeded.

In certain embodiments, the threshold requirement is exceeded when a value of the temperature measurement exceeds the threshold requirement.

In certain embodiments, the threshold requirement is exceeded when a rate-of-change of the temperature measurement exceeds the threshold requirement.

In certain embodiments, the at least one memory includes instructions that, when executed by the at least one first and second processor, cause the at least one first and second processor to detect a calibration temperature measured by the temperature sensor when the on-body unit is coupled to a body of a test subject; and determine a threshold requirement based on the calibration temperature.

In certain embodiments, the threshold requirement includes a predetermined amount of deviation from the calibration temperature.

In certain embodiments, the threshold requirement includes an amount of deviation from the calibration temperature, and wherein the amount of deviation is detected by monitoring changes during a period of time.

In certain embodiments, the calibration temperature is determined based on temperature measurements during a period of time.

In certain embodiments, the threshold requirement is exceeded when a rate-of-change of the temperature measurement exceeds the threshold requirement.

In certain embodiments, the at least one memory includes instructions that, when executed by the at least one first and second processor, cause the at least one first and second processor to determine an analyte level based on the temperature-compensated analyte sensor signal.

In certain embodiments, the temperature measurement is performed by the on-body unit and communicated to the receiver.

In certain embodiments, the temperature measurement is performed by the receiver.

In some aspects of the present disclosure, analyte monitoring systems are provided that include an on-body unit and receiver. The on-body includes a first processor and first memory communicably coupled to the first processor; an in vivo analyte sensor communicably coupled to the first processor; and a temperature sensor communicably coupled to the first processor. The receiver is configured to communicate with the on-body unit and includes a second processor and second memory communicably coupled to the second processor. At least one of the first and second memory includes instructions stored therein that, when executed by at least one of the first and second processors, cause the at least one first and second processors to detect a temperature measurement from the temperature sensor; and determine an ambient-compensated temperature from the temperature measurement using an offset term.

It should be appreciated that the steps may be performed in various combinations by the processor on the on-body unit and the receiver in communication with the on-body unit in different embodiments. For example, in certain embodiments, the temperature sensor is coupled to the on-body unit and a processor on the on-body unit detects the temperature measurement, determines an ambient-compensated temperature from the measured temperature using an offset term, and determines the temperature-compensated signal. Then, for example, the temperature-compensated signal is sent to a receiver wherein the temperature-compensated analyte level is displayed on a user-interface of the receiver for instance. In another embodiment, for example, the temperature sensor is coupled to the on-body unit and a processor on the on-body unit transmits the temperature measurements to the receiver where a processor coupled to the receiver determines an ambient-compensated temperature from the measured temperature using an offset term, and determines the temperature-compensated signal. Then, for example, the temperature-compensated analyte level is displayed on a user-interface of the receiver for instance. It should be appreciated that in other embodiments, the steps may be split up in other combinations between the on-body unit and the receiver.

In certain embodiments, the temperature sensor protrudes from a skin-contacting surface of the on-body unit, and wherein the temperature measurement represents skin temperature.

In certain embodiments, the at least one memory includes instructions that, when executed by the at least one first and second processor, cause the at least one first and second processor to receive a sensor signal from the in vivo analyte sensor; and determine a temperature-compensated analyte sensor signal with the ambient-compensated temperature.

In certain embodiments, the at least one memory includes instructions that, when executed by the at least one first and second processor, cause the at least one first and second processor to determine an analyte level based on the temperature-compensated analyte sensor signal.

In certain embodiments, the temperature measurement is performed by an on-body unit and communicated to the receiver.

In certain embodiments, the offset term that is based on a predetermined core body temperature.

In certain embodiments, the temperature sensor is disposed on a printed circuit board coupled to the on-body unit.

In certain embodiments, the offset term that is based on a predetermined core body temperature, and wherein the predetermined core body temperature is between 36° C. and 38° C.

In certain embodiments, the offset term that is based on a predetermined core body temperature, and wherein the predetermined core body temperature is approximately 37° C.

In some aspects of the present disclosure, analyte monitoring systems are provided that include an on-body unit and receiver. The on-body includes a first processor and first memory communicably coupled to the first processor; an in vivo analyte sensor communicably coupled to the first processor; and a first temperature sensor and second temperature sensor communicably coupled to the first processor. The receiver is configured to communicate with the on-body unit and includes a second processor and second memory communicably coupled to the second processor. At least one of the first and second memory includes instructions stored therein that, when executed by at least one of the first and second processors, cause the at least one first and second processors to sample, at a first sampling rate, first temperatures measured from a first temperature sensor; determine first ambient-compensated temperatures from the first temperature measurements; and determine final ambient-compensated temperatures by applying a correction gain or factor to the first ambient-compensated temperatures. The correction gain or factor changes value at a slower rate than the sampling rate.

It should be appreciated that the steps may be performed in various combinations by the processor on the on-body unit and the receiver in communication with the on-body unit in different embodiments. For example, in certain embodiments, the temperature sensors are coupled to the on-body unit and a processor on the on-body unit samples the temperatures sensors, determines the ambient-compensated temperature from the one-temperature sensor model and two-temperature sensor model, determines the correction factor or gain, determines the final ambient-compensated temperatures. The processor on the on-body unit may then, for example, either determine the temperature-compensated signal, or transmit the final ambient-compensated signal to a receiver having a processor that determines the temperature compensated signal and presents the corresponding analyte level on a user interface. It should be appreciated that the steps may be split up in other combinations between the on-body unit and the receiver in other embodiments. For example, in other embodiments, one or more of the steps in determining the ambient-compensated signal and/or final ambient compensated signal may be performed by the receiver.

In certain embodiments, the first temperature measurement and/or second temperature measurement is performed by the on-body unit and communicated to the receiver.

In certain embodiments, the first temperature measurement and/or second temperature measurement is performed by the receiver.

In certain embodiments, the correction gain is applied to the first ambient-compensated temperatures.

In certain embodiments, the at least one memory includes instructions that, when executed by the at least one first and second processor, cause the at least one first and second processor to sample at the first sampling rate second temperatures measured from a second temperature sensor; and determine second ambient-compensated temperatures with the second temperature measurements. The correction gain is calculated by performing a moving average between first ambient-compensated temperatures and second ambient-compensated temperatures, such that the correction gain is based on a set of recent pairs of first ambient-compensated temperatures and second ambient-compensated temperatures.

In certain embodiments, the first temperature measurement and/or second temperature measurement is performed by the on-body unit and communicated to the receiver.

In certain embodiments, the first temperature measurement and/or the second temperature measurement is performed by the receiver.

In certain embodiments, the correction gain is calculated using parameter adaptation.

In certain embodiments, the correction gain is calculated using MIT adaptation.

In certain embodiments, the correction factor is applied to the first ambient-compensated temperatures.

In certain embodiments, the at least one memory includes instructions that, when executed by the at least one first and second processor, cause the at least one first and second processor to sample at the first sampling rate second temperatures measured from a second temperature sensor; and determine second ambient-compensated temperatures with the second temperature measurements. The correction factor is calculated by performing windowed comparisons between the first ambient-compensated temperatures and the second ambient-compensated temperatures, such that the correction factor is based on a set of recent pairs of first ambient-compensated temperatures and second ambient-compensated temperatures.

In certain embodiments, the first temperature sensor is disposed at a skin-contacting surface of the on-body unit and the second temperature sensor is disposed on a printed circuit board of the on-body unit.

In certain embodiments, the at least one memory includes instructions that, when executed by the at least one first and second processor, cause the at least one first and second processor to receive a sensor signal from the in vivo analyte sensor; and determine a temperature-compensated analyte sensor signal with the ambient-compensated temperature.

In certain embodiments, the at least one memory includes instructions that, when executed by the at least one first and second processor, cause the at least one first and second processor to determine, with the processor, an analyte level based on the temperature-compensated analyte sensor signal.

In certain embodiments, the first temperature sensor is disposed at a skin-contacting surface of the on-body unit and the second temperature sensor is disposed on a printed circuit board of the on-body unit.

In some aspects of the present disclosure, analyte monitoring system are provided that include an on-body unit and receiver. The on-body includes a first processor and first memory communicably coupled to the first processor; and an in vivo analyte sensor communicably coupled to the first processor. The in vivo analyte sensor includes two working electrodes. The receiver is configured to communicate with the on-body unit and includes a second processor and second memory communicably coupled to the second processor. At least one of the first and second memory includes instructions stored therein that, when executed by at least one of the first and second processors, cause the at least one first and second processors to detect a first sensor signal from a first electrode on the in vivo analyte sensor; detect a second sensor signal from a second electrode on the in vivo analyte sensor; and determine a compensated temperature at the two working electrodes based on the difference between the temperature dependencies for the different sensing chemistries on the two working electrodes. The first electrode and second electrode include different sensing chemistries with different temperature dependencies.

It should be appreciated that the steps may be performed in various combinations by the processor on the on-body unit and the receiver in communication with the on-body unit in different embodiments. For example, in certain embodiments, the processor on the on-body unit detects the first sensor signal from the first electrode on the in vivo analyte sensor; detects the second sensor signal from a second electrode on the in vivo analyte sensor; and determines the compensated temperature at the two working electrodes based on the difference between the temperature dependencies for the different sensing chemistries on the two working electrodes. As another example, in certain embodiments, the processor on the on-body unit detects the first sensor signal from the first electrode on the in vivo analyte sensor and detects the second sensor signal from a second electrode on the in vivo analyte sensor. The first sensor signal and the second sensor signal are transmitted to the receiver. The receiver receives the first sensor signal and the second sensor signal. After the detecting the first sensor signal and the second sensor signal, the processor on the receiver determines the compensated temperature at the two working electrodes based on the difference between the temperature dependencies for the different sensing chemistries on the two working electrodes.

In certain embodiments, the compensated temperature is determined by the on-body unit.

In certain embodiments, the at least one memory includes instructions that, when executed by the at least one first and second processor, cause the at least one first and second processor to determine an analyte level based on the temperature-compensated analyte sensor signal.

In certain embodiments, the compensated temperature is determined by the on-body unit and communicated to the receiver.

In certain embodiments, the temperature is determined based on a ratio of the first sensor signal and the second sensor signal, In certain embodiments, the temperature is determined based on a predetermined temperature, sensor areas, quantity of sensing materials, and efficiencies of the sensing chemistries, and diffusion controlling membrane.

In certain embodiments, the at least one memory includes instructions that, when executed by the at least one first and second processor, cause the at least one first and second processor to determining a temperature-compensated analyte sensor signal with the compensated temperature.

In certain embodiments, the at least one memory includes instructions that, when executed by the at least one first and second processor, cause the at least one first and second processor to determine an analyte level based on the temperature-compensated analyte sensor signal.

In certain embodiments, the compensated temperature is determined by the on-body unit and communicated to the receiver.

In certain embodiments, the temperature-compensated analyte sensor signal is determined with the first sensor signal and not the second sensor signal.

In certain embodiments, the temperature-compensated analyte sensor signal is determined with the second sensor signal and not the first sensor signal.

In certain embodiments, the temperature-compensated analyte sensor signal is determined with both the first sensor signal and the second sensor signal.

In certain embodiments, the first electrode includes a first plurality of sensing elements on the in vivo analyte sensor and the second electrode includes a second plurality of sensing elements disposed on the in vivo analyte sensor.

In some aspects of the present disclosure, computer systems are provided that include a processor; and memory communicably coupled to the first processor. The memory includes instructions stored therein that, when executed by the processor, cause the processor to receive analyte data (e.g., a sensor signal from an in vivo analyte sensor); receive temperature data (e.g., a temperature measurement from a temperature sensor); determine whether a threshold requirement is exceeded based on the temperature measurement; and determine a temperature-compensated analyte sensor signal. When the threshold requirement is not exceeded, the temperature-compensated analyte sensor signal is determined using the temperature measurement. Only when the threshold requirement is exceeded, the temperature-compensated analyte sensor signal is determined using an ambient-compensated temperature that is derived by compensating the temperature measurement for ambient temperature.

In certain embodiments, the computer systems include an in vivo analyte sensor, at least one temperature sensor, a sensor electronics unit that receives analyte data from the in vivo analyte sensor, and a receiver unit that receives analyte data from the sensor electronics unit.

In certain embodiments, the temperature measurement represents skin temperature.

In certain embodiments, the ambient-compensated temperature is derived by adding a correction factor to the temperature measurement.

In certain embodiments, the analyte is glucose.

In certain embodiments, the threshold requirement includes an upper threshold value, and wherein adding a correction factor decreases the temperature measurement when the upper threshold value is exceeded.

In certain embodiments, the threshold requirement includes a lower threshold value, and wherein adding a correction factor increases the temperature measurement when the lower threshold value is exceeded.

In certain embodiments, the threshold requirement includes an upper threshold value and a lower threshold value, and wherein adding a correction factor decreases the temperature measurement when the upper threshold value is exceeded and increases the temperature measurement when the lower threshold value is exceeded.

In certain embodiments, the threshold requirement is exceeded when a value of the temperature measurement exceeds the threshold requirement.

In certain embodiments, the threshold requirement is exceeded when a rate-of-change of the temperature measurement exceeds the threshold requirement.

In certain embodiments, the memory includes instructions that, when executed by the processor, cause the processor to detect a calibration temperature measured by the temperature sensor when an on-body unit including the in vivo analyte sensor is coupled to a body of a test subject; and determine a threshold requirement based on the calibration temperature.

In certain embodiments, the threshold requirement includes a predetermined amount of deviation from the calibration temperature.

In certain embodiments, the threshold requirement includes an amount of deviation from the calibration temperature, and wherein the amount of deviation is detected by monitoring changes during a period of time.

In certain embodiments, the calibration temperature is determined based on temperature measurements during a period of time.

In certain embodiments, the threshold requirement is exceeded when a rate-of-change of the temperature measurement exceeds the threshold requirement.

In certain embodiments, the memory includes instructions that, when executed by the processor, cause the processor to determine an analyte level based on the temperature-compensated analyte sensor signal.

In certain embodiments, the temperature measurement is performed by an on-body unit and communicated to a receiver.

In certain embodiments, the temperature measurement is performed by a receiver.

In some aspects of the present disclosure, computer systems are provided that include a processor; and memory communicably coupled to the first processor. The memory includes instructions stored therein that, when executed by the processor, cause the processor to receive temperature data (e.g., a temperature measurement from a temperature sensor); and determine an ambient-compensated temperature from the temperature measurement using an offset term.

In certain embodiments, the computer systems include an in vivo analyte sensor, at least one temperature sensor, a sensor electronics unit that receives analyte data from the in vivo analyte sensor, and a receiver unit that receives analyte data from the sensor electronics unit.

In certain embodiments, the temperature sensor protrudes from a skin-contacting surface of an on-body unit, and wherein the temperature measurement represents skin temperature.

In certain embodiments, the memory includes instructions that, when executed by the processor, cause the processor to receive analyte data (e.g., a sensor signal from the in vivo analyte sensor); and determine a temperature-compensated analyte sensor signal with the ambient-compensated temperature.

In certain embodiments, the memory includes instructions that, when executed by the processor, cause the processor to determine an analyte level based on the temperature-compensated analyte sensor signal.

In certain embodiments, the temperature measurement is performed by an on-body unit and communicated to a receiver.

In certain embodiments, the offset term that is based on a predetermined core body temperature.

In certain embodiments, the temperature sensor is disposed on a printed circuit board coupled to an on-body unit.

In certain embodiments, the offset term that is based on a predetermined core body temperature, and wherein the predetermined core body temperature is between 36° C. and 38° C.

In certain embodiments, the offset term that is based on a predetermined core body temperature, and wherein the predetermined core body temperature is approximately 37° C.

In some aspects of the present disclosure, computer systems are provided that include a processor; and memory communicably coupled to the first processor. The memory includes instructions stored therein that, when executed by the processor, cause the processor to (receive temperature data (e.g., sample, at a first sampling rate, first temperatures measured from a first temperature sensor); determine first ambient-compensated temperatures from the first temperature measurements; and determine final ambient-compensated temperatures by applying a correction gain or factor to the first ambient-compensated temperatures. The correction gain or factor changes value at a slower rate than the sampling rate.

In certain embodiments, the computer systems include an in vivo analyte sensor, at least one temperature sensor, a sensor electronics unit that receives analyte data from the in vivo analyte sensor, and a receiver unit that receives analyte data from the sensor electronics unit.

In certain embodiments, the first temperature measurement and/or a second temperature measurement is performed by the on-body unit and communicated to the receiver.

In certain embodiments, the first temperature measurement and/or a second temperature measurement is performed by the receiver.

In certain embodiments, the correction gain is applied to the first ambient-compensated temperatures.

In certain embodiments, the memory includes instructions that, when executed by the processor, cause the processor to sample, at the first sampling rate, additional temperature data (e.g., second temperatures measured from a second temperature sensor); and determine second ambient-compensated temperatures with the second temperature measurements. The correction gain is calculated by performing a moving average between first ambient-compensated temperatures and second ambient-compensated temperatures, such that the correction gain is based on a set of recent pairs of first ambient-compensated temperatures and second ambient-compensated temperatures.

In certain embodiments, the first temperature measurement and/or second temperature measurement is performed by an on-body unit and communicated to a receiver.

In certain embodiments, the first temperature measurement and/or the second temperature measurement is performed by a receiver.

In certain embodiments, the correction gain is calculated using parameter adaptation.

In certain embodiments, the correction gain is calculated using MIT adaptation.

In certain embodiments, the correction factor is applied to the first ambient-compensated temperatures.

In certain embodiments, the memory includes instructions that, when executed by the processor, cause the processor to sample, at the first sampling rate, second temperatures measured from a second temperature sensor; and determine second ambient-compensated temperatures with the second temperature measurements. The correction factor is calculated by performing windowed comparisons between the first ambient-compensated temperatures and the second ambient-compensated temperatures, such that the correction factor is based on a set of recent pairs of first ambient-compensated temperatures and second ambient-compensated temperatures.

In certain embodiments, the first temperature sensor is disposed at a skin-contacting surface of an on-body unit and the second temperature sensor is disposed on a printed circuit board of the on-body unit.

In certain embodiments, the memory includes instructions that, when executed by the processor, cause the processor to receive analyte data (e.g., a sensor signal from the in vivo analyte sensor); and determine a temperature-compensated analyte sensor signal with the ambient-compensated temperature.

In certain embodiments, the memory includes instructions that, when executed by the processor, cause the processor to determine, with the processor, an analyte level based on the temperature-compensated analyte sensor signal.

In certain embodiments, the first temperature sensor is disposed at a skin-contacting surface of an on-body unit and the second temperature sensor is disposed on a printed circuit board of the on-body unit.

In some aspects of the present disclosure, computer systems are provided that include a processor; and memory communicably coupled to the first processor. The memory includes instructions stored therein that, when executed by the processor, cause the processor to receive sensor data (e.g., detect a first sensor signal) from a first electrode on the in vivo analyte sensor; receive additional sensor data (e.g., detect a second sensor signal) from a second electrode on the in vivo analyte sensor, wherein the first electrode and second electrode include different sensing chemistries with different temperature dependencies; and determine a compensated temperature at the two working electrodes based on the difference between the temperature dependencies for the different sensing chemistries on the two working electrodes.

In certain embodiments, the computer systems include an in vivo analyte sensor, at least one temperature sensor, a sensor electronics unit that receives analyte data from the in vivo analyte sensor, and a receiver unit that receives analyte data from the sensor electronics unit.

In certain embodiments, the compensated temperature is determined by an on-body unit.

In certain embodiments, the memory includes instructions that, when executed by the processor, cause the processor to determine an analyte level based on the temperature-compensated analyte sensor signal.

In certain embodiments, the compensated temperature is determined by an on-body unit and communicated to a receiver.

In certain embodiments, the temperature is determined based on a ratio of the first sensor signal and the second sensor signal, In certain embodiments, the temperature is determined based on a predetermined temperature, sensor areas, quantity of sensing materials, and efficiencies of the sensing chemistries, and diffusion controlling membrane.

In certain embodiments, the memory includes instructions that, when executed by the processor, cause the processor to determining a temperature-compensated analyte sensor signal with the compensated temperature.

In certain embodiments, the memory includes instructions that, when executed by the processor, cause the processor to determine an analyte level based on the temperature-compensated analyte sensor signal.

In certain embodiments, the compensated temperature is determined by an on-body unit and communicated to a receiver.

In certain embodiments, the temperature-compensated analyte sensor signal is determined with the first sensor signal and not the second sensor signal.

In certain embodiments, the temperature-compensated analyte sensor signal is determined with the second sensor signal and not the first sensor signal.

In certain embodiments, the temperature-compensated analyte sensor signal is determined with both the first sensor signal and the second sensor signal.

In certain embodiments, the first electrode includes a first plurality of sensing elements on the in vivo analyte sensor and the second electrode includes a second plurality of sensing elements disposed on the in vivo analyte sensor.

In some aspects of the present disclosure, computer-implemented methods of determining an analyte level by compensating for ambient temperature using a temperature sensor are provided. The computer-implemented method include receiving analyte data (e.g., a sensor signal derived from an in vivo analyte sensor); receiving temperature data (e.g., detecting a temperature measurement from a temperature sensor); determining, with a processor, whether a threshold requirement is exceeded based on the temperature measurement; and determining, with the processor, a temperature-compensated analyte sensor signal. When the threshold requirement is not exceeded, the temperature-compensated analyte sensor signal is determined using the temperature measurement. Only when the threshold requirement is exceeded, the temperature-compensated analyte sensor signal is determined using an ambient-compensated temperature that is derived by compensating the temperature measurement for ambient temperature.

In certain embodiments, the computer-implemented methods include determining an analyte level based on the temperature-compensated analyte sensor signal.

In certain embodiments, the temperature sensor is coupled to an on-body unit including the in vivo analyte sensor.

In certain embodiments, the temperature measurement represents skin temperature.

In certain embodiments, the ambient-compensated temperature is derived by adding a correction factor to the temperature measurement.

In certain embodiments, the analyte is glucose.

In certain embodiments, the threshold requirement includes an upper threshold value, and wherein adding a correction factor decreases the temperature measurement when the upper threshold value is exceeded.

In certain embodiments, the threshold requirement includes a lower threshold value, and wherein adding a correction factor increases the temperature measurement when the lower threshold value is exceeded.

In certain embodiments, the threshold requirement includes an upper threshold value and a lower threshold value, and wherein adding a correction factor decreases the temperature measurement when the upper threshold value is exceeded and increases the temperature measurement when the lower threshold value is exceeded.

In certain embodiments, the threshold requirement is exceeded when a value of the temperature measurement exceeds the threshold requirement.

In certain embodiments, the threshold requirement is exceeded when a rate-of-change of the temperature measurement exceeds the threshold requirement.

In some aspects of the present disclosure, computer-implemented methods of compensating for ambient temperature using a temperature sensor are provided. The computer-implemented methods include receiving temperature data (e.g., detecting a temperature measurement from a temperature sensor); and determining, with a processor, an ambient-compensated temperature from the temperature measurement using an offset term.

In certain embodiments, the computer-implemented methods include receiving analyte data (e.g., a sensor signal from an in vivo analyte sensor); and determining, with a processor, a temperature-compensated analyte sensor signal with the ambient-compensated temperature.

In certain embodiments, the computer-implemented methods include determining an analyte level based on the temperature-compensated analyte sensor signal.

In certain embodiments, the offset term that is based on a predetermined core body temperature.

In certain embodiments, the predetermined core body temperature is between 36° C. and 38° C.

In certain embodiments, the predetermined core body temperature is approximately 37° C.

In some aspects of the present disclosure, computer-implemented methods of compensating for ambient temperature using temperature sensors are provided. The computer-implemented methods include receiving temperature data (e.g., sampling at a first sampling rate, with a processor, first temperature measurements from a first temperature sensor on an on-body sensor); determining, with a processor, first ambient-compensated temperatures from the first temperature measurements; and determining, with a processor, final ambient-compensated temperatures by applying a correction gain or factor to the first ambient-compensated temperatures. The correction gain or factor changes value at a slower rate than the sampling rate.

In certain embodiments, the correction gain is applied to the first ambient-compensated temperatures.

In certain embodiments, the computer-implemented methods include receiving second sensor data (e.g., sampling at the first sampling rate, with a processor, second temperature measurements from a second temperature sensor on the on-body sensor); and determining, with a processor, second ambient-compensated temperatures with the second temperature measurements. The correction gain is calculated by performing a moving average between first ambient-compensated temperatures and second ambient-compensated temperatures, such that the correction gain is based on a set of recent pairs of first ambient-compensated temperatures and second ambient-compensated temperatures.

In certain embodiments, one or more of the processor sampling first temperatures at a first sampling rate, the processor determining first ambient-compensated temperatures, the processor determining final ambient compensated temperatures, the processor sampling second temperatures at the first sampling rate, and the processor determining the second ambient-compensated temperature are different processors.

In certain embodiments, the sampling of first temperatures at a first rate, the determining of first ambient-compensated temperatures, the determining of final ambient compensated temperatures, the determining of final ambient compensated temperatures, the sampling of second temperatures at the first sampling rate, and the determining of the second ambient-compensated temperature are each performed by either a processor coupled to an on-body unit including an in vivo analyte sensor or by a processor coupled to a receiver that communicates with the on-body unit.

In certain embodiments, the correction gain is calculated using parameter adaptation.

In certain embodiments, the parameter adaptation is MIT adaptation.

In certain embodiments, the correction factor is applied to the first ambient-compensated temperatures.

In certain embodiments, the computer-implemented methods include sampling at the first sampling rate, with a processor, second temperatures measured from a second temperature sensor on the on-body sensor; and determining, with a processor, second ambient-compensated temperatures with the second temperature measurements. The correction factor is calculated by performing windowed comparisons between the first ambient-compensated temperatures and the second ambient-compensated temperatures, such that the correction factor is based on a set of recent pairs of first ambient-compensated temperatures and second ambient-compensated temperatures.

In some aspects of the present disclosure, computer-implemented methods are provided that receive sensor data (e.g., a first sensor signal from a first electrode on an in vivo analyte sensor on an on-body sensor); receive additional sensor data (e.g., a second sensor signal from a second electrode on the in vivo analyte sensor); and determine a compensated temperature at the two working electrodes based on the difference between the temperature dependencies for the different sensing chemistries on the two working electrodes. The first electrode and second electrode include different sensing chemistries with different temperature dependencies.

In certain embodiments, the temperature is determined based on a ratio of the first sensor signal and the second sensor signal.

In certain embodiments, the temperature is determined based on a predetermined temperature, sensor areas, quantity of sensing materials, and efficiencies of the sensing chemistries, and diffusion controlling membrane.

In certain embodiments, the computer-implemented methods include determining, with a processor, a temperature-compensated analyte sensor signal with the compensated temperature.

In certain embodiments, the computer-implemented methods include determining an analyte level based on the temperature-compensated analyte sensor signal.

In certain embodiments, the temperature-compensated analyte sensor signal is determined with the first sensor signal and not the second sensor signal.

In certain embodiments, the temperature-compensated analyte sensor signal is determined with the second sensor signal and not the first sensor signal.

In certain embodiments, the temperature-compensated analyte sensor signal is determined with both the first sensor signal and the second sensor signal.

In certain embodiments, the first electrode includes a first plurality of sensing elements on the in vivo analyte sensor and the second electrode includes a second plurality of sensing elements disposed on the in vivo analyte sensor.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

It should be understood that techniques introduced above can be implemented by programmable circuitry programmed or configured by software and/or firmware, or they can be implemented entirely by special-purpose "hardwired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

The term "logic", as used herein, can include, for example, special purpose hardwired circuitry, software and/or firmware in conjunction with programmable circuitry, or a combination thereof.

What is claimed is:

1. A method of compensating for ambient temperature using a single temperature sensor comprising:
   receiving a sensor signal from an in vivo glucose sensor comprising a sensing area, wherein the in vivo glucose sensor comprises a first portion arranged above a skin surface of a user and a second portion positioned below the skin surface and in contact with interstitial fluid, wherein the second portion comprises the sensing area;
   detecting a temperature measurement from a temperature sensor, wherein the temperature sensor is disposed in a housing and is arranged above the skin surface of the user;
   determining, with a processor communicably coupled to the in vivo glucose sensor and the temperature sensor, an ambient-compensated temperature from the temperature measurement using an offset term based on a core body temperature, wherein the ambient-compensated temperature is an estimated temperature of the sensing area; and
   determining, with the processor, a temperature-compensated glucose sensor signal with the thus determined ambient-compensated temperature.

2. The method according to claim 1, wherein the offset term is between 36° C. and 38° C.

3. The method according to claim 2, wherein the core body temperature is approximately 37° C.

4. A glucose monitoring device, comprising:
   a housing;
   a processor coupled to the housing;
   wherein an in vivo glucose sensor comprising a sensing area is communicably coupled to the processor, wherein the in vivo glucose sensor comprises a first portion configured to be arranged above a skin surface of a user and a second portion configured to be positioned below the skin surface and in contact with interstitial fluid, wherein the second portion comprises the sensing area;
   wherein a temperature sensor is communicably coupled to the processor, wherein the temperature sensor is disposed in the housing and is configured to be arranged above the skin surface of the user; and
   memory communicably coupled to the processor, wherein the memory includes instructions stored therein that, when executed by the processor, cause the processor to:
   receive a sensor signal from the in vivo glucose sensor;
   detect a temperature measurement from the temperature sensor; and
   determine an ambient-compensated temperature from the temperature measurement using an offset term based on a core body temperature, wherein the ambient-compensated temperature is an estimated temperature of the sensing area; and
   determine a temperature-compensated glucose sensor signal with the thus determined ambient-compensated temperature.

5. A glucose monitoring device according to claim 4, wherein the offset term is between 36° C. and 38° C.

6. A glucose monitoring device according to claim 5, wherein the offset term is approximately 37° C.

7. A glucose monitoring system, comprising:
   a glucose monitoring device, comprising:
      a first processor and a first memory communicably coupled to the first processor;
      an in vivo glucose sensor comprising a sensing area communicably coupled to the first processor, wherein the in vivo glucose sensor comprises a first portion configured to be arranged above a skin surface of a user and a second portion configured to be positioned below the skin surface and in contact with interstitial fluid, wherein the second portion comprises the sensing area; and
      a temperature sensor communicably coupled to the first processor, wherein the temperature sensor is disposed in a housing and is configured to be arranged above the skin surface of the user; and
   a receiver configured to communicate with the glucose monitoring device, the receiver comprising:
      a second processor and a second memory communicably coupled to the second processor;
   wherein at least one of the first memory and the second memory includes instructions stored therein that, when executed by at least one of the first and second processors, cause the at least one of the first and second processors to:
      receive a sensor signal from the in vivo glucose sensor;
      detect a temperature measurement from the temperature sensor;
      determine an ambient-compensated temperature from the temperature measurement using an offset term based on a core body temperature, wherein the ambient-compensated temperature is an estimated temperature of the sensing area; and
      determine a temperature-compensated glucose sensor signal with the thus determined ambient-compensated temperature.

8. The method of claim 1, wherein the temperature sensor comprises a pyroelectric sensor having an optical path to the skin surface, and wherein the detected temperature is a temperature of the skin surface.

9. The glucose monitoring device of claim 4, wherein the temperature sensor comprises a pyroelectric sensor having an optical path to the skin surface, and wherein the detected temperature is a temperature of the skin surface.

10. The glucose monitoring device of claim 4, wherein the temperature sensor comprises a thermocouple temperature sensor, wherein the in vivo glucose sensor comprises a sensor substrate having a metal trace disposed on a first side of the sensor substrate and conductive ink disposed on a second side of the sensor substrate, wherein the sensor substrate defines a through-hole extending from the first side to the second side and containing the conductive ink so as to form a thermocouple junction between the metal trace and the conductive ink.

11. The glucose monitoring device of claim 4, wherein the in vivo glucose sensor further comprises a second sensing area and a reservoir containing a glucose solution at a known concentration, wherein the second sensing area is configured to be arranged under the skin surface to generate a second sensor signal, and wherein the sensor signal is adjusted based on the second sensor signal to account for temperature.

12. The glucose monitoring system of claim 7, wherein the in vivo glucose sensor further comprises a second sensing area and a reservoir containing a glucose solution at a known concentration, wherein the second sensing area is configured to be arranged under the skin surface to generate a second sensor signal, and wherein the sensor signal is adjusted based on the second sensor signal to account for temperature.

* * * * *